(12) United States Patent
Lan et al.

(10) Patent No.: US 10,815,197 B2
(45) Date of Patent: Oct. 27, 2020

(54) N-SULFONYL BENZAMIDES AS VOLTAGE-GATED SODIUM CHANNEL INHIBITORS

(71) Applicants: SHANGHAI HAIYAN PHARMACEUTICAL TECHNOLOGY CO., LTD., Shanghai (CN); YANGTZE RIVER PHARMACEUTICAL GROUP CO., LTD., Jiangsu (CN)

(72) Inventors: Jiong Lan, Shanghai (CN); Fusheng Zhou, Shanghai (CN); Jinzhu Zhao, Shanghai (CN); Dong Huang, Shanghai (CN); Jing Xie, Shanghai (CN); Yi Hu, Shanghai (CN); Qiang Lv, Shanghai (CN)

(73) Assignees: SHANGHAI HAIYAN PHARMACEUTICAL TECHNOLOGY CO., LTD., Shanghai (CN); YANGTZE RIVER PHARMACEUTICAL GROUP CO., LTD., Shanghai (CN)

( * ) Notice: Subject to any disclaimer, the term of this patent is extended or adjusted under 35 U.S.C. 154(b) by 0 days.

(21) Appl. No.: 16/068,627

(22) PCT Filed: Jan. 24, 2017

(86) PCT No.: PCT/CN2017/072470
§ 371 (c)(1),
(2) Date: Jul. 6, 2018

(87) PCT Pub. No.: WO2017/133591
PCT Pub. Date: Aug. 10, 2017

(65) Prior Publication Data
US 2019/0023654 A1    Jan. 24, 2019

(30) Foreign Application Priority Data

Feb. 3, 2016 (CN) .......................... 2016 1 0079358

(51) Int. Cl.
| | | |
|---|---|---|
| *A61K 31/166* | (2006.01) |
| *C07C 233/64* | (2006.01) |
| *C07D 207/09* | (2006.01) |
| *C07D 401/04* | (2006.01) |
| *C07D 211/46* | (2006.01) |
| *C07D 295/155* | (2006.01) |
| *A61K 31/4439* | (2006.01) |
| *A61K 31/495* | (2006.01) |
| *C07D 213/74* | (2006.01) |
| *A61K 31/496* | (2006.01) |
| *A61K 31/451* | (2006.01) |
| *C07D 207/08* | (2006.01) |
| *A61K 31/40* | (2006.01) |
| *C07D 213/80* | (2006.01) |
| *C07D 241/04* | (2006.01) |

(52) U.S. Cl.
CPC ............ *C07D 207/09* (2013.01); *A61K 31/40* (2013.01); *A61K 31/4439* (2013.01); *A61K 31/451* (2013.01); *A61K 31/495* (2013.01); *A61K 31/496* (2013.01); *C07D 207/08* (2013.01); *C07D 211/46* (2013.01); *C07D 213/74* (2013.01); *C07D 213/80* (2013.01); *C07D 241/04* (2013.01); *C07D 295/155* (2013.01); *C07D 401/04* (2013.01)

(58) Field of Classification Search
CPC ........................... A61K 31/166; C07C 233/64
USPC ......................................... 514/217; 564/183
See application file for complete search history.

(56) References Cited

U.S. PATENT DOCUMENTS

| 2013/0023541 A1 | 1/2013 | Boehm et al. |
| 2015/0224071 A1 | 8/2015 | Chowdhury et al. |
(Continued)

FOREIGN PATENT DOCUMENTS

| CA | 3011169 | * 8/2017 |
| CN | 102802627 A | 11/2012 |
(Continued)

OTHER PUBLICATIONS

Jordan, V. C. Nature Reviews: Drug Discovery, 2, 2003, 205.*
(Continued)

*Primary Examiner* — Douglas M Willis
(74) *Attorney, Agent, or Firm* — Mintz Levin Cohn Ferris Glovsky and Popeo PC

(57) ABSTRACT

The present invention discloses an N-sulfonyl benzamide derivative with a heterocyclic substituent, and a preparation method therefor and a pharmaceutical application thereof. More specifically, the invention discloses a compound represented by formula (II) or a pharmaceutically acceptable salt, stereoisomer, solvent compound, or prodrug thereof, and a preparation method therefor and an application thereof. Refer to the specification for definitions of each group in the formula.

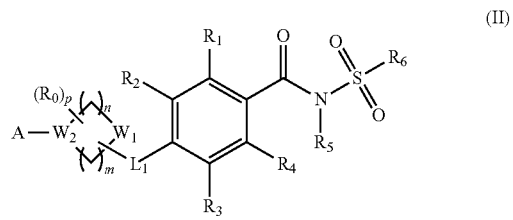

2 Claims, 1 Drawing Sheet

(56) References Cited

U.S. PATENT DOCUMENTS

2015/0322002 A1 11/2015 Dehnhardt et al.
2015/0336944 A1 11/2015 Kim et al.

FOREIGN PATENT DOCUMENTS

| CN | 104718188 A | 6/2015 |
| CN | 104718205 A | 6/2015 |
| CN | 104797555 A | 7/2015 |
| WO | 2006/124865 A2 | 11/2006 |
| WO | 2006/124865 A3 | 11/2006 |
| WO | 2012/007869 A2 | 1/2012 |
| WO | 2012/007869 A3 | 1/2012 |
| WO | 2015/051043 A1 | 4/2015 |
| WO | 2015/078374 A1 | 6/2015 |
| WO | 2016/124139 A1 | 8/2016 |

OTHER PUBLICATIONS

Vippagunta, et al. Advanced Drug Delivery Reviews, 48, 2001, 18.*
Wolff, Manfred E., Ed. Burger's Medicinal Chemistry and Drug Discovery—Fifth Edition, vol. 1: Principles and Practice, New York: John Wiley & Sons, 1994, 975-977.*
English Translation of the International Search Report dated May 2, 2017 corresponding to PCT/CN2017/072470 filed Jan. 24, 2017; 6 pages.

* cited by examiner

N-SULFONYL BENZAMIDES AS VOLTAGE-GATED SODIUM CHANNEL INHIBITORS

TECHNICAL FIELD

The invention belongs to the technical field of medicine. In particular, the present invention relates to a heterocycle substituted N-sulfonylbenzamide derivative and preparation as well as use thereof as an inhibitor of sodium ion channels (in particular Nav1.7), as well as pharmaceutical compositions and medicinal compositions prepared from it.

BACKGROUND

Recently, Cox et al in England reported unexpected results for the first time in Nature that the mutation of SCN9A gene which encoded a voltage-gated Nav1.7 channel led to the painlessness of genetic individuals. The genetically mutated individuals congenitally lost feeling of pain, but the other functions of the body were completely normal. In addition, recent studies have shown that the voltage-gated Nav1.7 channel expressed in DRG neurons is involved in the production of pain signals and functions as a gate to control the introduction of pain signals. The study suggests that the Nav1.7 channel may become a drug target that selectively treats pain without side effects.

Nav1.7 (PN1, SCN9A) VGSC is sensitive to tetrodotoxin blockade and is mainly expressed in peripheral sympathetic neurons and sensory neurons. The SCN9A gene has been replicated by many species (including humans, rats, and rabbits) and has been shown approximately 90% identity of amino acids between human and rat genes.

More and more evidences of body show that Nav1.7 plays an important role in a variety of pain states (including acute, chronic, inflammatory and/or neuropathic pain). In humans, Nav1.7 protein accumulates in neuromas, especially neuromas that cause pain. Mutations with increased function of Nav1.7 (whether hereditary or sporadic) have been considered to be involved in primary erythematous limb pain (a condition characterized by cautery and inflammation of the extremities), and suddenly extreme pain. The reported results that the non-selective sodium channel blockers lidocaine and mexiletine can alleviate the symptoms of hereditary erythematous limb pain, and carbamazepine can effectively reduce the number and severity of PEPD attacks are consistent with the above observations. Additional evidence for the role of Nav1.7 in pain can be found in the phenotype of the mutation of the loss of function of the SCN9A gene. Follow-up studies have shown resulted loss in the function of SCN9A gene and many different mutations in CIP phenotype.

Since Nav1.7 is specifically expressed in DRG sensory neurons but not in other tissues such as cardiomyocytes and central nervous system, the development of specific blockers for the treatment of chronic pain will not only increase efficacy but also reduce side effects, and selective inhibitors of Nav1.7 ion channel can be used for almost all kinds of pain treatment.

Many patients with acute or chronic pain disorders respond poorly to current pain therapies, and are generally resistant and insensitive to opiates. In addition, the efficacies of currently used sodium channel blockers for the above-mentioned diseases are largely limited by many side effects. These side effects include various CNS disorders such as blurred vision, dizziness, nausea and sedation, and more potentially life-threatening arrhythmias and heart failure.

Therefore, in view of the limited potency and unacceptable side effects of currently available pharmaceuticals, there is an urgent need to develop safer and more effective analgesics with higher efficacy and fewer side effects. The Nav1.7 ion channel is an important target for the development of non-addictive analgesics. Although there are many patents reporting various Nav1.7 ion channel inhibitors, the effects on other ion channels such as potassium channel and human liver microsomal stability should also be concerned with the development of highly active Nav1.7 ion channel inhibitors. Since the influences of the cardiotoxicity associated with the HERG potassium channel and the human liver microsomal stability index predicting the liver clearance of the compound on drug development are crucial, the development of highly selective Nav1.7 ion channel inhibitors are necessary.

SUMMARY OF INVENTION

The object of the present invention is to provide, based on the existing Nav1.7 inhibitors, an inhibitor which is highly selective to Nav1.7 sodium ion channel and has stable metabolic stability of liver microsomes and its application in medicine.

In the first aspect of the present invention, a compound of formula (I), or a pharmaceutically acceptable salt, solvate, stereoisomer or prodrug thereof is provided:

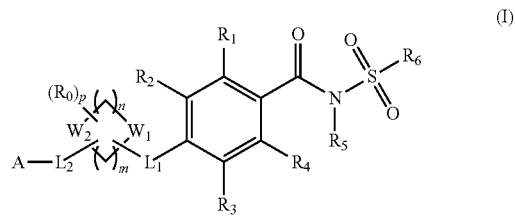

(I)

wherein $R_1$, $R_2$, $R_3$, $R_4$ are each independently a hydrogen, hydroxyl, CN, $NO_2$, halogen, —$NR_aR_b$, $C_{1-20}$ alkyl, $C_{3-20}$ cycloalkyl, $C_{3-20}$ cycloalkoxy, $C_{2-20}$ alkenyl, $C_{2-20}$ alkynyl, $C_{1-20}$ alkoxy, —CHO, —CO—($C_{1-20}$ alkyl), —CO—($C_{6-20}$ aryl), $C_{6-20}$ aryl, —$CONR_aR_b$, —C(O)O—($C_{1-20}$ alkyl), —OC(O)—($C_{1-20}$ alkyl), —$SO_2$—($C_{1-20}$ alkyl) or —$SO_2$—($C_{6-20}$ aryl);

$R_5$ is a hydrogen, $C_{1-20}$ alkyl, $C_{3-20}$ cycloalkyl, halogenated $C_{1-20}$ alkyl;

$R_6$ is a $C_{6-20}$ aryl, $C_{1-20}$ alkyl, $C_{3-20}$ cycloalkyl, $C_{3-8}$ heterocyclyl, —$NR_aR_b$; the $C_{3-8}$ heterocyclyl contains 1 to 3 heteroatoms selected from N, O, S, wherein $R_a$, $R_b$ are each independently a hydrogen, $C_{1-20}$ alkyl, $C_{3-20}$ cycloalkyl or $C_{6-20}$ aryl;

$L_1$, $L_2$ are attached at any different positions on the ring and are each independently a bond, or —C(O)N($R^y$)—, —N($R^y$)C(O)—, —N($R^y$)$SO_2$—, —$SO_2$N($R^y$)—, —OC(O)—, —C(O)O—, —$(CR^yR^x)_{r1}(O)_{r2}(CR^yR^x)_{r3}$—, —S(O)—, —$SO_2$—, —N($R^y$)—, —O—, —S—, —C(O)— or cyclopropylidene; wherein $R^y$, $R^x$ are each independently a hydrogen, halogen, hydroxyl, CN, $NO_2$, $C_{1-20}$ alkyl, halogenated $C_{1-20}$ alkyl, $C_{3-20}$ cycloalkyl, $C_{2-20}$ alkenyl, $C_{2-20}$ alkynyl or $C_{6-20}$ aryl; r1, r3 are each independently a 0, 1, 2 or 3; r2 is 0 or 1;

$W_1$, $W_2$ are each independently C, N, O or S;

n, m are each independently 0, 1, 2 or 3, and n and m are not simultaneously 0; wherein when n is 0 or m is 0, $W_1$ and $W_2$ are connected through a single bond;

$(R_0)_p$ means that hydrogens at any positions on the ring are substituted by p $R_0$, p is 0, 1, 2, 3, 4 or 5, each $R_0$ is the same or different and is independently a hydrogen, deuterium, $C_{1-20}$ alkyl, deuterated $C_{1-20}$ alkyl or halogenated $C_{1-20}$ alkyl; or any two $R_0$ is connected through a single bond or —$(CH_2)_{p1}$—, and p1 is 1, 2 or 3;

A is a $C_{6-20}$ aryl, 3 to 7 membered monocyclic ring, 8 to 10 membered bicyclic ring, 3 to 7 membered mono heterocyclic ring, 8 to 10 membered bis-heterocyclic ring, 5 or 6 membered monocyclic heteroaryl ring, 8 to 10 membered bicyclic heteroaryl ring, benzo 3-7 membered monocyclic ring, benzo 3-7 membered mono heterocyclic ring, condensed ring of 5-6 membered monocyclic heteroaryl ring and 3-7 membered monocyclic ring, condensed ring of 5-6 membered monocyclic heteroaryl ring and 3-7 membered mono heterocyclic ring;

wherein the alkyl, cycloalkyl, cycloalkoxy, alkenyl, alkynyl, alkoxy, aryl, 3 to 7 membered monocyclic ring, 8 to 10 membered bicyclic ring, 3 to 7 membered mono heterocyclic ring, 8 to 10 membered bis-heterocyclic ring, 5 or 6 membered monocyclic heteroaryl ring, 8 to 10 membered bicyclic heteroaryl ring, benzo 3-7 membered monocyclic ring, benzo 3-7 membered mono heterocyclic ring, condensed ring of 5-6 membered monocyclic heteroaryl ring and 3-7 membered monocyclic ring, or condensed ring of 5-6 membered monocyclic heteroaryl ring and 3-7 membered mono heterocyclic ring is substituted or unsubstituted; and the substitution means that 1-5 hydrogens in the group are substituted by a substituent selected from the group consisting of halogen, nitro, hydroxyl, cyano, $C_{6-20}$ aryl, $C_{1-20}$ alkyl, halogenated $C_{1-20}$ alkyl, $C_{1-20}$ alkoxy, halogenated $C_{1-20}$ alkoxy, $C_{3-20}$ cycloalkyl, halogenated $C_{3-20}$ cycloalkyl, $C_{3-20}$ cycloalkoxy, halogenated $C_{3-20}$ cycloalkoxy, $C_{2-20}$ alkenyl, halogenated $C_{2-20}$ alkenyl, $C_{2-20}$ alkynyl, halogenated $C_{2-20}$ alkynyl, $C_{1-20}$ alkylthio, halogenated $C_{1-20}$ alkylthio, $C_{1-20}$ alkylamino, halogenated $C_{1-20}$ alkylamino, thiol, 3 to 20 membered heterocycloalkyl, 3 to 20 membered heterocycloalkyloxy, $C_{3-20}$ cycloalkylthio, halogenated $C_{3-20}$ cycloalkylthio, 3 to 20 membered heterocycloalkylthio, oxo, $C_{1-20}$ hydroxyalkyl, carboxyl, —$NR_aR_b$, —$C(O)NR_aR_b$, —$N(R_a)C(O)$—($C_{1-20}$ alkyl), —$N(R_a)SO_2$—($C_{1-20}$ alkyl), —$SO_2N(R_aR_b)$, —$C(O)O$—($C_{1-20}$ alkyl), —CHO, —OC(O)—($C_{1-20}$ alkyl), —$SO_2$—($C_{1-20}$ alkyl), —$SO_2$—($C_{6-20}$ aryl), —CO—($C_{6-20}$ aryl); $R_a$, $R_b$ are each independently a hydrogen, $C_{1-20}$ alkyl, $C_{3-20}$ cycloalkyl or $C_{6-20}$ aryl.

In another preferred example, $R_6$ is $C_{3-10}$ cycloalkyl, $C_{3-8}$ heterocyclyl.

In another preferred example, $R_6$ is cyclopropyl, cyclobutyl, cyclopentyl, cyclohexyl.

In another preferred example, $R_1$, $R_2$, $R_3$, $R_4$ are each independently a hydrogen, halogen, $C_{1-20}$ alkyl, $C_{3-20}$ cycloalkyl, $C_{3-20}$ cycloalkoxy or $C_{1-20}$ alkoxy.

In another preferred example, $R_2$ and $R_4$ are hydrogen, and $R_1$, $R_3$ are each independently a hydrogen, halogen, $C_{3-20}$ cycloalkyl, $C_{1-20}$ alkyl, $C_{3-20}$ cycloalkoxy or $C_{1-20}$ alkoxy.

In another preferred example, $R_5$ is a hydrogen.

In another preferred example, A is $C_{6-20}$ aryl or 5 or 6 membered monocyclic heteroaryl ring; the aryl or 5 or 6 membered monocyclic heteroaryl ring is substituted or unsubstituted; and the substitution means that 1-5 hydrogens in the group are substituted by a substituent selected from the group consisting of halogen, $C_{1-20}$ alkyl, halogenated $C_{1-20}$ alkyl, $C_{1-20}$ alkoxy, halogenated $C_{1-20}$ alkoxy, $C_{3-20}$ cycloalkyl, and $C_{3-20}$ cycloalkoxy.

In another preferred example, the $C_{6-20}$ aryl is phenyl; the 5 or 6 membered monocyclic heteroaryl ring is pyridyl.

In another preferred example, the phenyl is

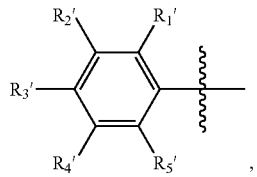

wherein $R_1'$, $R_2'$, $R_3'$, $R_4'$, $R_5'$ are each independently a hydrogen, halogen, nitro, hydroxyl, cyano, $C_{6-20}$ aryl, $C_{1-20}$ alkyl, halogenated $C_{1-20}$ alkyl, halogenated $C_{1-20}$ alkoxy, $C_{1-20}$ alkoxy, $C_{3-20}$ cycloalkyl, halogenated $C_{3-20}$ cycloalkyl, $C_{3-20}$ cycloalkoxy, halogenated $C_{3-20}$ cycloalkoxy, $C_{2-20}$ alkenyl, halogenated $C_{2-20}$ alkenyl, $C_{2-20}$ alkynyl, halogenated $C_{2-20}$ alkynyl, —$NR_aR_b$, —$C(O)NR_aR_b$, —$N(R_a)C(O)$—($C_{1-20}$ alkyl), —$N(R_a)SO_2$—($C_{1-20}$ alkyl), —$SO_2N(R_aR_b)$, —$C(O)O$—($C_{1-20}$ alkyl), —CHO, —OC(O)—($C_{1-20}$ alkyl), —$SO_2$—($C_{1-20}$ alkyl), —$SO_2$—($C_{6-20}$ aryl), —CO—($C_{1-20}$ alkyl), —CO—($C_{6-20}$ aryl); and/or the pyridyl is

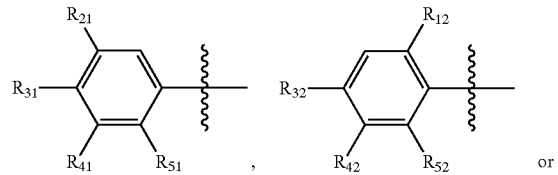

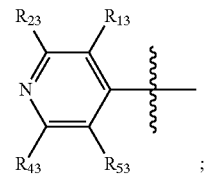

wherein $R_{21}$, $R_{31}$, $R_{41}$, $R_{51}$, $R_{12}$, $R_{32}$, $R_{42}$, $R_{52}$, $R_{13}$, $R_{23}$, $R_{43}$, $R_{53}$ are each independently a hydrogen, halogen, nitro, hydroxyl, cyano, $C_{6-20}$ aryl, $C_{1-20}$ alkyl, halogenated $C_{1-20}$ alkyl, halogenated $C_{1-20}$ alkoxy, $C_{1-20}$ alkoxy, $C_{3-20}$ cycloalkyl, halogenated $C_{3-20}$ cycloalkyl, $C_{3-20}$ cycloalkoxy, halogenated $C_{3-20}$ cycloalkoxy, $C_{2-20}$ alkenyl, halogenated $C_{2-20}$ alkenyl, $C_{2-20}$ alkynyl, halogenated $C_{2-20}$ alkynyl, —$NR_aR_b$, —$C(O)NR_aR_b$, —$N(R_a)C(O)$—($C_{1-20}$ alkyl), —$N(R_a)SO_2$—($C_{1-20}$ alkyl), —$SO_2N(R_aR_b)$, —$C(O)O$—($C_{1-20}$ alkyl), —CHO, —OC(O)—($C_{1-20}$ alkyl), —$SO_2$—($C_{1-20}$ alkyl), —$SO_2$—($C_{6-20}$ aryl), —CO—($C_{1-20}$ alkyl), —CO—($C_{6-20}$ aryl); $R_a$, $R_b$ are defined as above.

In another preferred example, $R_1'$, $R_2'$, $R_3'$, $R_4'$, $R_5'$ are each independently a hydrogen, halogen, $C_{1-20}$ alkyl, halogenated $C_{1-20}$ alkyl, halogenated $C_{1-20}$ alkoxy, $C_{1-20}$ alkoxy, $C_{3-20}$ cycloalkyl, $C_{3-20}$ cycloalkoxy.

In another preferred example, $R_{21}$, $R_{31}$, $R_{41}$, $R_{51}$, $R_{12}$, $R_{32}$, $R_{42}$, $R_{52}$, $R_{13}$, $R_{23}$, $R_{43}$, $R_{53}$ are each independently a hydrogen, halogen, $C_{1-20}$ alkyl, halogenated $C_{1-20}$ alkyl, halogenated $C_{1-20}$ alkoxy, $C_{1-20}$ alkoxy, $C_{3-20}$ cycloalkyl, $C_{3-20}$ cycloalkoxy.

In another preferred example,

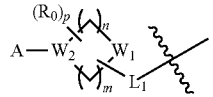

is selected from

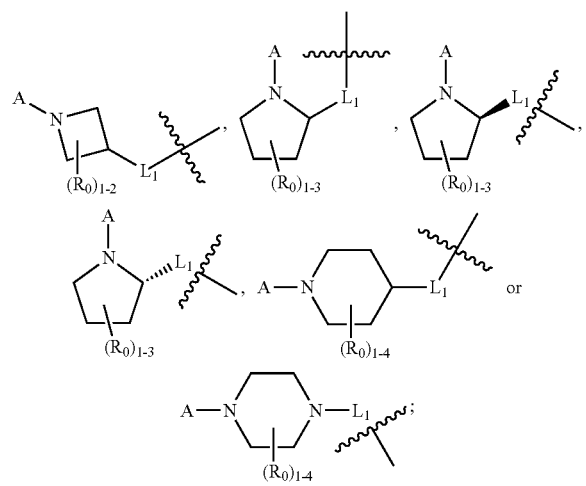

A, $L_0$, $R_0$ are defined as in the specification.

In another preferred example, $L_1$ is $-(CR^yR^x)_{r1}(O)_{r2}(CR^yR^x)_{r3}-$; wherein $R^y$, $R^x$ are each independently a hydrogen; r1, r3 are each independently 0, 1, 2 or 3; r2 is 0 or 1.

In another preferred example, r2 is 0.

In another preferred example, (i) r1, r3 are 0; r2 is 1;

(ii) r1 is 1, 2 or 3; r2 is 1; r3 is 0;

(iii) r1 is 0; r2 is 1; r3 is 1, 2 or 3; or (iv) r1, r2, r3 are 0.

In another preferred example, $W_2$ is N, O, S or C, when $W_2$ is O or S, $L_2$ is linked to any other carbon atom on the ring except $W_1$ and $W_2$, and when $W_2$ is N or C, $L_2$ is linked to any other ring atom except $W_1$. Preferably, $L_2$ is linked to $W_2$.

In another preferred example, $L_2$ is a bond, and A is linked to any other ring atom except $W_1$.

In another preferred example, $L_2$ is a bond, $W_2$ is N, O, S or C, when $W_2$ is O or S, A is linked to any other carbon atom on the ring except $W_1$ and $W_2$, and when $W_2$ is N or C, A is linked to any other ring atom except $W_1$.

In another preferred example, $W_1$ is N, O, S or C, when $W_1$ is O or S, $L_1$ is linked to any other carbon atom on the ring except $W_1$ and $W_2$, and when $W_1$ is N or C, $L_1$ is linked to any other ring atom except $W_2$. Preferably, $L_1$ is linked to $W_1$.

In another preferred example, the compound is a compound of formula (II):

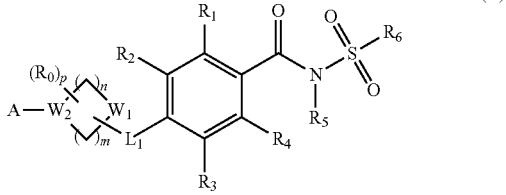

wherein $R_0$, $R_1$, $R_2$, $R_3$, $R_4$, $R_5$, $R_6$, A, $L_1$, $W_1$, $W_2$, n, p, m are defined as in claim 1.

In another preferred example, each $R_0$ is the same or different and is each independently a hydrogen.

In another preferred example, A is $C_{6-20}$ aryl or 5 or 6 membered monocyclic heteroaryl ring.

In another preferred example, A is phenyl or pyridyl; the phenyl or pyridyl is substituted or unsubstituted; and the substitution means that 1-5 hydrogens in the group are substituted by a substituent selected from the group consisting of a halogen, $C_{1-20}$ alkyl, halogenated $C_{1-20}$ alkyl, $C_{1-20}$ alkoxy, halogenated $C_{1-20}$ alkoxy, $C_{3-20}$ cycloalkyl, and $C_{3-20}$ cycloalkoxy.

In another preferred example, $L_1$ is a bond, or $-(CR^yR^x)_{r1}(O)_{r2}(CR^yR^x)_{r3}-$; wherein $R^y$, $R^x$ are each independently a hydrogen; r1, r3 are each independently 0, 1, 2 or 3; r2 is 0 or 1.

In another preferred example, the compound is a compound of formula (III):

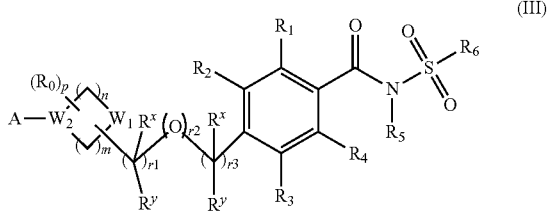

wherein $R_0$, $R_1$, $R_2$, $R_3$, $R_4$, $R_5$, $R_6$, $R^x$, $R^y$, r1, r2, r3, A, $W_1$, $W_2$, n, p, m are defined as in claim 1. In another preferred example, in the compound of formula (III), $W_1$ is N, O, S or C, when $W_1$ is O or S, $(CR^yR^x)_{r1}$ is linked to any other carbon atom on the ring except $W_1$ and $W_2$, and when $W_1$ is N or C, $(CR^yR^x)_{r1}$ is linked to any other ring atom except $W_2$, and r1 is as defined above.

In another preferred example,

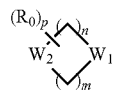

is selected from

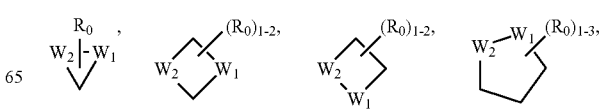

-continued
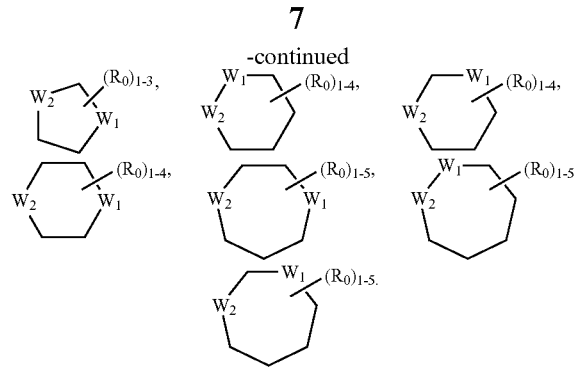
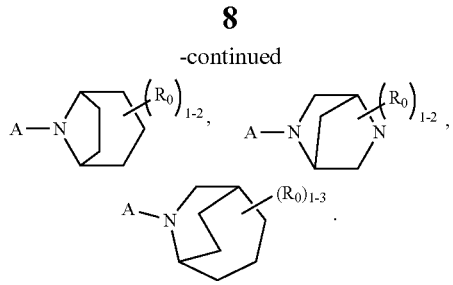
In another preferred example, W₂ is N.
In another preferred example, W₁ is N, O, S or C.
In another preferred example,
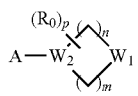
is selected from
In another preferred example
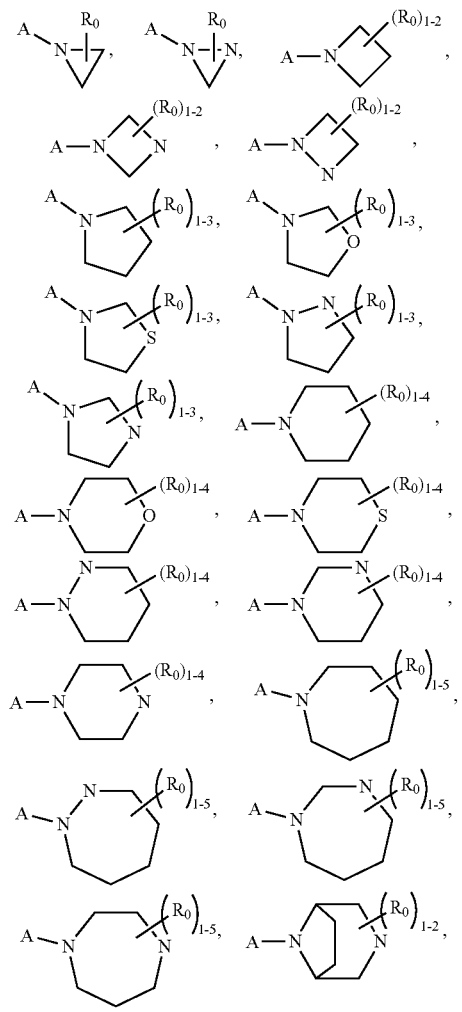
is selected from
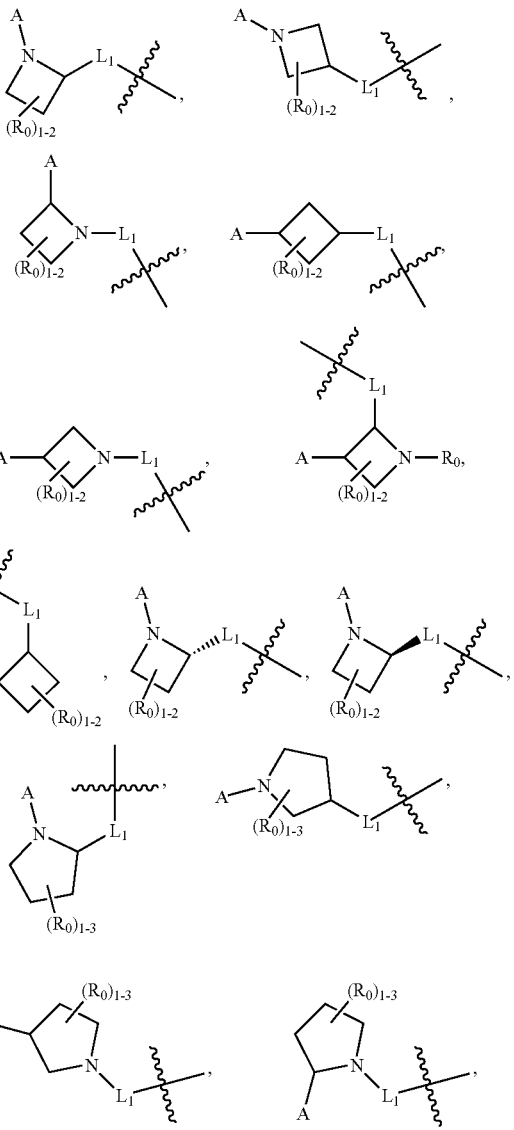

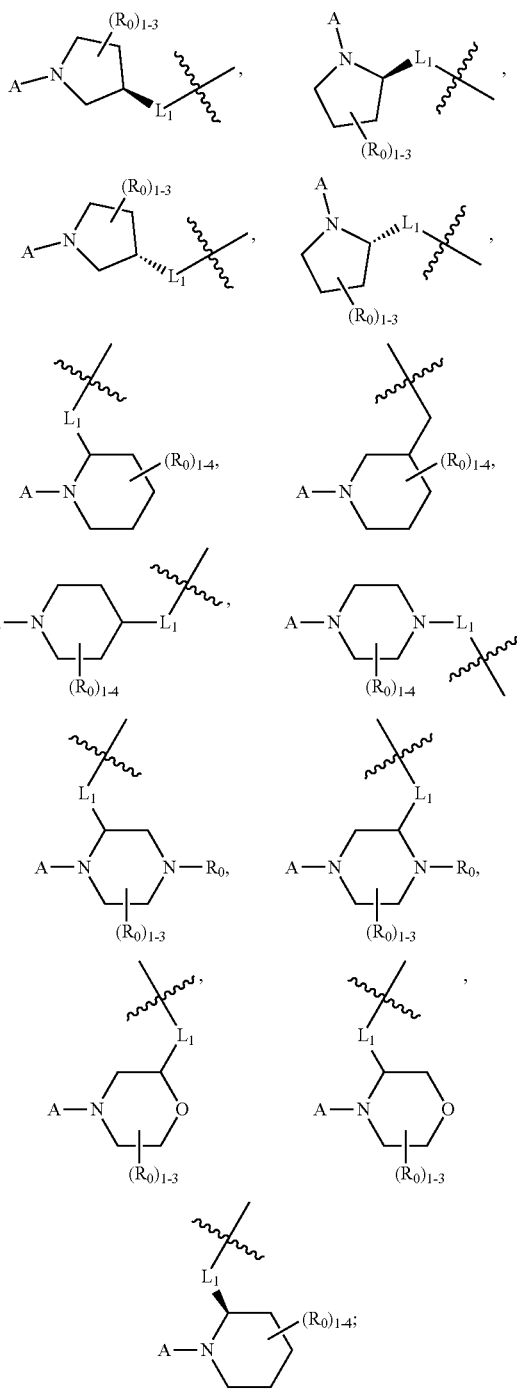

wherein A, L$_1$, R$_0$ are defined as before.

In another preferred example, is selected from wherein A, L$_1$, R$_0$ are defined as before.

In another preferred example, is selected from wherein A, L$_1$, R$_0$ are defined as before.

In another preferred example, is selected from and L$_1$ is a bond, or —(CR$^y$R$^x$)$_{r1}$(O)$_{r2}$(CR$^y$R$^x$)$_{r3}$—; wherein R$^y$, R$^x$ are each independently a hydrogen; r1, r3 are each independently 0, 1, 2 or 3; r2 is 0 or 1; each R$_0$ is the same or different and is each independently a hydrogen.

In another preferred example, A is

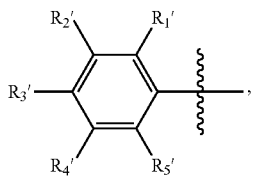

wherein $R_1'$, $R_2'$, $R_3'$, $R_4'$, $R_5'$ are defined as in the specification.

In another preferred example,

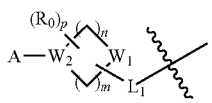

is selected from:

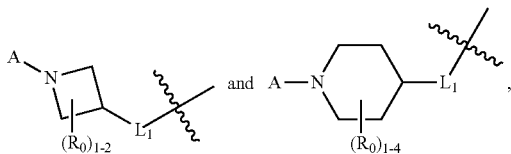

wherein A, $L_1$, $R_0$ are defined as before.

In another preferred example,

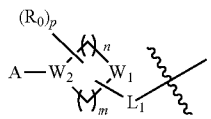

is selected from:

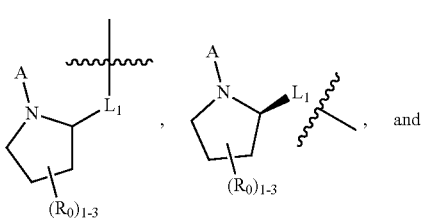

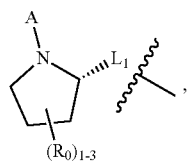

wherein A, $L_1$, $R_0$ are defined as before.

In another preferred example, the compound is a compound of formula (IV):

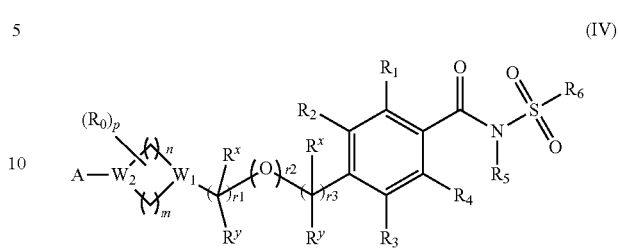

(IV)

wherein $R_0$, $R_1$, $R_2$, $R_3$, $R_4$, $R_5$, $R_6$, $R^x$, $R^y$, r1, r2, r3, A, $W_2$, n, p, m are defined as before; and $W_1$ is N or C.

In another preferred example, r2 is 0.

In another preferred example, r1, r3 are 0; r2 is 1.

In another preferred example, r1 is 1, 2 or 3; r2 is 1; r3 is 0.

In another preferred example, r1 is 0; r2 is 1; r3 is 1, 2 or 3.

In another preferred example, r1, r2, r3 is 0.

In another preferred example, the compound is a compound of formula (V):

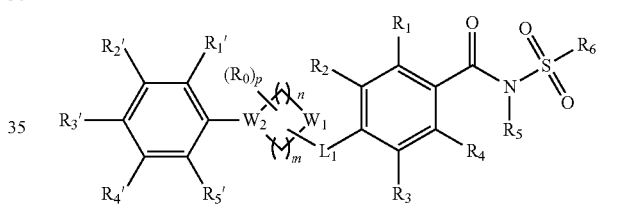

(V)

wherein $R_0$, $R_1$, $R_2$, $R_3$, $R_4$, $R_5$, $R_6$, $L_1$, $W_1$, $W_2$, n, p, m are defined as before; $R_1'$, $R_2'$, $R_3'$, $R_4'$, $R_5'$ are each independently a hydrogen, halogen, nitro, hydroxyl, cyano, $C_{6-20}$ aryl, $C_{1-20}$ alkyl, halogenated $C_{1-20}$ alkyl, halogenated $C_{1-20}$ alkoxy, $C_{1-20}$ alkoxy, $C_{3-20}$ cycloalkyl, halogenated $C_{3-20}$ cycloalkyl, $C_{3-20}$ cycloalkoxy, halogenated $C_{3-20}$ cycloalkoxy, $C_{2-20}$ alkenyl, halogenated $C_{2-20}$ alkenyl, $C_{2-20}$ alkynyl, halogenated $C_{2-20}$ alkynyl, —$NR_aR_b$, —C(O)$NR_aR_b$, —N($R_a$)C(O)—($C_{1-20}$ alkyl), —N($R_a$)$SO_2$—($C_{1-20}$ alkyl), —$SO_2N(R_aR_b)$, —C(O)O—($C_{1-20}$ alkyl), —CHO, —OC(O)—($C_{1-20}$ alkyl), —$SO_2$—($C_{1-20}$ alkyl), —$SO_2$—($C_{6-20}$ aryl), —CO—($C_{1-20}$ alkyl), —CO—($C_{6-20}$ aryl); and $R_a$, $R_b$ are as defined above.

In another preferred example, $R_1'$, $R_2'$, $R_3'$, $R_4'$, $R_5'$ are each independently a hydrogen, halogen, $C_{1-20}$ alkyl, halogenated $C_{1-20}$ alkyl, halogenated $C_{1-20}$ alkoxy, $C_{1-20}$ alkoxy, $C_{3-20}$ cycloalkyl.

In another preferred example, in the compound of formula (V), $L_1$ is —$(CR^yR^x)_{r1}(O)_{r2}(CR^yR^x)_{r3}$—, and r1, r2, r3 are defined as above.

In another preferred example, in the compound of formula (V), $W_1$ is N, O, S or C, when $W_1$ is O or S, $L_1$ is linked to any other carbon atom on the ring except $W_1$ and $W_2$, and when $W_1$ is N or C, $L_1$ is linked to any other ring atom except $W_2$. Preferably, $L_1$ is linked to $W_1$.

In another preferred example, in the compound of formula (V), $W_2$ is N.

In another preferred example, $R_1$, $R_2$, $R_3$, $R_4$ are each independently a hydrogen, halogen, $C_{1-20}$ alkyl, $C_{3-20}$ cycloalkyl;

$R_5$ is hydrogen;

$R_6$ is $C_{1-20}$ alkyl, —$NR_aR_b$;

wherein $R_a$, $R_b$ are each independently a hydrogen, or $C_{1-20}$ alkyl;

$W_1$, $W_2$ are each independently C, O, S or N;

$L_2$ is a bond;

$L_1$ is a bond, or —$(CR^yR^x)_{r1}(O)_{r2}(CR^yR^x)_{r3}$—, —O— or —C(O)—; wherein $R^y$, $R^x$ are each independently a hydrogen; r1, r3 are each independently 0 or 1; and r2 is 0 or 1;

n, m are each independently 1 or 2;

$(R_0)_p$ means that hydrogens at any positions on the ring are substituted by p $R_0$, p is 0;

A is phenyl;

and when $W_1$ and/or $W_2$ is O or S, $L_1$ and A are respectively linked to any other carbon atom on the ring except $W_1$ and $W_2$;

when $W_1$ and/or $W_2$ is N or C, A is linked to any other ring atom except $W_1$, and $L_1$ is linked to any other ring atom except $W_2$;

wherein the alkyl, cycloalkyl or phenyl is substituted or unsubstituted; and the substitution means that 1-5 hydrogens in the group are substituted by a substituent selected from the group consisting of a halogen, $C_{1-20}$ alkyl, halogenated $C_{1-20}$ alkyl, $C_{1-20}$ alkoxy, halogenated $C_{1-20}$ alkoxy.

In another preferred example, $R_2$ and $R_4$ are hydrogen, and $R_1$, $R_3$ are each independently a halogen, $C_{3-6}$ cycloalkyl, $C_{1-3}$ alkyl, $C_{3-6}$ cycloalkoxy or $C_{1-3}$ alkoxy.

In another preferred example, $L_2$ is a bond (means that A is linked to any other ring atom except $W_1$), or is —$(CH_2)_{r1}(O)_{r2}(CH_2)_{r3}$—, —O—, —C(O)—, —S(O)—, —$SO_2$— or —$N(R^y)$—, wherein r1, r2, r3, $R^y$ are defined as above.

In another preferred example, the compound is any one of the compounds of formulas (I) to (V), wherein $R_1$, $R_2$, $R_3$, $R_4$ are each independently a hydrogen, halogen, $C_{1-20}$ alkyl, $C_{3-20}$ cycloalkyl;

$R_5$ is hydrogen;

$R_6$ is $C_{1-20}$ alkyl, —$NR_aR_b$; wherein $R_a$, $R_b$ are each independently a hydrogen, $C_{1-20}$ alkyl.

In another preferred example, A is $C_{6-20}$ aryl or 5 or 6 membered monocyclic heteroaryl ring.

In another preferred example, $L_2$ is a bond; or $L_1$ is a bond, or —$(CRR^x)_{r1}(O)_{r2}(CR^yR^x)_{r3}$—; wherein $R^y$, $R^x$ are each independently a hydrogen; r1, r3 are each independently 0, 1, 2 or 3; r2 is 0 or 1.

In another preferred example, each $R_0$ is the same or different and is each independently a hydrogen.

In another preferred example,

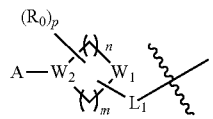

is selected from:

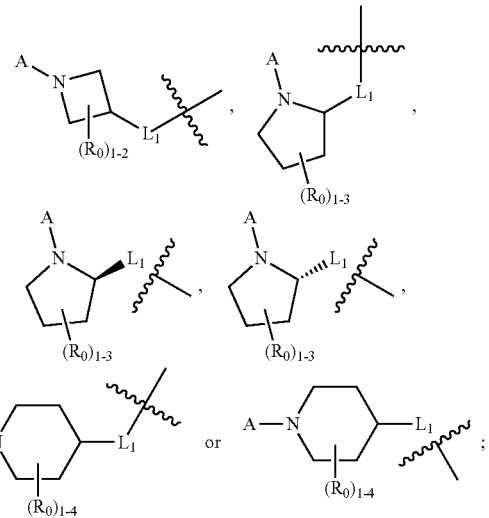

A is $C_{6-20}$ aryl or 5 or 6 membered monocyclic heteroaryl ring;

$L_1$ is a bond, or —$(CR^yR^x)_{r1}(O)_{r2}(CR^yR^x)_{r3}$—; wherein $R^y$, $R^x$ are each independently a hydrogen; r1, r3 are each independently 0, 1, 2 or 3; r2 is 0 or 1;

each $R_0$ is the same or different and is each independently a hydrogen;

the alkyl, cycloalkyl, aryl, 5 or 6 membered monocyclic heteroaryl ring are substituted or unsubstituted; and the substitution means that 1-5 hydrogens in the group are substituted by a substituent selected from the group consisting of a halogen, nitro, hydroxyl, cyano, $C_{6-20}$ aryl, $C_{1-20}$ alkyl, halogenated $C_{1-20}$ alkyl, $C_{1-20}$ alkoxy, halogenated $C_{1-20}$ alkoxy, $C_{3-20}$ cycloalkyl, halogenated $C_{3-20}$ cycloalkyl, $C_{3-20}$ cycloalkoxy, halogenated $C_{3-20}$ cycloalkoxy, $C_{2-20}$ alkenyl, halogenated $C_{20}$ alkenyl, $C_{2-20}$ alkynyl, halogenated $C_{2-20}$ alkynyl, $C_{1-20}$ alkylthio, halogenated $C_{1-20}$ alkylthio, $C_{1-20}$ alkylamino, halogenated $C_{1-20}$ alkylamino, thiol, 3 to 20 membered heterocycloalkyl, 3 to 20 membered heterocycloalkyloxy, $C_{3-20}$ cycloalkylthio, halogenated $C_{3-20}$ cycloalkylthio, 3 to 20 membered heterocycloalkylthio, oxo, $C_{1-20}$ hydroxyalkyl, carboxyl, —$NR_aR_b$, —$C(O)NR_aR_b$, —$N(R_a)C(O)$—($C_{1-20}$ alkyl), —$N(R_a)SO_2$—($C_{1-20}$ alkyl), —$SO_2N(R_aR_b)$, —$C(O)O$—($C_{1-20}$ alkyl), —CHO, —OC(O)—($C_{1-20}$ alkyl), —$SO_2$—($C_{1-20}$ alkyl), —$SO_2$—($C_{6-20}$ aryl), —CO—($C_{6-20}$ aryl); and $R_a$, $R_b$ are each independently a hydrogen, $C_{1-20}$ alkyl, $C_{3-20}$ cycloalkyl or $C_{6-20}$ aryl.

In another preferred example, A is phenyl or pyridyl; the phenyl or pyridyl is substituted or unsubstituted; and the substitution means that 1-5 hydrogens in the group are substituted by a substituent selected from the group consisting of a halogen, $C_{1-20}$ alkyl, halogenated $C_{1-20}$ alkyl, $C_{1-20}$ alkoxy, halogenated $C_{1-20}$ alkoxy $C_{3-20}$ cycloalkyl, $C_{3-20}$ cycloalkoxy.

In another preferred example, the phenyl is

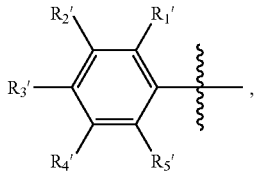

wherein $R_1'$, $R_2'$, $R_3'$, $R_4'$, $R_5'$ are each independently a hydrogen, halogen, $C_{1-20}$ alkyl, halogenated $C_{1-20}$ alkyl, halogenated $C_{1-20}$ alkoxy, $C_{1-20}$ alkoxy, $C_{3-20}$ cycloalkyl.

In another preferred example,

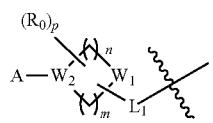

is selected from:

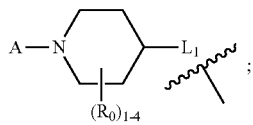

$L_1$ is a bond, or $-(CR^yR^x)_{r1}(O)_{r2}(CR^yR^x)_{r3}-$; wherein $R^y$, $R^x$ are each independently a hydrogen; r1, r3 are each independently 0, 1, 2 or 3; r2 is 0 or 1; and each $R_0$ is the same or different and is each independently a hydrogen.

In another preferred example, r1 is 0; r3 is 1; r2 is 0.

In another preferred example,

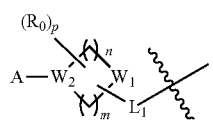

is selected from

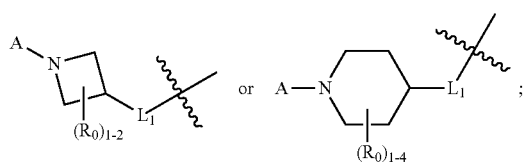

$L_1$ is a bond, or $-(CR^yR^x)_{r1}(O)_{r2}(CR^yR^x)_{r3}-$; wherein $R^y$, $R^x$ are each independently a hydrogen; r1, r3 are each independently a 0, 1, 2 or 3; r2 is 0 or 1; and each $R_0$ is the same or different and is each independently a hydrogen.

In another preferred example, r1, r3 is 0; r2 is 1.

In another preferred example,

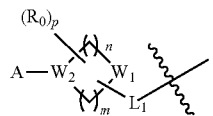

is selected from

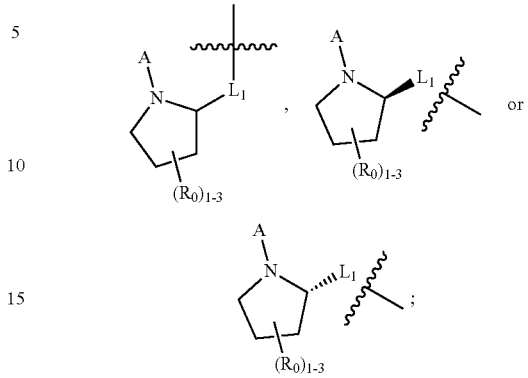

$L_1$ is a bond, or $-(CR^yR^x)_{r1}(O)_{r2}(CR^yR^x)_{r3}-$; wherein $R^y$, $R^x$ are each independently a hydrogen; r1, r3 are each independently 0, 1, 2 or 3; r2 is 0 or 1; and each $R_0$ is the same or different and is each independently a hydrogen.

In another preferred example, r1 is 1, 2 or 3; r2 is 1; r3 is 0.

In another preferred example, r1 is 1; r2 is 1; r3 is 0.

In another preferred example, $R_1$, $R_3$ are each independently a hydrogen, halogen, $C_{1-20}$ alkyl or $C_{3-20}$ cycloalkyl; $R_2$ and $R_4$ are hydrogen.

In another preferred example, $C_{1-20}$ alkyl is methyl, ethyl, n-propyl, isopropyl, n-butyl.

In another preferred example, $C_{3-20}$ cycloalkyl is cyclopropyl.

In another preferred example, halogenated $C_{1-20}$ alkyl is trifluoromethoxy.

In another preferred example, halogenated $C_{1-20}$ alkoxy is trifluoromethoxy, trifluoroethoxy, difluoromethoxy.

In another preferred example, $C_{1-20}$ alkoxy is methoxy, ethoxy, isopropoxy, tert-butoxy, isobutoxy.

In another preferred example, $C_{3-20}$ cycloalkoxy is cyclopropoxy.

In another preferred example, halogen is fluorine or chlorine.

In another preferred example, the compound is selected from the group consisting of:

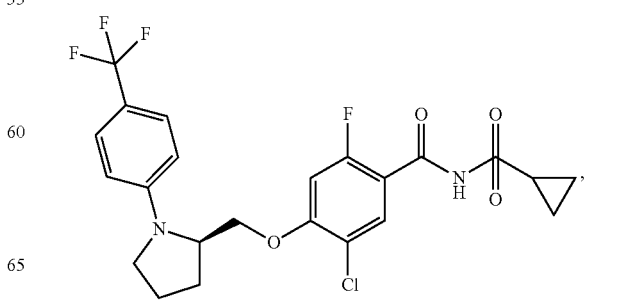

Z-80

-continued
Z-89
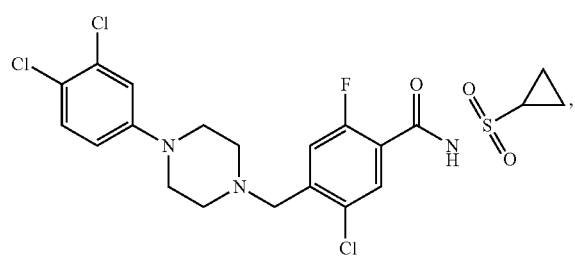
Z-92
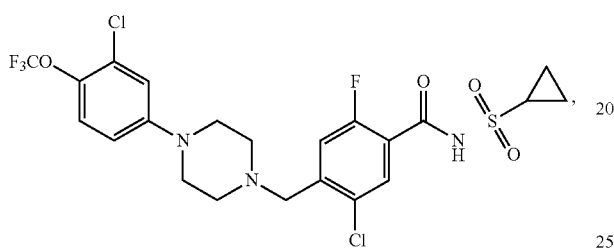
Z-117
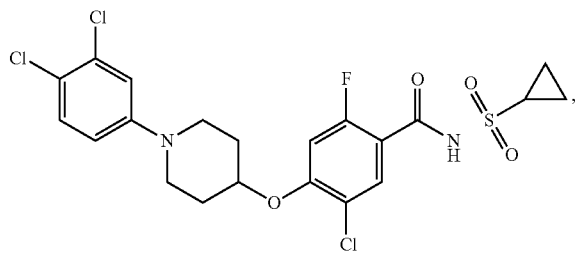
Z-119
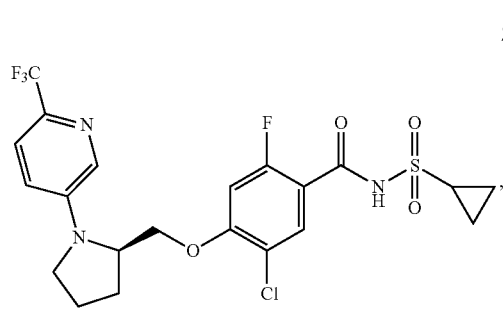
Z-125
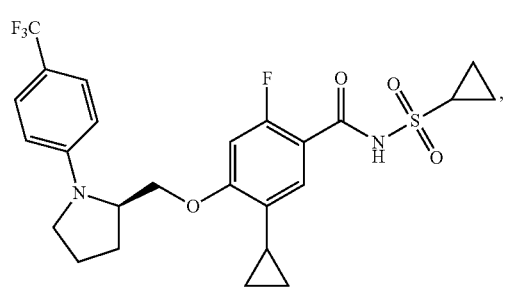
-continued
Z-142
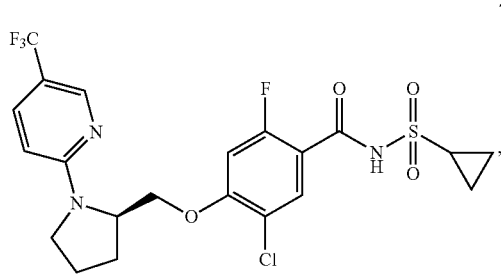
Z-150
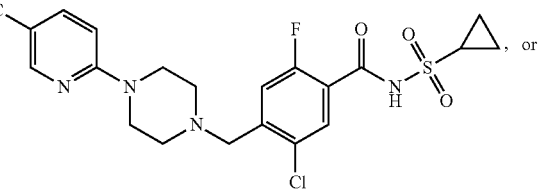
Z-159
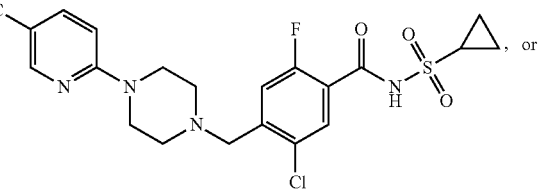
Z-164
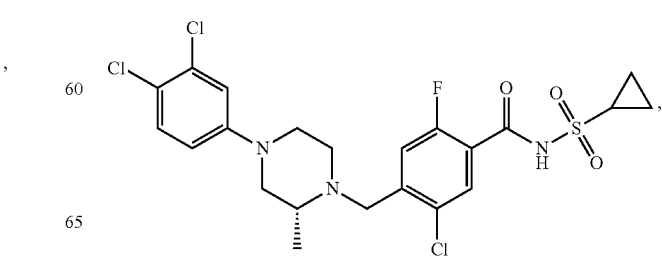
In another preferred example, the compound is selected from the group consisting of:
Z-172

-continued

Z-173

Z-174

Z-175

Z-176

Z-177

Z-178

Z-179

Z-180

Z-181

Z-182

Z-183

Z-184

Z-185
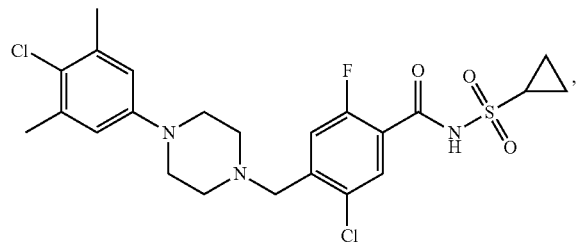
Z-186
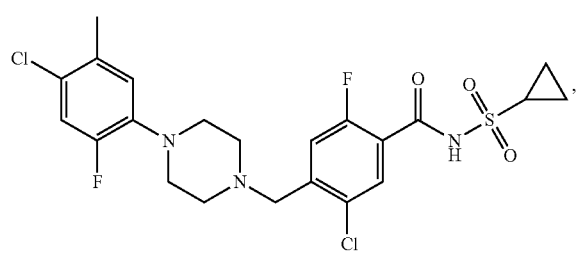
Z-187
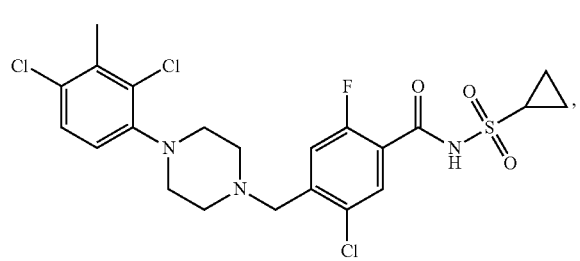
Z-188
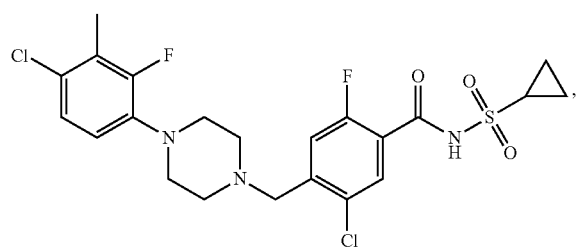
Z-189
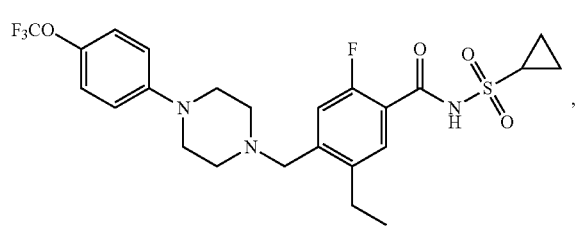
Z-190
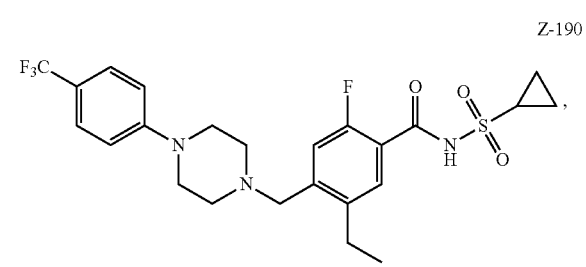
Z-191
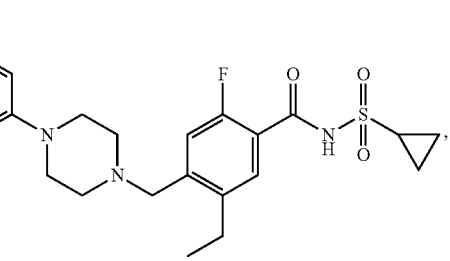
Z-192
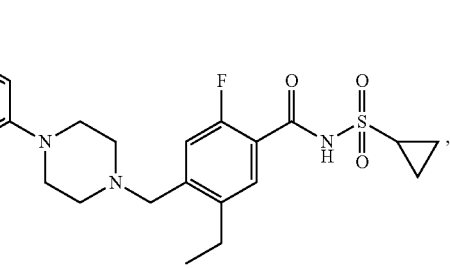
Z-193
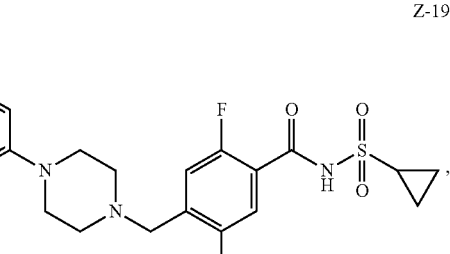
Z-194
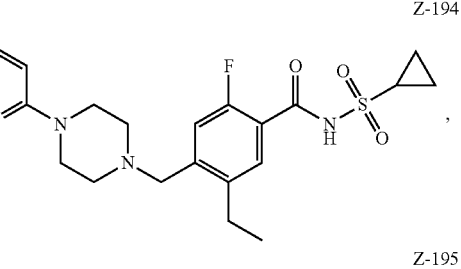
Z-195
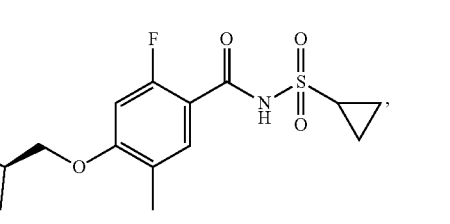
Z-196
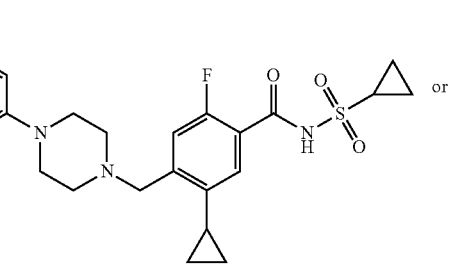 or

Z-197

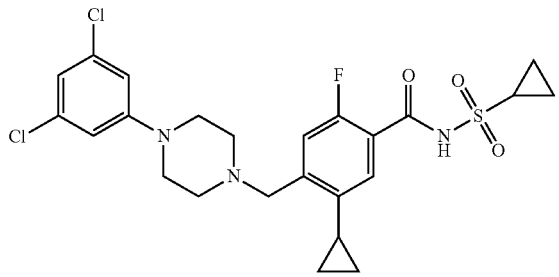

In another preferred example, the $R_1$, $R_2$, $R_3$, $R_4$, $R_5$, $R_6$, $R_a$, $R_b$, $L_1$, $R^y$, $R^x$, $W_1$, $W_2$, n, m, $R_0$, A and the like are each independently the corresponding group in each specific compound of formula II in the examples.

In another preferred example, the compounds of formula II of this invention are the specific compounds prepared in the examples, especially any one of Z-80 to Z-197.

In another preferred example, the compound is a compound prepared in the examples of this application.

In the second aspect of the present invention, a pharmaceutical composition comprising a compound of the first aspect of the invention, or a pharmaceutically acceptable salt, solvate, stereoisomer or prodrug thereof; and a pharmaceutically acceptable carrier is provided.

In the third aspect of the present invention, a use of a compound of the first aspect of the present invention, or a pharmaceutically acceptable salt, solvate, stereoisomer or prodrug thereof, or a pharmaceutical composition of the second aspect of the invention for the manufacture of a medicament for the treatment of a disease or disorder is provided.

In another preferred example, the disease or disorder is selected from the group consisting of pain, depression, cardiovascular disease, respiratory disease, mental illness or a combination thereof.

In another preferred example, the disease or disorder is selected from the group consisting of HIV-related pain, HIV treatment-induced neuropathy, prosopalgia, post-herpetic neuralgia, acute pain, heat-sensitivity, sarcoidosis, irritable bowel syndrome, Crohn's disease, pain associated with multiple sclerosis (MS), amyotrophic lateral sclerosis (ALS), diabetic neuropathy, peripheral neuropathy, arthritis, rheumatoid arthritis, osteoarthritis, atherosclerosis, dystonia, myasthenia syndrome, myotonia, hyperpyrexia, cystic fibrosis, pseudogalonism, rhabdomyolysis, hypothyroidism, bipolar depression, anxiety, schizophrenia, sodium channel toxins related disorders, familial erythromelalgia, primary erythromelalgia, familial rectal pain, cancer, epilepsy, partial and generalized tonic attacks, restless legs syndrome, arrhythmia, fibromyalgia, neuroprotection, tachyarrhythmia, atrial fibrillation and ventricular fibrillation in ischemic disease conditions caused by stroke or nerve injury.

In another preferred example, the pain is selected from the group consisting of neuropathic pain, inflammatory pain, visceral pain, cancer pain, chemotherapeutic pain, traumatic pain, surgical pain, postoperative pain, production pain, labor pain, toothache, chronic pain, persistent pain, peripherally mediated pain, centrally mediated pain, chronic headache, migraine, sinus headache, tension headache, phantom limb pain, peripheral nerve injury, prosopalgia, postherpetic neuralgia, acute pain, familial erythromelalgia, primary erythromelagia, familial rectal pain or fibromyalgia or a combination thereof.

In the fourth aspect of the present invention, a method of treating a disease or disorder in a mammal is provided, comprising administering to a subject (such as a mammal) in need thereof a therapeutically effective amount of the compound of the first aspect of the invention, or a pharmaceutically acceptable salt, solvate, stereoisomer or prodrug thereof, or the pharmaceutical composition of the second aspect of the invention.

It should be understood that each of the above technical features of the invention and each technical feature specifically described below (such as in Examples) can be combined with each other within the scope of the present invention so as to constitute new or preferred technical solutions which need not be specified again herein.

DETAILED DESCRIPTION OF THE EMBODIMENT

Figure 1:
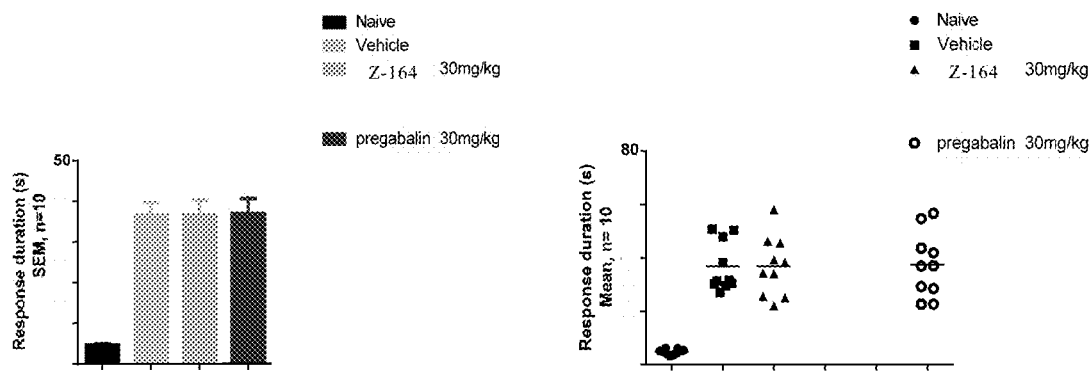
FIG. 1 shows the test baseline of cold allodynic of compound Z-164 in SNL rats model.

After an intensive and in-depth study, inventors unexpectedly discovered that the heterocycle substituted N-sulfonylbenzamide derivatives of the present invention are highly selective to Nav1.7 sodium ion channels, have stable metabolic stability of liver microsomes, and show significant analgesic effects in the pain model test, therefore the series of compounds of the present invention can be developed into drugs for the treatment of a wide range of pains. Based on this, the inventors completed the present invention.

Definition of Terms

As used herein, "$C_{1-20}$ alkyl" refers to a straight and branched saturated aliphatic hydrocarbyl containing 1 to 20 carbon atoms, and the following definition is similar; more preferred is $C_{1-10}$ alkyl, non-limiting examples include methyl, ethyl, n-propyl, isopropyl, n-butyl, isobutyl, t-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof; more preferably $C_{1-6}$ alkyl; and the most preferably $C_{1-3}$ alkyl.

As used herein, "alkenyl" refers to an aliphatic hydrocarbyl as defined above consisting of at least two carbon atoms and at least one carbon-carbon double bond, and "$C_{2-20}$ alkenyl" refers to a straight and branched alkenyl containing 2 to 20 carbon atoms, the following definition is similar; more preferably $C_{2-10}$ alkenyl; more preferably $C_{2-6}$ alkenyl; the most preferably $C_{2-4}$ alkenyl, such as vinyl, 1-propenyl, 2-propenyl, 1-, 2- or 3-butenyl and the like.

As used herein, "alkynyl" refers to an aliphatic hydrocarbyl as defined above consisting of at least two carbon atoms and at least one carbon-carbon triple bond, and "$C_{2-20}$ alkynyl" refers to a straight and branched alkynyl containing 2 to 20 carbon atoms, the following definition is similar; more preferably $C_{2-10}$ alkynyl; more preferably $C_{2-6}$ alkynyl; more preferably $C_{2-4}$ alkynyl; for example, ethynyl, 1-propynyl, 2-propynyl, 1-, 2- or 3-butynyl and the like.

As used herein, "cycloalkyl" refers to a saturated or partially unsaturated monocyclic or polycyclic cyclic hydrocarbyl, "$C_{3-20}$ cycloalkyl" refers to a cyclic hydrocarbyl containing 3 to 20 carbon atoms, and the following definition is similar; more preferably $C_{3-10}$ cycloalkyl; more preferably $C_{3-8}$ cycloalkyl; the most preferably $C_{3-6}$ cycloalkyl. Non-limiting examples of monocyclic cycloalkyl include cyclopropyl, cyclobutyl, cyclopentyl, cyclopentyl, cyclohexenyl, cyclohexadienyl, cycloheptyl, cycloheptatrienyl, cyclooctyl, adamantyl and the like, preferably cyclopropyl, cyclopentyl, cyclohexenyl. Non-limiting examples of polycyclic cycloalkyl include spiro, fused and bridged cycloalkyl.

As used herein, "heterocycloalkyl" and "heterocyclyl" can be used interchangeably and refer to a saturated or partially unsaturated monocyclic or polycyclic cyclic hydrocarbyl, preferably a 3 to 20 membered heterocycloalkyl (a heterocycloalkyl containing 3 to 20 ring atoms, wherein one or more ring atoms are selected from nitrogen, oxygen or $S(O)_t$ (wherein t is an integer from 0 to 2) heteroatoms, but not include —O—O—, —O—S— or —S—S— part of ring, and the rest ring atoms are carbon); more preferably a 3 to 10 membered heterocycloalkyl, wherein 1 to 3 ring atoms are heteroatoms; more preferably a 3 to 6 membered heterocycloalkyl; more preferably a 5 to 6 membered heterocycloalkyl. Non-limiting examples of monocyclic heterocyclyl include pyrrolidinyl, piperidinyl, piperazinyl, morpholinyl, thiomorpholinyl, homopiperazine, pyranyl, tetrahydrofuryl, etc. Non-limiting examples of polycyclic heterocyclyl include spiro, fused and bridged heterocyclyl.

As used herein, "partially unsaturated" refers to a 7 electron system that contains one or more unsaturated bonds but does not have complete conjugation.

As used herein, "$C_{1-20}$ alkoxy" refers to —O—($C_{1-20}$ alkyl), wherein the alkyl is defined as above. $C_{1-10}$ alkoxy is preferred, $C_{1-6}$ alkoxy is more preferred, and $C_{1-3}$ alkoxy is the most preferred. Non-limiting examples include methoxy, ethoxy, propoxy, isopropoxy, butoxy, tert-butoxy, isobutoxy, pentoxy and the like.

As used herein, "$C_{3-20}$ cycloalkoxy" refers to —O—($C_{3-20}$ cycloalkyl), wherein the cycloalkyl is defined as above, preferably $C_{3-10}$ cycloalkoxy, preferably $C_{3-8}$ cycloalkoxy, more preferably $C_{3-6}$ cycloalkoxy, and non-limiting examples include cyclopropyloxy, cyclobutyloxy, cyclopentyloxy, cyclohexyloxy and the like.

As used herein, "$C_{6-20}$ aryl" refers to a full-carbon monocyclic or fused polycyclic group (i.e., rings that share adjacent carbon atoms pairs) having a conjugated π-electron system, and refers to an aryl containing 6 to 20 carbon atoms; more preferably $C_{6-12}$ aryl, more preferably phenyl and naphthyl, and the most preferably phenyl.

As used herein, "a bond" refers to a covalent bond through which two groups are attached.

As used herein, "halogen" refers to fluorine, chlorine, bromine or iodine.

As used herein, "halogenated" means that one or more (e.g., 1, 2, 3, 4, or 5) hydrogens in a group are substituted by a halogen(s).

For example, "halogenated $C_{1-20}$ alkyl" means that the alkyl is substituted by one or more (e.g., 1, 2, 3, 4, or 5) halogens, wherein the alkyl is defined as above. Halogenated $C_{1-10}$ alkyl is more preferred, halogenated $C_{1-6}$ alkyl is more preferred, and halogenated $C_{1-3}$ alkyl is the most preferred. Examples of halogenated $C_{1-20}$ alkyl include, but not limited to, monochloroethyl, dichloromethyl, 1,2-dichloroethyl, monobromoethyl, monofluoroethyl, monofluoromethyl, difluoromethyl, trifluoromethyl and the like.

For example, "halogenated $C_{1-20}$ alkoxy" means that the alkoxy is substituted by one or more (e.g., 1, 2, 3, 4 or 5) halogens, wherein the alkoxy is defined as above. Halogenated $C_{1-10}$ alkoxy is preferred, halogenated $C_{1-6}$ alkoxy is more preferred, and halogenated $C_{1-3}$ alkoxy is the most preferred. Examples include but not limited to trifluoromethoxy, trifluoroethoxy, monofluoromethoxy, monofluoroethoxy, difluoromethoxy, difluoroethoxy and the like.

For example, "halogenated $C_{3-20}$ cycloalkyl" means that the cycloalkyl is substituted by one or more (e.g., 1, 2, 3, 4 or 5) halogens and the cycloalkyl is defined as above. Halogenated $C_{3-10}$ cycloalkyl is preferred, halogenated $C_{3-8}$ cycloalkyl is more preferred, and halogenated $C_{3-6}$ cycloalkyl is the most preferred, including, but not limited to trifluorocyclopropyl, monofluorocyclopropyl, monofluorocyclohexyl, difluorocyclopropyl, difluorocyclohexyl and the like.

As used herein, "deuterated $C_{1-20}$ alkyl" means that the alkyl is substituted by one or more (e.g., 1, 2, 3, 4, or 5) deuterium atoms, wherein the alkyl group is defined as above. Deuterated $C_{1-10}$ alkyl is preferred, deuterated $C_{1-6}$ alkyl is more preferred, and deuterated $C_{1-3}$ alkyl is the most preferred. Examples of deuterated $C_{1-20}$ alkyl include, but not limited to, mono-deuterated methyl, mono-deuterated ethyl, di-deuterated methyl, dideuterated ethyl, tri-deuterated methyl, tri-deuterated ethyl and the like.

As used herein, "$C_{1-20}$ hydroxyalkyl" refers to a $C_{1-20}$ alkyl substituted by hydroxy, wherein the alkyl is defined as above. $C_{1-10}$ hydroxyalkyl is preferred, $C_{1-6}$ hydroxyalkyl is more preferred, and $C_{1-3}$ hydroxyalkyl is the most preferred.

As used herein, "amino" refers to —NH$_2$, "cyano" refers to —CN, "nitro" refers to —NO$_2$, "benzyl" refers to —CH$_2$-phenyl, "oxo" refers to =O, "carboxyl" refers to —C(O)OH, "thiol" refers to —SH, and the structure of "cyclopropylidene" is:

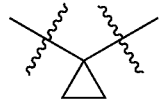

As used herein, "carboxylate" refers to —C(O)O—($C_{1-20}$ alkyl) or ($C_{3-20}$ cycloalkyl), wherein the alkyl and cycloalkyl are defined as above.

As used herein, "$C_{1-20}$ alkylthio" refers to —S—($C_{1-20}$ alkyl), wherein the alkyl group is defined as above. $C_{1-10}$ alkylthio is preferred, $C_{1-6}$ alkylthio is more preferred, and $C_{1-3}$ alkylthio is the most preferred.

As used herein, "$C_{1-20}$ alkylamino" refers to —($C_{1-20}$ alkyl)-NH$_2$ or —NH$_2$—($C_{1-20}$ alkyl), wherein the alkyl is defined as above. $C_{1-10}$ alkylamino is preferred, $C_{1-6}$ alkylamino is more preferred, and $C_{1-3}$ alkylamino is the most preferred.

As used herein, "$C_{3-20}$ cycloalkylthio" refers to —S—($C_{3-20}$ cycloalkyl), wherein the cycloalkyl is defined as above. $C_{3-10}$ cycloalkylthio is preferred, $C_{3-8}$ cycloalkylthio is more preferred, and $C_{3-6}$ cycloalkylthio is the most preferred.

As used herein, "3 to 20 membered heterocycloalkylthio" refers to —S-(3 to 20 membered heterocycloalkyl), wherein the heterocycloalkyl is defined as above. 3 to 10 membered heterocycloalkylthio is preferred.

As used herein, "3 to 20 membered heterocycloalkyloxy" refers to —O-(3 to 20 membered heterocycloalkyl), wherein the heterocycloalkyl is defined as above. 3 to 10 membered heterocycloalkyloxy is preferred.

As used herein, "heteroaryl ring" and "heteroaryl" can be used interchangeably and refer to a group that has 5 to 10 ring atoms, preferably 5 or 6 membered monocyclic heteroaryl or 8 to 10 membered bicyclic heteroaryl; shares 6, 10 or 14π electrons in the ring array, and has 1 to 5 heteroatoms in addition to carbon atoms. "Heteroatom" refers to nitrogen, oxygen or sulfur.

As used herein, "3 to 7 membered monocyclic ring" refers to a saturated or partially unsaturated full carbon monocyclic ring containing 3 to 7 ring atoms, preferably 5 to 6 membered. Examples of monocyclic rings include, but not limited to cyclopropyl ring, cyclobutyl ring, cyclopentyl ring, cyclopentenyl ring, cyclohexyl ring, cyclohexenyl ring, cyclohexadienyl ring, cycloheptyl ring, cycloheptatrienyl ring, cyclooctyl ring and the like.

As used herein, "3 to 7 membered mono heterocyclic ring" means that 1, 2 or 3 carbon atoms in a 3 to 7 membered monocyclic ring are replaced by a heteroatom selected from nitrogen, oxygen or sulfur, preferably 5 to 6 membered. Examples of mono heterocyclic ring include, but not limited to, tetrahydrofuran ring, tetrahydrothiophene ring, pyrrolidinyl ring, piperidine ring, pyrroline ring, oxazolidine ring, piperazine ring, dioxolane, morpholine ring, thiomorpholine ring, homopiperazine ring, pyran ring and the like.

As used herein, "8 to 10 membered bicyclic ring" refers to a saturated full carbon bicyclic ring or partially unsaturated full carbon bicyclic ring having 8 to 10 ring atoms, examples of bicyclic ring include, but not limited to,

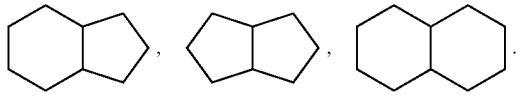

As used herein, "8 to 10 membered bis-heterocyclic ring" means that 1, 2, 3, 4, or 5 carbon atoms in an 8 to 10 membered bicyclic ring are replaced by a heteroatom selected from nitrogen, oxygen or sulfur. Examples of bis-heterocyclic ring include, but not limited to, tetrahydroquinoline ring, tetrahydroisoquinoline ring, decahydroquinoline ring and the like.

As used herein, "5 to 6 membered monocyclic heteroaryl ring" refers to a mono-heteroaryl ring containing 5 to 6 ring atoms, for example including, but not limited to thiophene ring, N-alkylpyrrole ring, furan ring, thiazole ring, imidazole ring, oxazole ring, pyrrole ring, pyrazole ring, triazole ring, tetrazole ring, isoxazole ring, oxadiazole ring, thiadiazole ring, pyridine ring, pyridazine ring, pyrimidine ring, pyrazine ring and the like.

As used herein, "8 to 10 membered bicyclic heteroaryl ring" refers to a bicyclic heteroaryl ring containing 8 to 10 ring atoms, for example including, but not limited to benzofuran ring, benzothiophene ring, indole ring, isoindole ring, quinoline ring, isoquinoline ring, indazole ring, benzothiazole ring, benzimidazole ring, quinazoline ring, quinoxaline ring, cinnoline ring and phthalazine ring.

As used herein, "benzo 3-7 membered monocyclic ring or benzo 3-7 membered mono heterocyclic ring" means a monocyclic or monoheterocyclic ring containing 3 to 7 ring atoms is fused to a benzene ring to form a bicyclic ring structure, preferably benzo 5 to 6 membered monocyclic ring or benzo 5 to 6 membered monoheterocyclic ring. Non-limiting examples include:

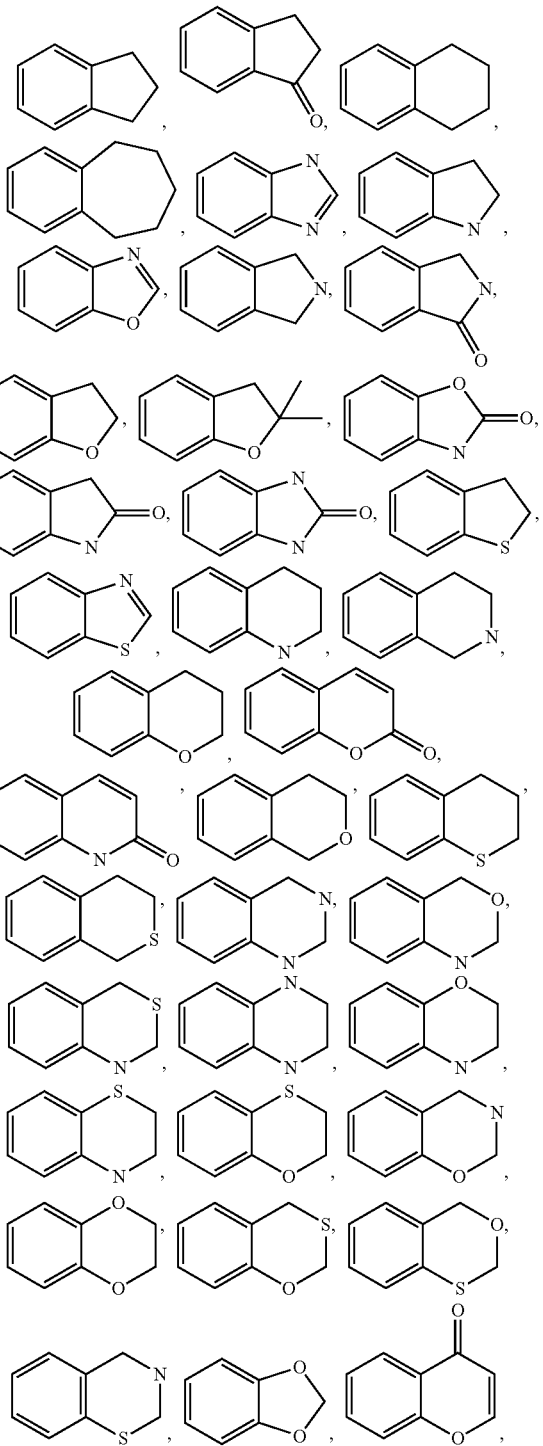

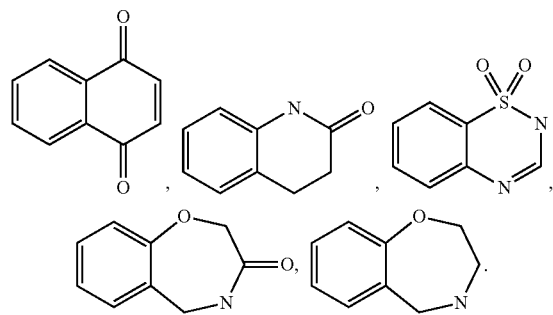

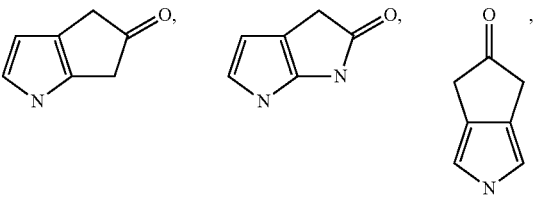

As used herein, "condensed ring of 5-6 membered monocyclic heteroaryl ring and 3-7 membered monocyclic ring or condensed ring of 5-6 membered monocyclic heteroaryl ring and 3-7 membered mono heterocyclic ring" means a 3 to 7 membered monocyclic ring or 3 to 7 membered monoheterocyclic ring is fused to a 5 to 6 membered monocyclic heteroaryl ring to form a bicyclic ring structure, non-limiting examples including:

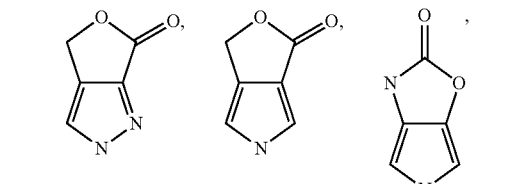

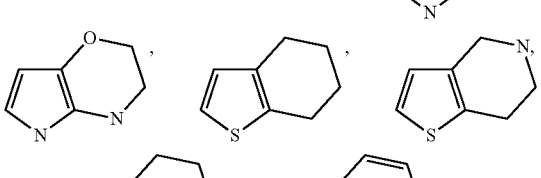

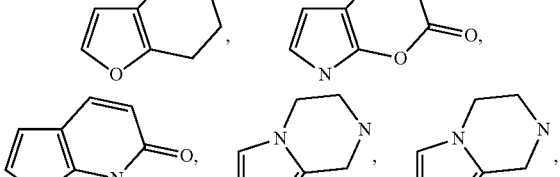

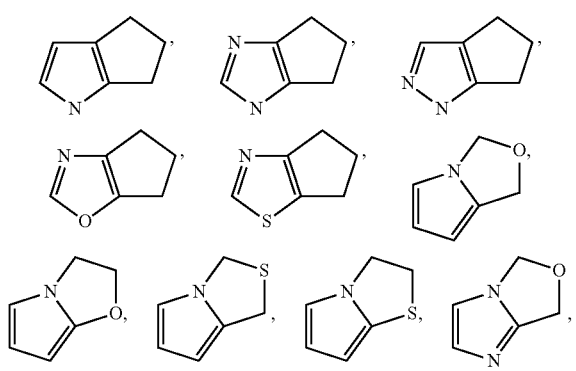

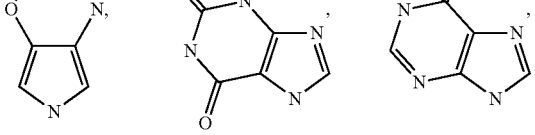

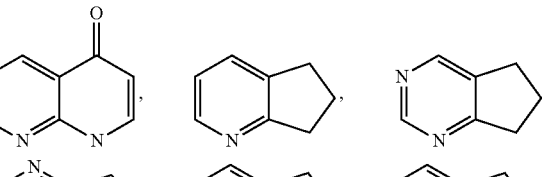

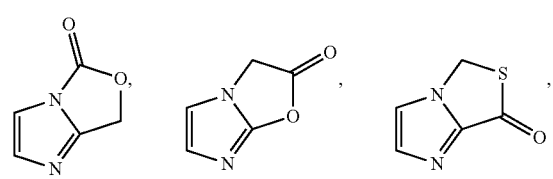

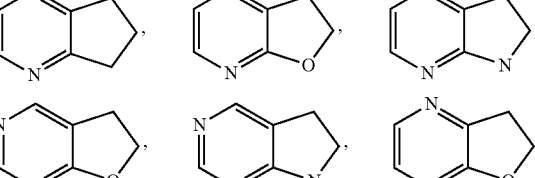

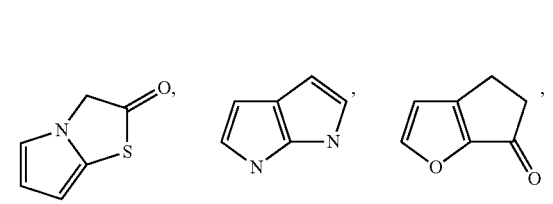

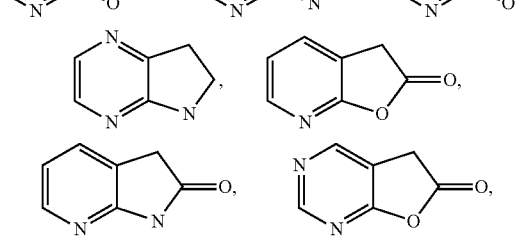

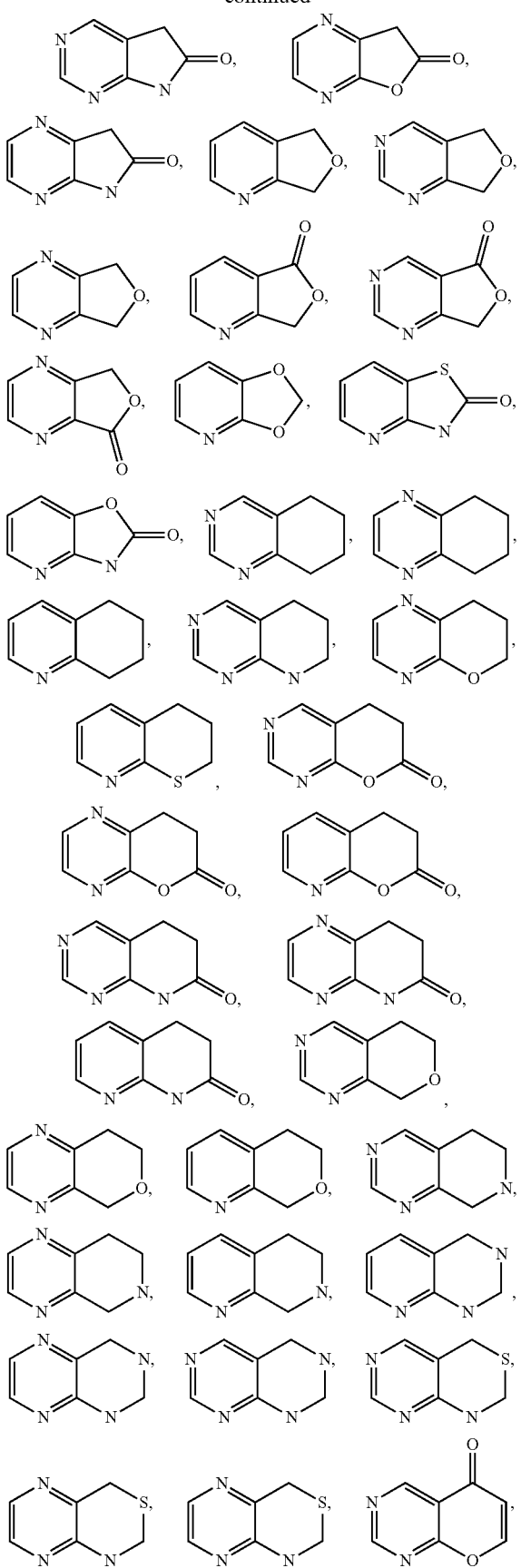

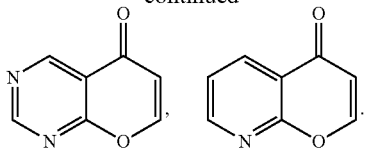

As used herein, "substituted" means one or more hydrogen atoms in a group, preferably 1 to 5 hydrogen atoms, are each independently substituted by the corresponding number of substituents. More preferably, 1 to 3 hydrogen atoms are each independently substituted by the corresponding number of substituents. It is obvious that substituents are only in their possible chemical positions, and those skilled in the art can, without any undue effort, determine (by experiment or theory) that it is possible or impossible. For example, an amino or hydroxyl with free hydrogen may be unstable when combined with a carbon atom having an unsaturated (such as olefinic) bond.

As used herein, alkyl may be substituted or unsubstituted, alkenyl may be substituted or unsubstituted, alkynyl may be substituted or unsubstituted, cycloalkyl may be substituted or unsubstituted, heterocyclic ring may be substituted or unsubstituted, alkoxy may be optionally substituted or unsubstituted, cycloalkoxy may be optionally substituted or unsubstituted, aryl may be substituted or unsubstituted, and 3 to 7 membered monocyclic ring may be substituted or unsubstituted, 3 to 7 membered mono heterocyclic ring may be substituted or unsubstituted, 8 to 10 membered bicyclic ring may be substituted or unsubstituted, and 8 to 10 membered bis-heterocyclic ring may be substituted or unsubstituted, and benzo 3-7 membered monocyclic ring or benzo 3-7 membered monocyclic ring may be substituted or unsubstituted and the condensed ring of 5-6 membered monocyclic heteroaryl ring and 3-7 membered monocyclic ring or condensed ring of 5-6 membered monocyclic heteroaryl ring and 3-7 membered mono heterocyclic ring may be substituted or unsubstituted, when the above groups are substituted, the substituent is preferably 1 to 5 groups independently selected from the group consisting of $C_{1-20}$ alkyl, halogenated $C_{1-20}$ alkyl, $C_{2-20}$ alkenyl, $C_{2-20}$ alkynyl, $C_{1-20}$ alkoxy, $C_{1-20}$ alkylthio, $C_{1-20}$ alkylamino, halogen, thiol, hydroxyl, nitro, cyano, $C_{3-20}$ cycloalkyl, 3 to 20 membered heterocyclic ring, $C_{6-20}$ aryl, 5 or 6 membered monocyclic heteroaryl or 8 to 10 membered bicyclic heteroaryl, $C_{3-20}$ cycloalkoxy, 3 to 20 membered heterocycloalkyloxy, $C_{3-20}$ cycloalkylthio, 3 to 20 membered heterocycloalkylthio, oxo, amino, $C_{1-20}$ hydroxyalkyl, carboxyl or carboxylate.

Preparation Method

The present invention provides a method for the preparation of compounds of formula (I), which can be readily prepared by a variety of synthetic procedures well known to those skilled in the art. The exemplary preparation methods for these compounds may include (but not limited to) the following processes.

The compound of formula (I) of the present invention can be prepared according to the following synthetic route, and the steps in the method may be extended or combined as needed during the specific operation.

Route 1

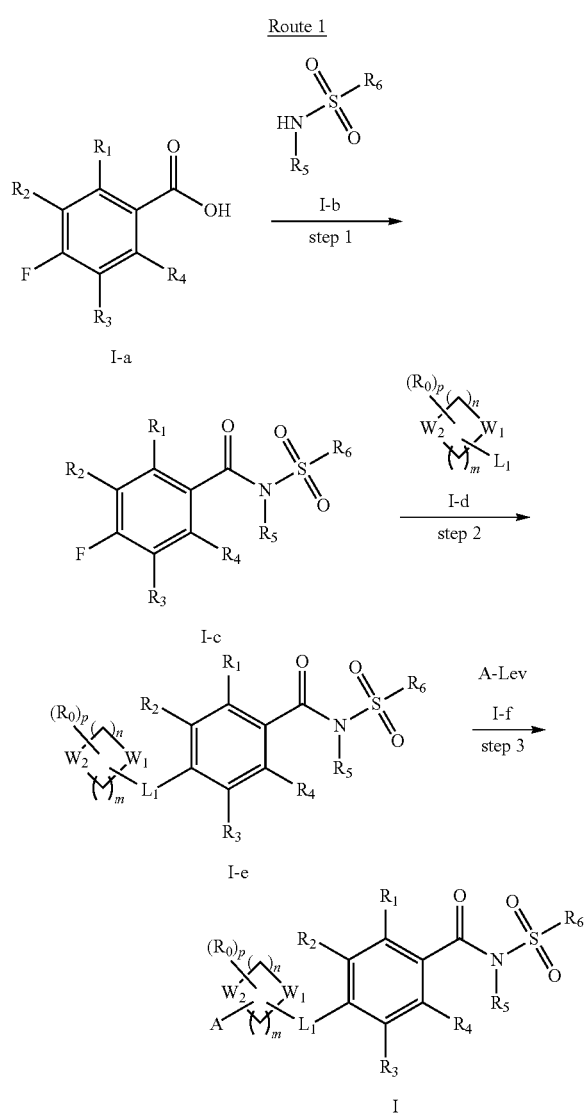

Route 2

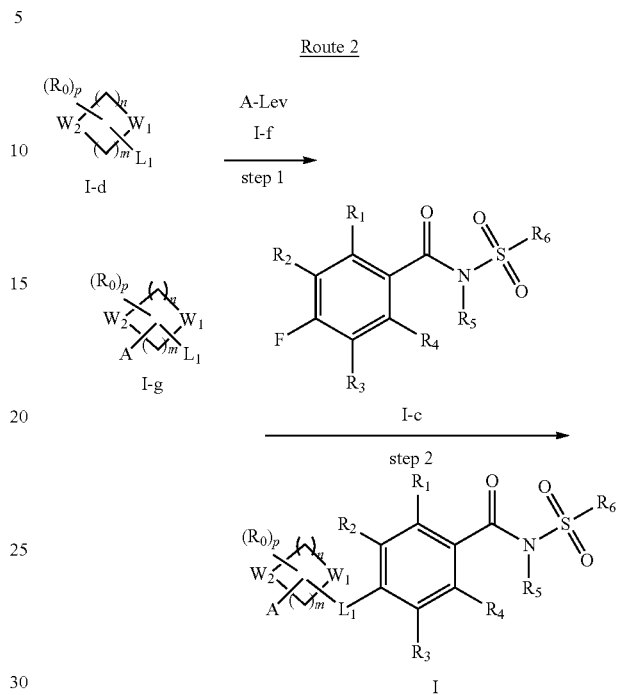

groups such as methanesulfonate, tosylate, bromobenzenesulfonate, p-toluenesulfonate and the like; acyloxy groups such as acetoxy, trifluoroacetoxy and the like.

The compound of formula (I-d) can first undergo a substitution reaction with a compound of formula (I-f) to produce a compound of formula (I-g), followed by a reaction with a compound of formula (I-c) to produce a compound of formula (I), and the reaction conditions are the same as step 3 and step 2 in route 1 respectively.

The reactions in each of the above steps are conventional reactions known to those skilled in the art. Unless otherwise specified, reagents and starting compounds used in the synthetic routes are commercially available or can be prepared by one skilled in the art based on the different compounds structure designed according to known methods.

Compared with the prior art, the main advantages of the present invention are:

A series of novel heterocycle substituted N-sulfonylbenzamide derivatives are provided which are highly selective to Nav1.7 sodium ion channels and have stable metabolic stability of liver microsomes, and can be used as a medicine for a wide range of pain treatments.

The present invention will be further illustrated below with reference to the specific examples. It should be understood that these examples are only to illustrate the invention but not to limit the disclosure of the invention. The experimental methods without specific conditions in the following embodiments are generally carried out according to conventional conditions, or in accordance with the conditions recommended by the manufacturer. Unless indicated otherwise, parts and percentage are calculated by weight. Unless otherwise defined, terms used herein are of the same meanings that are familiar to those skilled in the art. In addition, any methods and materials similar with or equivalent to those described herein can be applied to the present invention.

As used herein, DMF refers to dimethylformamide, DMSO refers to dimethylsulfoxide, THF refers to tetrahy- Step 1: The carboxyl in the compound of formula (I-a) may be firstly activated by a reagent such as oxalyl chloride, carbonyldiimidazole (CDI), propylphosphonic anhydride, urea-based amide coupling reagent or carbodiimide, and subsequently undergo displacement reaction with sulfamide groups in compounds of formula (I-b) to produce a compound of formula (I-c) in the presence of a nucleophilic base such as 4-dimethylaminopyridine, N, N-dimethyl aminopropyl-N'-ethylcarbodiimide, 4-dimethylaminopyridine/N,N-diisopropylethylamine.

Step 2: The compound of formula (I-e) is prepared through a substitution reaction (for example nucleophilic substitution reaction and the like) or a coupling reaction (for example Suzuki coupling and the like) of the compound of formula (I-c) and compound of formula (I-d) in the presence of a base system, and suitable base system includes potassium tert-butoxide in DMSO, sodium hydride in DMF, potassium carbonate in DMF and the like.

Step 3: The compound of formula (I-e) can undergo a substitution reaction with a compound of formula (I-f) to produce a compound of formula (I), the Lev in formula (I-f) is a leaving group, including but not limited to trifluoromethanesulfonate; chlorine, bromine, iodine; sulfonate drofuran, DIEA refers to N,N-diisopropylethylamine, EA refers to ethyl acetate, PE refers to petroleum ether. BINAP refers to (2R,3S)-2,2'-bis diphenylphosphino-1,1'-binaphthyl, LiHMDS refers to lithium bistrimethylsilylamide, THF refers to tetrahydrofuran, HATU refers to 2-(7-azobenzotriazole)-N,N,N', N'-tetramethyluronium hexafluorophosphate, n-BuLi refers to n-butyllithium, DCM refers to dichloromethane, DME refers to ethylene glycol dimethyl ether, NBS refers to N-bromosuccinimide, Pd2(dba)3 refers to tris(dibenzylideneacetone)dipalladium, CDI refers to N, N'-carbonyldiimidazole, DBU refers to 1,5-diazabicyclo [5.4.0]undec-5-ene, Pd(dppf)Cl2 refers to [1,1'-bis(diphenylphosphino)ferrocene]palladium dichloride, DIAD refers to diisopropyl azodicarboxylate, EDCI refers to 1-(3-dimethylaminopropyl)-3-ethylcarbodiimide hydrochloride, DMAP refers to 4-dimethylaminopyridine, and LDA refers to lithium diisopropylamide.

As used herein, room temperature refers to about 25° C.

Preparation of Compound 13-a:

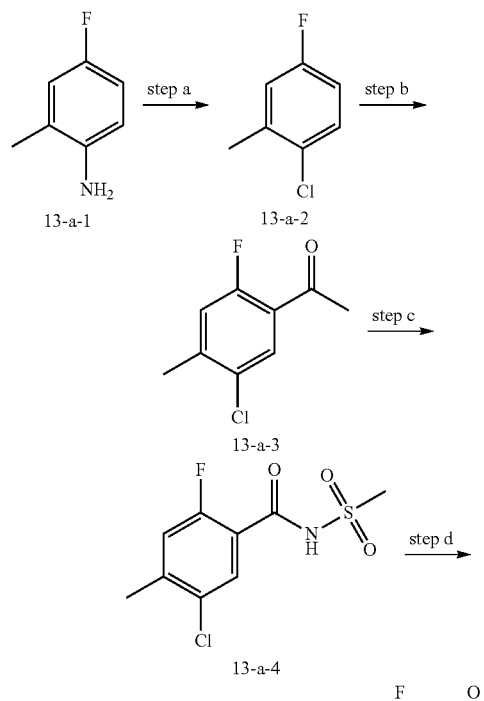

Step a: Compound 13-a-1 (50 g, 0.40 mol) was added to concentrated hydrochloric acid (400 ml), the mixture was cooled to 0° C., and a solution of sodium nitrite (28.6 g, 0.44 mol) in water was added dropwise. After the mixture reacted at 0° C. for 0.5 h, cuprous chloride (91.68 g, 0.48 mol) was added. The mixture was stirred at room temperature for 0.5 h, then heated to 100° C. and stirred for 1 h, cooled and filtered. The filtrate was extracted with petroleum ether (500 ml×2), and the organic phase was washed with saturated brine (500 ml), dried over anhydrous sodium sulfate and filtered. The filtrate was evaporated to dryness under reduced pressure, and the resulting crude product was purified by column chromatography (eluent/PE:EA=10:1) to obtain compound 13-a-2 (24.1 g, yield: 41%) as a colorless oil.

Step b: Compound 13-a-2 (18.72 g, 130 mmol) was dissolved in anhydrous THF (200 ml) and cooled to −78° C., and n-BuLi (62.4 ml, 2.4 M/L, 248 mmol) was added dropwise under nitrogen. The mixture was stirred for 1 h at −78° C., and then poured onto dry ice. The mixture was stirred for 1 h at −78° C., and then stirred at room temperature for 1 h. The mixture was poured into 2N aqueous hydrochloric acid (200 ml), and extracted with ethyl acetate (250 ml). The organic phase was separated and washed with brine (200 ml), dried over anhydrous sodium sulfate and filtered, and the filtrate was evaporated by a rotary evaporator to give a white solid 13-a-3 (9.1 g, Yield: 37%). ESI-MS [M−H]⁻: 187. Purity=80% (UV 214).

Step c: Compound 13-a-3 (9.1 g, 48 mmol) was dissolved in dry DCM (150 mL), cooled to 0° C., and 1-ethyl-(3-dimethylaminopropyl)carbodiimide hydrochloride (13.76 g, 72 mmol), DMAP (11.8 g, 96 mmol), methanesulfonamide (9.12 g, 96 mmol), N, N-diisopropylethylamine (18.57 g, 114 mmol) were added separately. The mixture was stirred at room temperature for 18 h and then poured into 2N aqueous hydrochloric acid (100 ml). After the mixture was stirred at room temperature for 0.5 h, the organic phase was separated and washed with brine (100 ml), dried over anhydrous sodium sulfate and filtered, and the filtrate was evaporated by a rotary evaporator to give 13-a-4 (9.6 g, yield 78%) as a white solid. ESI-MS[M+H]⁺: 266.0. Purity=91% (UV 214).

Step d: Compound 13-a-4 (7.95 g, 30 mmol) was dissolved in dry DME (100 ml), NBS (12.21 g, 69 mmol), azodiisobutyronitrile (0.59 g, 3 mmol) were added. The mixture was refluxed for 18 h while stirring, and the filtrate was evaporated by a rotary evaporator. The residue was purified by HPLC column to give 13-a-5 as a white solid (3.1 g, yield 30%). ESI-MS (M+H)⁺: 343.7. Purity=98.2% (UV 214). ¹H NMR (400 MHz, CDCl₃) δ 8.80 (s, 1H), 8.12 (d, J=6.8 Hz, 1H), 7.36 (d, J=12.0 Hz, 1H), 4.54 (s, 2H), 3.43 (s, 3H).

Preparation of Compound 17-a:

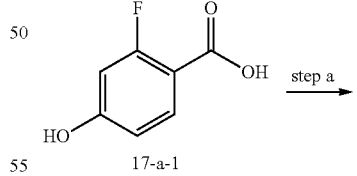

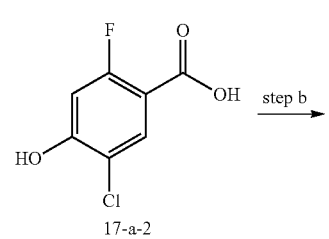

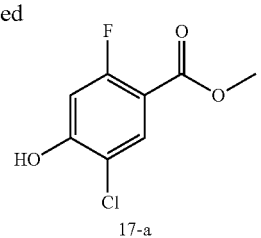

Step a: To a solution of compound 17-a-1 (4.5 g, 28.8 mmol), p-toluenesulfonic acid (499 mg, 2.9 mmol) in dichloromethane (100 ml) was slowly added n-chlorosuccinimide (4 g, 30.3 mmol) at 0° C., stirred for 2 hours and stirred at room temperature overnight. The reaction was completed, poured into water, extracted with ethyl acetate, dried over anhydrous sodium sulfate, filtered and the filtrate was concentrated under reduced pressure to give 17-a-2 (5 g). MS m/z(ESI): 189[M−H]−.

Step b: To a solution of compound 17-a-2 (5 g, 26.3 mmol) in methanol (130 ml) was added concentrated sulfuric acid (7 ml, 1 mmol) dropwise, and the mixture was stirred for 5 hours under reflux. The reaction was completed, cooled to room temperature, poured into water, extracted with ethyl acetate, dried over anhydrous sodium sulfate, filtered and the filtrate was concentrated under reduced pressure. Dichloromethane was added and stirred for 20 minutes at room temperature, filtered to obtain compound 17-a (4.2 g) as a white solid. MS m/z(ESI): 203[M−H]−.

Preparation of Compound 22-a:

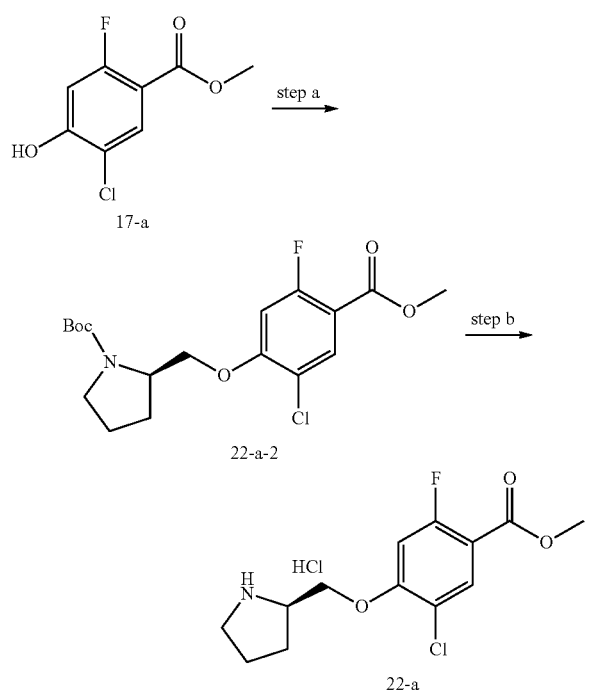

Step a: Compound 22-a-2 (552 mg) was obtained according to the preparation method of step 3 in Example 57 using compound 17-a (2 g) as a starting material, except that the reaction condition was changed to stirring overnight at room temperature. Purity 96.57%, yield 14%, MS m/z(ESI): 322.1 [M+H−56]+.

Step b: Compound 22-a (409 mg) was obtained according to the preparation method of step 1 in Example 4 using compound 22-a-2 (552 mg) as a starting material. Purity 100%, yield 41%, MS m/z(ESI): 288[M+H]+.

Preparation of Compound 25-a:

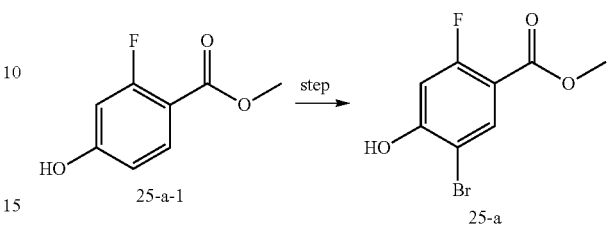

Step: To a solution of compound 25-a-1 (2.03 g, 11.93 mmol) in acetic acid (65 ml) was added bromine (0.61 ml, 11.33 mmol), stirred at room temperature overnight. The reaction was completed, concentrated under reduced pressure, washed with brine and extracted with ethyl acetate, and the organic phase was separated, dried and concentrated under reduced pressure to obtain the crude product which was purified by combi-flash column chromatography to obtain compound 25-a (3 g), purity 85%, yield 100%. MS m/z(ESI): 249[M+H]+.

Preparation of Compound 36-a:

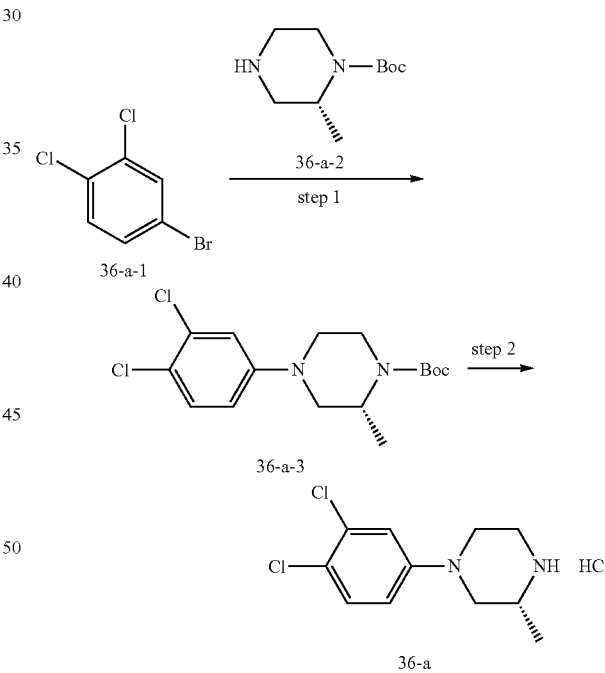

Step 1: To a 50 ml sealed tube were added compound 36-a-1 (500 mg, 2.23 mmol), compound 36-a-2 (671 mg, 3.35 mmol), Pd$_2$(dba)$_3$(tris(dibenzylideneacetone)dipalladium) (41 mg, 0.045 mmol), BINAP ((±)-2,2'-bis-(diphenylphosphino)-1,1'-binaphthyl), potassium butoxide (644 mg, 6.7 mmol), 7 ml of 1,4-dioxane, and stirred for 2 h at 90° C. After the reaction was completed, the mixture was cooled to room temperature, 30 ml of water and 30 ml of ethyl acetate were added, filtered and extracted with ethyl acetate, the organic phase was separated and combined, and the filtrate was concentrated under reduced pressure to give the crude product which was purified by combi-flash column chromatography to give the compound 36-a-3 (475 mg) as a yellow oil which was used directly in the next reaction. MS m/z(ESI): 289.1[M+H−56]+.

Step 2: A solution of hydrochloride in methanol (1.5 ml, 5.53 mmol) was added to a solution of compound 36-a-3 (475 mg) in methanol, and stirred at room temperature for 4 hours. The reaction mixture was concentrated to give the crude compound 36-a which was used directly without purification.

Preparation of Compound 37-a:

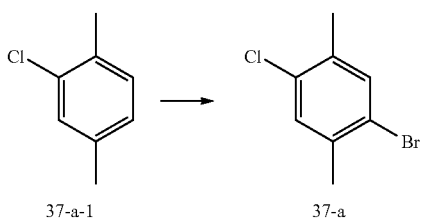

Bromine was added dropwise to a mixed solution of compound 37-a-1 (1.0 g, 7.09 mmol) and iodine (9 mg, 0.035 mmol) in dichloromethane under argon at 0° C. After the addition was completed, the reaction was slowly warmed to room temperature, stirred at room temperature overnight in darkness. The reaction was quenched with sodium bisulfite solution, extracted with dichloromethane, the organic phase was washed with brine, dried and concentrated, and the crude product was recrystallized from ethanol to give white solid 37-a (230 mg), purity 100%, yield 14.7%, MS m/z(ESI): N/A.

Preparation of Compound 38-a:

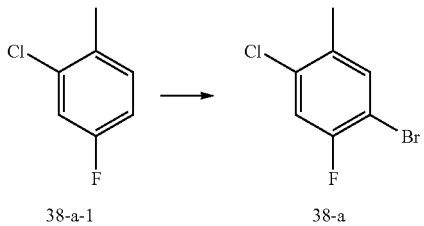

Bromine (2.49 g, 15.59 mmol) was added dropwise to a mixed solution of compound 38-a-1 (2.26 g, 15.59 mmol) and iron powder (44 mg, 0.78 mmol) at 60° C. After the addition was completed, the reaction mixture was stirred continuously at 60° C. for 3 h. The reaction liquid was cooled to room temperature, quenched with sodium bisulfite solution, extracted with petroleum ether and the organic phase was washed with brine, dried and concentrated to give a crude product which was purified by column chromatography (100% petroleum ether) to give compound 38-a (2.82 g) as a colorless oil, purity 75%, yield 81%, MS m/z(ESI): N/A.

Preparation of Compound 39-a:

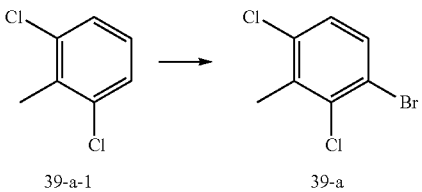

To a mixed solution of compound 39-a-1 (5 g, 31.06 mmol), iron powder (87 mg, 1.55 mmol) and iodine (39 mg, 0.15 mmol) in carbon tetrachloride was added dropwise bromine (5.22 g, 32.61 mmol) at room temperature. After the addition was complete, the reaction solution was stirred at room temperature for two days. The reaction solution was quenched with sodium bisulfite solution, extracted with dichloromethane (2*50 ml), and the organic phase was washed with saturated brine (30 ml), concentrated and dried to give compound 39-a (4.77 g) as a colorless oil directly used in the next reaction, purity 76%, yield 64%, MS m/z(ESI): N/A.

Preparation of Compound 40-a:

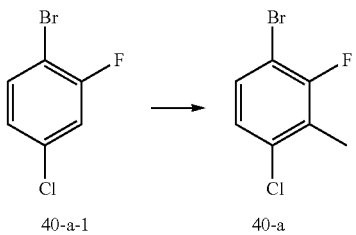

A solution of compound 40-a-1 (1 g, 4.77 mmol) in anhydrous tetrahydrofuran was added dropwise to a solution of LDA (2M, 3 ml) in tetrahydrofuran at −50° C. After the addition was completed, the mixture was stirred for 30 minutes at −50° C. To the above reaction mixture was added methyl iodide (1037 mg, 7.30 mmol) at −50° C. The reaction mixture was then allowed to naturally warm to room temperature, poured into water and extracted with ethyl acetate. The organic phase was washed with saturated brine, dried and concentrated, and the crude product was purified by column chromatography (100% petroleum ether) to give compound 40-a (747 mg) as a colorless oil, purity 77%, yield 70%, MS m/z(ESI): N/A.

Preparation of Compound 41-a:

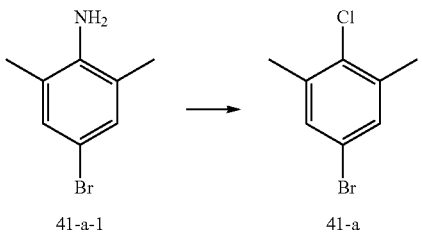

Compound 41-a-1 (500 mg, 2.5 mmol) was dispersed in 5 ml of water, 1 ml of concentrated hydrochloric acid was added and the solution was cooled to 0° C. Sodium nitrite (517 mg, 7.49 mmol) was dissolved in 2 ml of water, and the solution was added dropwise to the above solution at 0° C. and kept stirring at 0° C. for 30 minutes. Cuprous chloride (990 mg, 10.0 mmol) was added, and the reaction solution was heated to 75° C. and stirred for 1 h. After cooled to room temperature, the reaction solution was extracted with ethyl acetate, and the organic phase was washed with brine, dried and concentrated. The crude product was purified by column chromatography (100% petroleum ether) to give compound 41-a as a colorless oil (218 mg) %, purity 89%, yield 40%, MS m/z(ESI): N/A.

Preparation of Compound 42-a:

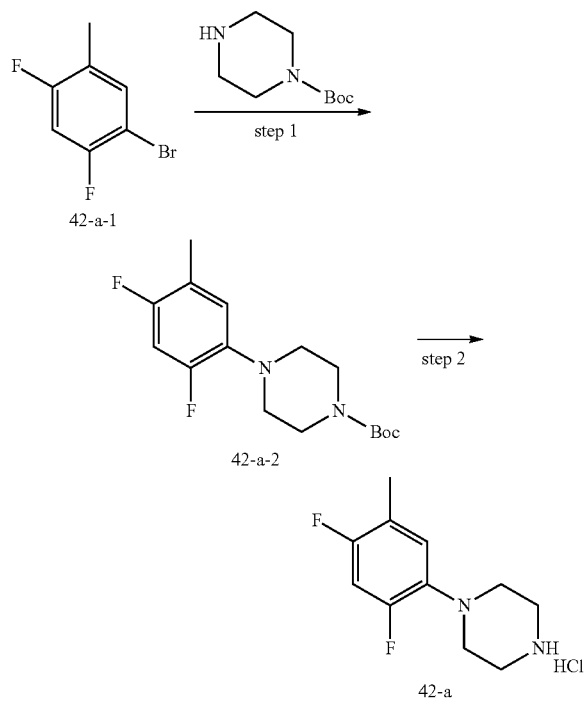

Step 1: A mixed solution of compound 42-a-1 (200 mg, 0.966 mmol), N-Boc-piperazine (270 mg, 1.449 mmol), $Pd_2(dba)_3$ mmol) (44 mg, 0.097 mmol), Johnphos (30 mg, 0.193 mmol), sodium tert-butoxide (280 mg, 2.898 mmol) in dioxane was stirred overnight under argon at 40° C. The reaction solution was cooled to room temperature, filtered through celite and the filtrate was concentrated under reduced pressure. The crude product was purified by column chromatography (PE:EA=10:1) to give compound 42-a-2 (188 mg) as a yellow oil, purity 93%, yield 50%, MS m/z(ESI): 257.2[M+H−56]$^+$.

Step 2: A yellow solid compound 42-a (212 mg) was obtained according to the preparation method of step 2 for intermediate 36-a.

General procedure: compounds 43-a to 60-a are prepared according to the similar method of intermediate 36-a using N-Boc-piperazine and bromine substituted aromatic ring or bromine substituted pyridine as the starting material. Compound 58-a is prepared according to the similar method of 42-a.

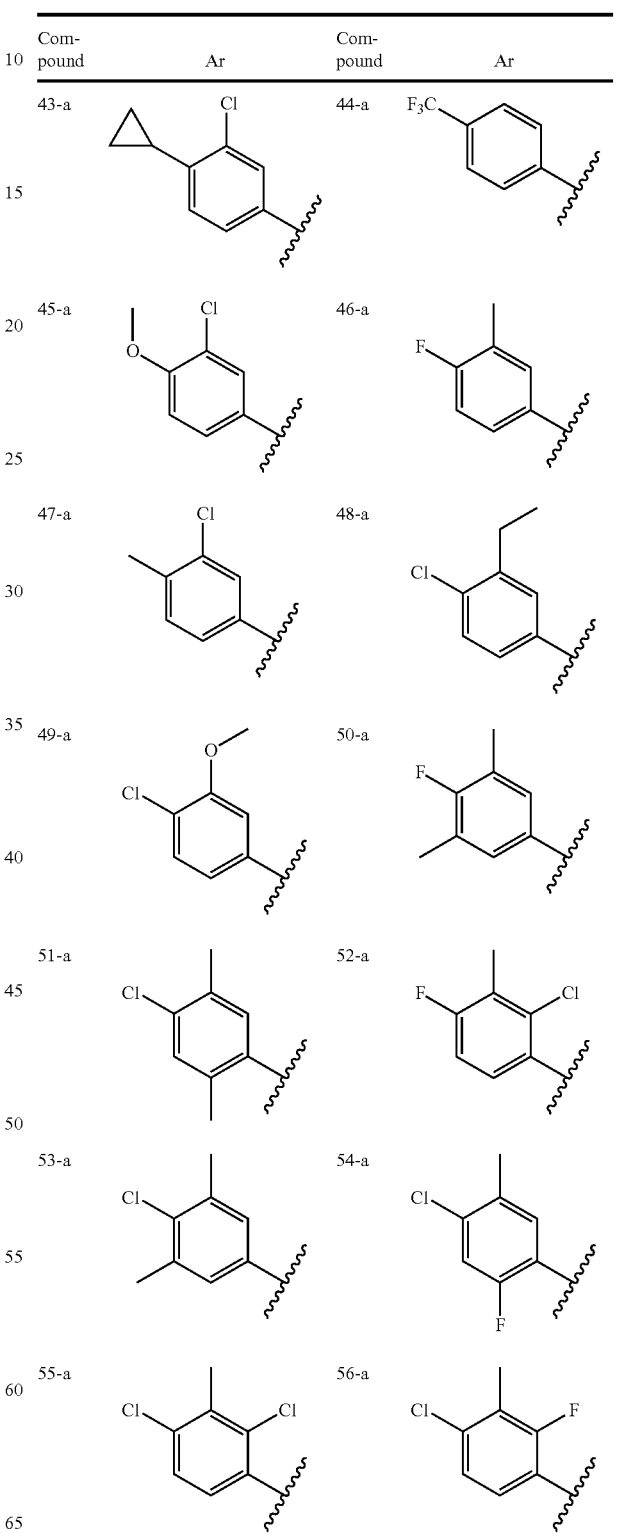

The intermediate compound is represented by the formula (I), and the substituent aromatic ring group Ar is shown in the following table.

-continued

| Compound | Ar | Compound | Ar |
|---|---|---|---|
| 57-a | F₃CO-pyridyl | 58-a | trifluoromethylphenyl (F,F,F, Me) |
| 59-a | 3,5-dichlorophenyl | 60-a | 4-chloro-3-methylphenyl |

Preparation of Intermediate 61-a:

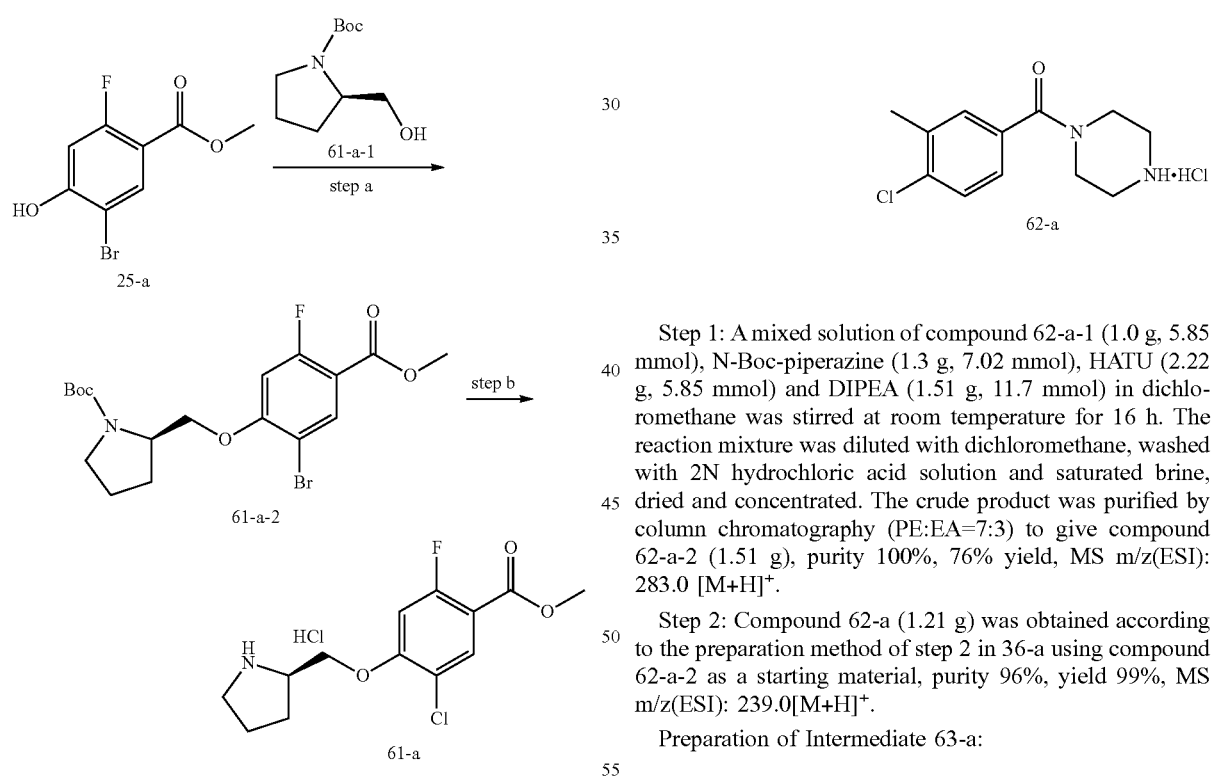

Step a: To a solution of compound 61-a-1 (2.01 g, 0.01 mol), compound 25-a (2.49 g, 0.01 mol), triphenylphosphine (5.24 g, 0.02 mol) in tetrahydrofuran was slowly added DIAD 4.04 g, 0.02 mol), and the reaction mixture was stirred at room temperature for 1 h. The reaction mixture was washed with saturated brine, dried and concentrated, and the crude product was purified by column chromatography to give 61-a-2 (2.08 g), purity 10000, yield 59%, MS m/z(ESI): 376.1[M+H−56]+.

Step b: 4 M of a solution of hydrochloric acid in dioxane (5 ml) was added to a solution of compound 61-a-2 (2.08 g, 4.81 mmol) in methanol, and the reaction solution was stirred at room temperature for 5 h. The reaction mixture was concentrated under reduced pressure to give 61-a (1.6 g), purity 1000, yield 98%, MS m/z(SI): 370[M+H]+.

Preparation of Intermediate 62-a:

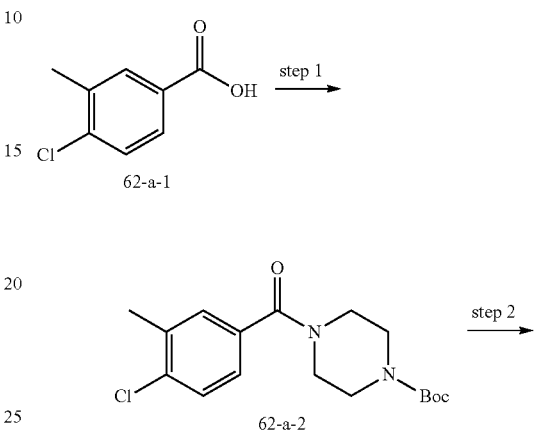

Step 1: A mixed solution of compound 62-a-1 (1.0 g, 5.85 mmol), N-Boc-piperazine (1.3 g, 7.02 mmol), HATU (2.22 g, 5.85 mmol) and DIPEA (1.51 g, 11.7 mmol) in dichloromethane was stirred at room temperature for 16 h. The reaction mixture was diluted with dichloromethane, washed with 2N hydrochloric acid solution and saturated brine, dried and concentrated. The crude product was purified by column chromatography (PE:EA=7:3) to give compound 62-a-2 (1.51 g), purity 100%, 76% yield, MS m/z(ESI): 283.0 [M+H]+.

Step 2: Compound 62-a (1.21 g) was obtained according to the preparation method of step 2 in 36-a using compound 62-a-2 as a starting material, purity 96%, yield 99%, MS m/z(ESI): 239.0[M+H]+.

Preparation of Intermediate 63-a:

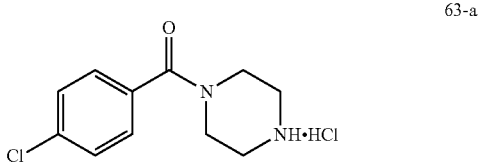

Compound 63-a was obtained according to the preparation method of compound 62-a using 4-chlorobenzoic acid as a starting material.

Example 80: Preparation of (R)-5-chloro-N-(cyclopropylsulfonyl)-2-fluoro-4-((1-(4-(trifluoromethyl)phenyl)pyrrolidine-2-yl)methoxy)benzamide(Z-80)

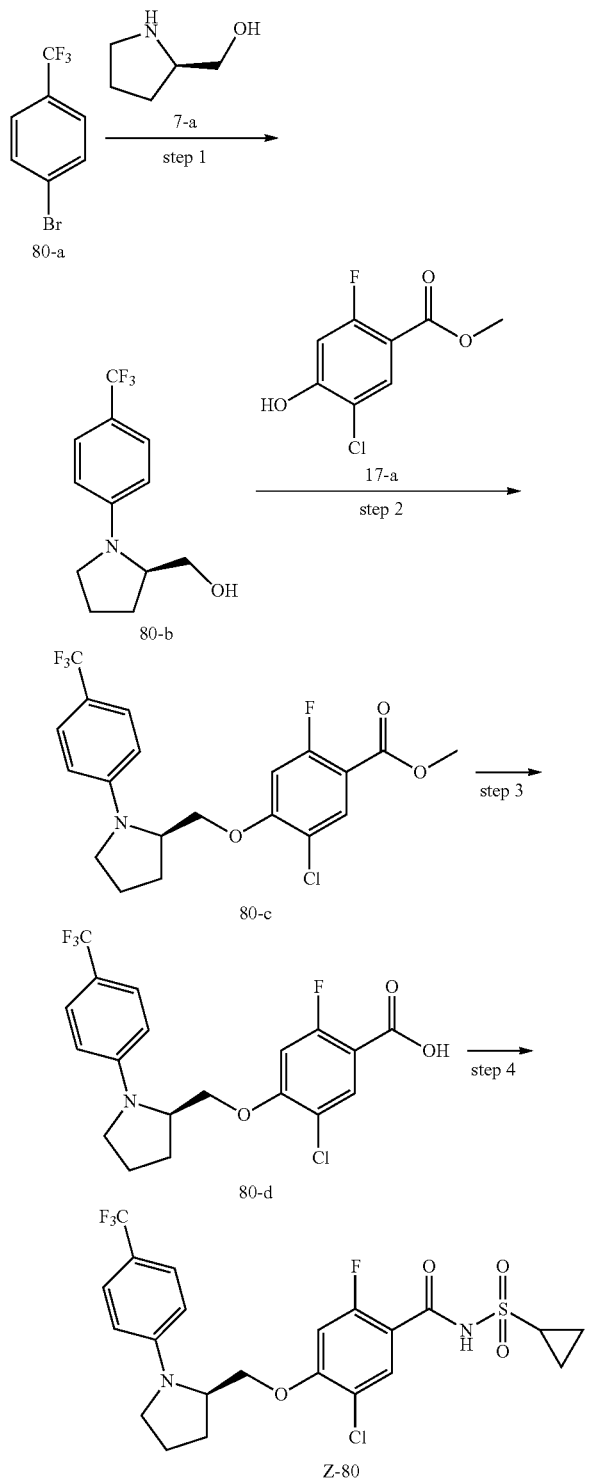

Step 1: A mixed solution of compound 80-a (9.0 g, 40 mmol), compound 7-a (6.08 g, 60 mmol), (L)-proline (920 mg, 8 mmol), cuprous iodide(764 mg, 4 mmol), potassium carbonate (16.56 g, 120 mmol) in dimethylsulfoxide (50 ml) was stirred under argon at 100° C. for 16 h. After the reaction mixture was cooled to room temperature, the reaction mixture was poured into water, extracted with ethyl acetate (3*60 ml), and the organic phase was washed with water (2*150 ml) and saturated brine (100 ml), dried and concentrated. The crude product was purified by column chromatography (PE/EA=4:1) to give a yellow oil compound 80-b (3.98 g), purity 100%, yield 41%, m/z(ESI): 246.1[M+H]$^+$.

Step 2: To a mixed solution of compound 80-b (956 mg, 3.9 mmol), compound 17-a (800 mg, 3.9 mmol), triphenylphosphine (2.04 g, 7.8 mmol) in tetrahydrofuran (1.58 g, 7.8 mmol) was added dropwise DIAD(1.58 g, 7.8 mmol), and stirred at room temperature for 1 h. The reaction mixture was concentrated under reduced pressure, and the crude product was purified by column chromatography (PE/EA=10:1) to give compound 80-c(1 g) as a colorless oil, purity 80%, yield 65%, MS m/z(ESI): 432.2[M+H]$^+$.

Step 3: To a solution of compound 80-c (1.1 g, 2.55 mmol) in methanol (20 ml) was added 2 M sodium hydroxide solution (5 ml), the mixture solution was stirred for 2 h at 60° C. Most of the solvent was removed under reduced pressure, and 20 ml of water was added to the residue, adjusted to pH 3-4 with 2N hydrochloric acid solution and extracted with ethyl acetate. The organic phase was washed with saturated brine, dried and concentrated to give compound 80-d (0.84 g) as a pale yellow solid, purity 96%, yield 79%, MS m/z(ESI): 418.1 [M+H]$^+$.

Step 4: A mixed solution of compound 80-d (100 mg, 0.239 mmol), cyclopropylsulfamide (58 mg, 0.478 mmol), HATU (100 mg, 0.263 mmol), DIPEA (62 mg, 0.478 mmol) mmol), DMAP(3 mg, 0.024 mmol) in dichloromethane was stirred for 16 h at room temperature. The reaction solution was diluted with 20 ml of dichloromethane, washed with 2N hydrochloric acid solution and saturated brine, and the organic phase was dried and concentrated. The crude product was purified by Pre-HPLC to obtain a white solid compound Z-80 (12 mg), purity 99%, yield 10%, MS m/z(ESI): 521.2[M+H]$^+$. $^1$H NMR (DMSO-d6, 400 MHz): δ 7.73 (d, J=7.6 Hz, 1H), 7.42 (d, J=8.8 Hz, 2H), 7.01 (d, J=12.4 Hz, 1H), 6.78 (d, J=8.8 Hz, 2H), 4.24 (br.s., 1H), 4.05-4.14 (m, 2H), 3.47 (t, J=8.8 Hz, 1H), 3.14-3.21 (m, 1H), 2.84-2.91 (m, 1H), 2.17-2.29 (m, 1H), 1.99-2.07 (m, 3H), 0.78-0.88 ppm (m, 4H).

Example 119: Preparation of (R)-5-chloro-N-(cyclopropylsulfonyl)-2-fluoro-4-((1-(6-(trifluoromethyl)pyridin-3-yl)pyrrolidin-2-yl)methoxy) benzamide (Z-119)

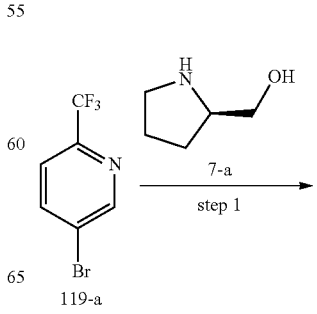

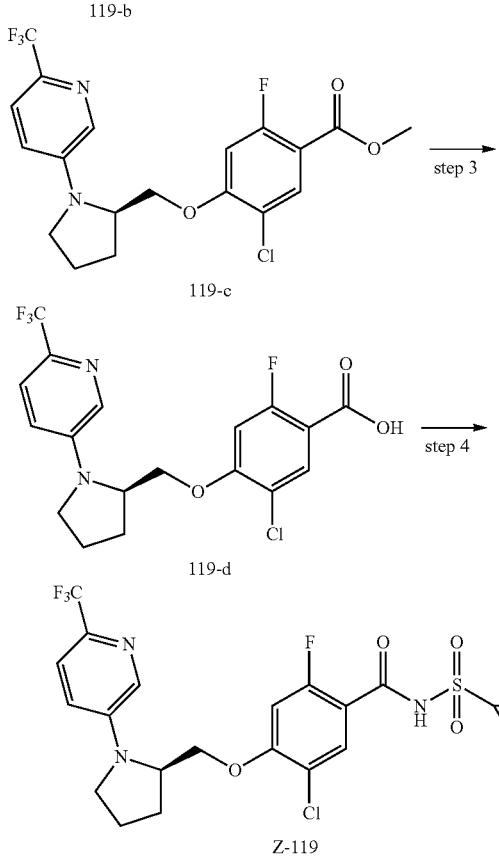

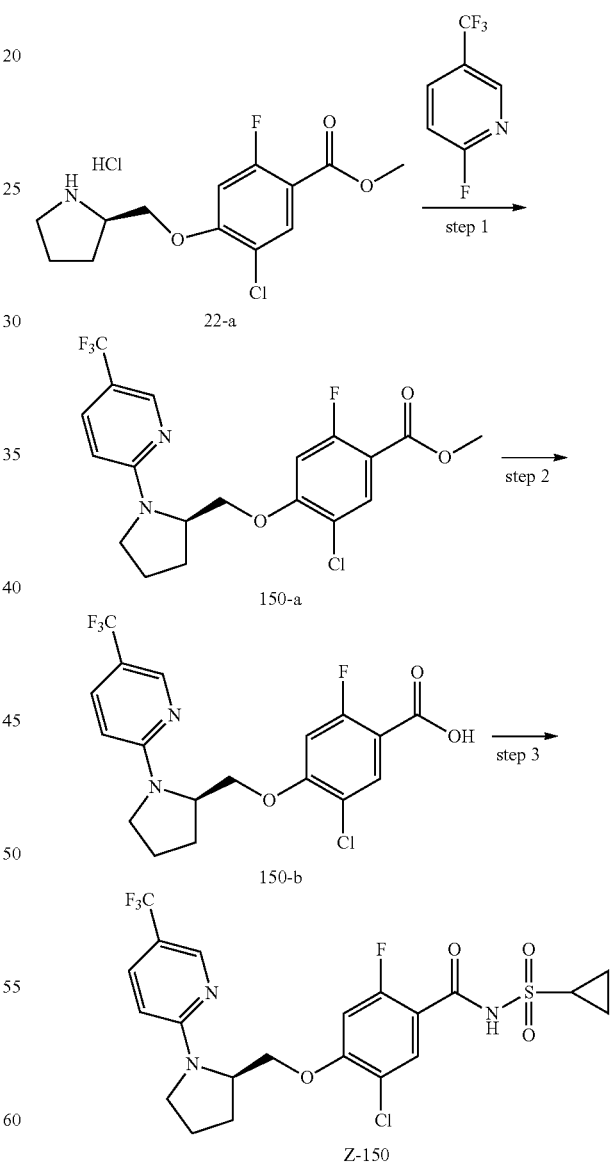

Step 4: A white solid compound Z-119 (42 mg) was obtained according to the preparation method of step 4 in example 80 using compound 119-d as a starting material, purity 100%, yield 38%, MS m/z(ESI): 522.1[M+H]⁺. ¹H NMR (400 MHz, DMSO-d6): δ 12.02 (br.s., 1H), 8.18 (d, J=2.4 Hz, 1H), 7.72 (d, J=7.6 Hz, 1H), 7.56 (d, J=8.8 Hz, 1H), 7.22-7.15 (m, 2H), 4.38 (d, J=8.0 Hz, 1H), 4.20-4.17 (m, 2H), 3.54 (t, J=8.4 Hz, 1H), 3.26-3.20 (m, 1H), 3.06-2.99 (m, 1H), 2.27-2.19 (m, 1H), 2.06-2.03 (m, 3H), 1.09-1.05 (m, 4H).

Example 150: Preparation of (R)-5-chloro-N-(cyclopropylsulfonyl)-2-fluoro-4-((1-(5-(trifluoromethyl)pyridin-2-yl)pyrrolidin-2-yl)methoxy)benzamide (Z-150)

Step 1: A mixed solution of compound 119-a (1.13 g, 5 mmol), compound 7-a (1.01 g, 10 mmol), potassium carbonate (1.38 g, 10 mmol) in DMF was stirred for 48 h at 100° C. The reaction solution was cooled to room temperature and poured into water, extracted with ethyl acetate. The organic phase was washed with saturated brine, dried and concentrated. The crude product was purified by column chromatography (PE:EA=1:1) to give a yellow oily compound 119-b(420 mg), purity 100%, yield 34%, MS m/z (ESI): 247.1[M+H]⁺.

Step 2: A white solid compound 119-c (318 mg) was obtained according to the preparation method of step 2 in example 80 using compound 119-b as a starting material, purity 74%, yield 100%, MS m/z(ESI): 433.1[M+H]⁺.

Step 3: A white solid compound 119-d (409 mg) was obtained according to the preparation method of step 3 in example 80 using compound 119-c as a starting material, purity 95%, yield 52%, MS m/z(ESI): 419.1[M+H]⁺.

Step 1: A mixed solution of compound 22-a (6.87 g, 0.02 mol), compound 2-fluoro-5-(trifluoromethyl)pyridine (3.5 g, 0.02 mol), potassium carbonate (8.29 g, 0.06 mmol) in acetonitrile was stirred overnight at 80° C. After the reaction mixture was cooled to room temperature, water was added and extracted with ethyl acetate. The organic phase was dried and concentrated. The crude product was purified by column chromatography (PE/EA=10:1) to give a pale yellow solid compound 150-a(6.9 g), purity 93%, yield 75%, MS m/z(ESI): 433.1[M+H]⁺.

Step 2: A white solid compound 150-b (6.422) was obtained according to the preparation method of step 3 in example 80 using compound 150-a as a starting material, purity 99%, yield 92%, MS m/z(ESI): 419.1[M+H]⁺.

Step 3: A white solid compound Z-150 (4.73 g) was obtained according to the preparation method of step 4 in example 80 using compound 150-b as a starting material, purity 100%, yield 59%, MS m/z(ESI): 522.1[M+H]⁺. ¹H NMR (400 MHz, DMSO-d6): δ 12.01 (br.s., 1H), 8.38 (br.s., 1H), 7.77 (dd, J=2.4 Hz, 8.8 Hz, 1H), 7.73 (d, J=7.6 Hz, 1H), 7.38 (d, J=12.4 Hz, 1H), 6.68 (d, J=9.2 Hz, 1H), 4.54-4.51 (m, 1H), 4.30 (dd, J=3.2 Hz, 10.0 Hz, 1H), 4.18 (dd, J=6.0 Hz, 9.6 Hz, 1H), 3.54 (t, J=8.4 Hz, 1H), 3.37-3.30 (m, 1H), 3.08-3.00 (m, 1H), 2.31-2.18 (m, 1H), 2.10-1.99 (m, 3H), 1.12-1.07 (m, 4H).

Example 125: Preparation of (R)-5-cyclopropyl-N-(cyclopropyl)-2-fluoro-4-((1-(4-(trifluoromethyl)phenyl)pyrrolidin-2-yl)methoxy)benzamide(Z-125)

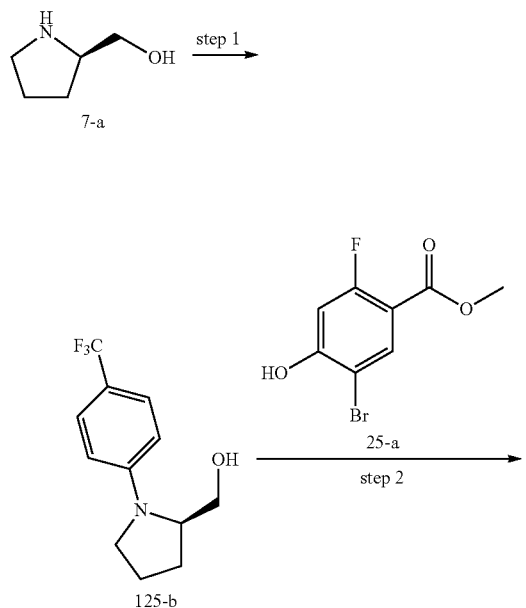

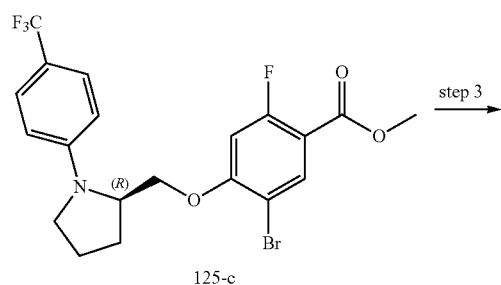

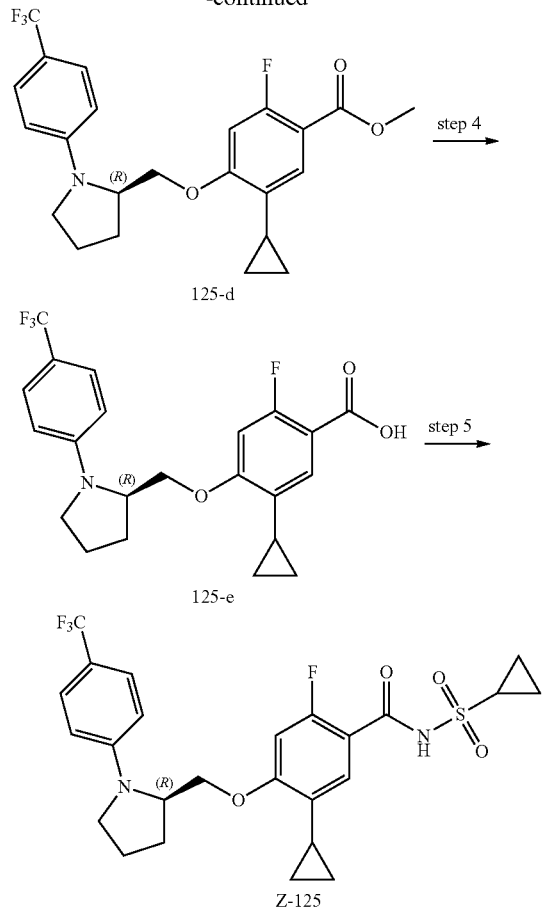

Step 1: A mixed solution of 4-bromo-trifluoromethylbenzene (20 g, 0.089 mol), compound 7-a (13.486 g, 0.133 mol), (L)-proline (2.047 g, 0.017 mol), cuprous iodide (1.693 g, 0.009 mol) and potassium carbonate (30.854 g, 0.267 mol) in dimethyl sulfoxide was stirred under argon at 90° C. overnight. The reaction mixture was cooled to room temperature, poured into water and extracted with ethyl acetate. The organic phase was washed with saturated brine, dried and concentrated. The crude product was purified by column chromatography (PE:EA=3:1) to give compound 125-b (8.872 g) as a yellow oil, purity 100%, yield 41%, MS m/z(ESI): 246.1[M+H]⁺.

Step 2: To a solution of compound 125-b (1.48 g, 6.02 mmol), compound 25-a (1.5 g, 6.02 mmol), triphenylphosphine (3.15 g, 12.04 mmol) in tetrahydrofuran was added DIAD (2.43 g, 12.04 mmol) dropwise. Upon addition, the reaction mixture was stirred continuously at room temperature for 1 h. The reaction mixture was concentrated under reduced pressure. The crude product was purified by column chromatography (PE:EA=10:1), prepared into a slurry in 10 ml of methanol and filtered. The filter cake was washed with methanol and dried to give compound 125-c (1.24 g) as a white solid, purity 98%, yield 43%, MS m/z(ESI): 478.1 [M+H]⁺.

Step 3: A solution of compound 125-c (1.13 g, 2.6 mmol), cyclopropyl boronic acid (0.45 g, 5.2 mmol), Pd(dppf)Cl2 (0.19 g, 0.26 mmol), cesium carbonate (1.7 g, 5.2 mmol) in dioxane was stirred under argon at 90° C. for 24 h. The reaction mixture was cooled to room temperature and then filtered. The filter cake was washed with ethyl acetate and the filtrate was concentrated under reduced pressure. The crude product was purified by column chromatography (PE:EA=10:1) to obtain compound 125-d (1.13 g) as a white solid, purity 100%, yield 99%, MS m/z(ESI): 438.2[M+H]$^+$.

Step 4: To a solution of compound 125-d (1.053 g, 2.407 mmol) in methanol was added 1 M sodium hydroxide solution (10 ml), and the reaction solution was stirred at 60° C. for 2 h. The reaction mixture was concentrated under reduced pressure to remove methanol, water was added. The pH value was adjusted to 2-3 with 1 M hydrochloric acid solution. The reaction mixture was filtered, and the filter cake was washed with water and dried to give a white solid 125-e (1.16 g), purity 100%, yield 100%, MS m/z(ESI): 424.1[M+H]$^+$.

Step 5: A mixed solution of compound 125-e (200 mg, 0.472 mmol), cyclopropylsulfonamide (290 mg, 2.362 mmol), EDCI (270 mg, 1.417 mmol), DMAP (170 mg, 1.417 mmol), DIPEA (370 mg, 2.834 mmol) in dichloromethane was stirred at room temperature overnight. The reaction mixture was washed with water, dried and concentrated. The crude product was purified by Pre-HPLC to give a white solid Z-125 (72 mg), purity 100%, yield 29%, MS m/z(ESI): 527[M+H]$^+$. $^1$H NMR (500 MHz, DMSO): δ 11.815 (s, 1H), 7.453 (d, J=10.5 Hz, 2H), 7.110 (d, J=10.5 Hz, 1H), 6.956 (d, J=16 Hz, 1H), 6.819 (m, J=11 Hz, 2H), 4.341-4.321 (m, 1H), 4.114-4.087 (m, 2H), 3.514 (t, J=11 Hz, 1H), 3.226-3.208 (m, 1H), 3.069-3.057 (m, 1H), 2.216-1.923 (m, 5H), 1.117-1.079 (m, 4H), 0.882-0.763 (m, 2H), 0.657-0.644 (m, 2H).

Example 142: Preparation of (R)-5-cyclopropyl-N-(cyclopropylsulfonyl)-2-fluoro-4-((1-(5-(trifluoromethyl)pyridin-2-yl)pyrrolidin-2-yl)methoxy)benzamide (Z-142)

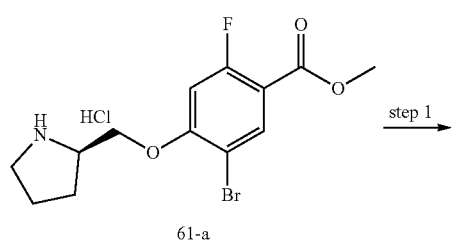

61-a

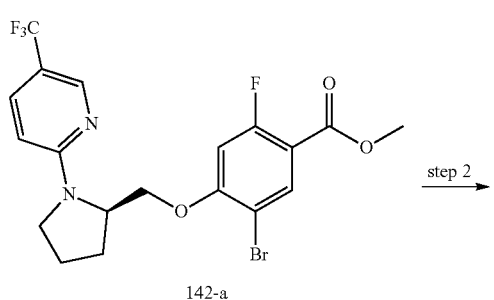

142-a

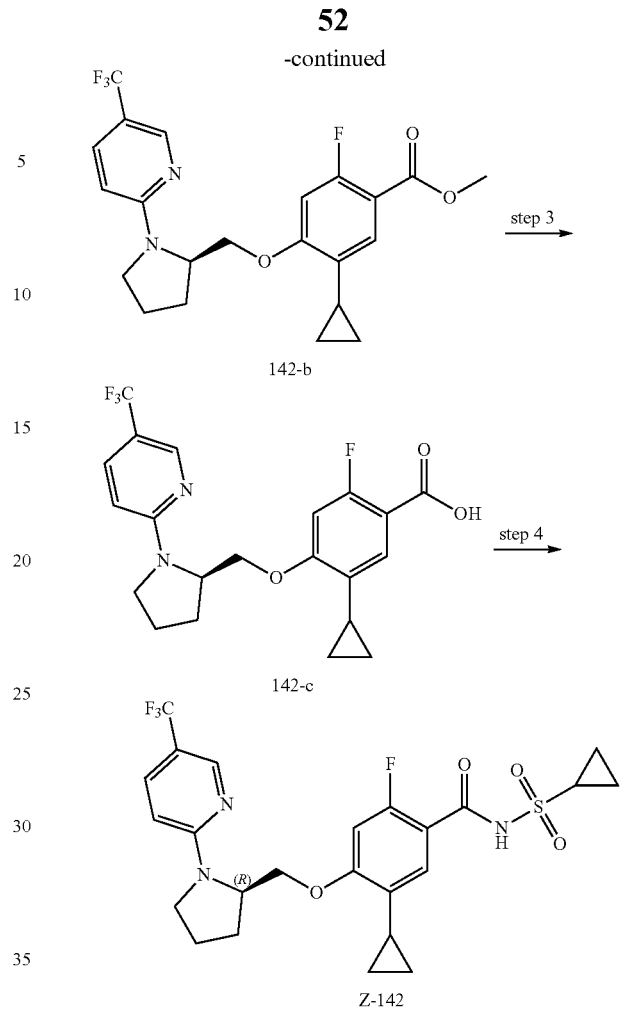

Step 1: A mixed solution of compound 61-a (1.6 g, 4.34 mmol), 2-fluoro-5-trifluoromethylpyridine (0.72 g, 4.34 mmol), potassium carbonate (1.8 g, 13.02 mmol) in acetonitrile was stirred at 80° C. for 20 h. The reaction mixture was cooled to room temperature, diluted with ethyl acetate, washed with water and saturated brine, and the organic phase was dried and concentrated. The crude product was prepared into a slurry in methanol and filtered. The filter cake was washed with methanol and dried to obtain a white solid compound 142-a(1.1 g), purity 100%, yield 53%, MS m/z(ESI): 479.1[M+H]$^+$.

Step 2: Compound 142-b (0.9 g) was obtained as a white solid according to the preparation method of step 3 in Example 125 using compound 142-a(1.0 g, 2.1 mmol) as a starting material, purity 95%, yield 98%, MS m/z(ESI): 439.2 [M+H]$^+$.

Step 3: Compound 142-c (0.8 g) was obtained as a white solid according to the preparation method of step 4 in Example 125 using compound 142-b(0.9 g, 2.05 mmol) as a starting material, purity 96%, yield 92%, MS m/z(ESI): 425.2[M+H]$^+$.

Step 4: Compound Z-142 (26 mg) was obtained as a white solid according to the preparation method of step 5 in Example 125 using compound 142-c(100 mg, 0.236 mmol) as a starting material, purity 100%, yield 24%, MS m/z (ESI): 528.2[M+H]$^+$. $^1$H NMR (DMSO-d6, 400 MHz): δ 11.79 (br. s., 1H), 8.38 (s, 1H), 7.77 (dd, J=8.8, 2.4 Hz, 1H), 7.11 (d, J=8.4 Hz, 1H), 7.04 (d, J=13.2 Hz, 1H), 6.68 (d, J=9.2 Hz, 1H), 4.54 (br. s., 1H), 4.23 (dd, J=9.6, 3.6 Hz, 1H), 4.07 (dd, J=9.8, 6.8 Hz, 1H), 3.54 (t, J=9.2 Hz, 1H), 3.32-3.41 (m, 1H), 2.92-3.07 (m, 1H), 2.11-2.27 (m, 1H), 1.88-2.09 (m, 4H), 0.95-1.08 (m, 4H), 0.74-0.91 (m, 2H), 0.61 ppm (dd, J=5.2, 1.6 Hz, 2H).

Example 89: Preparation of 5-chloro-N-(cyclopropylsulfonyl)-4-((4-(3,4-dichlorophenyl)piperazin-1-yl)methyl)-2-fluorobenzamide (Z-89)

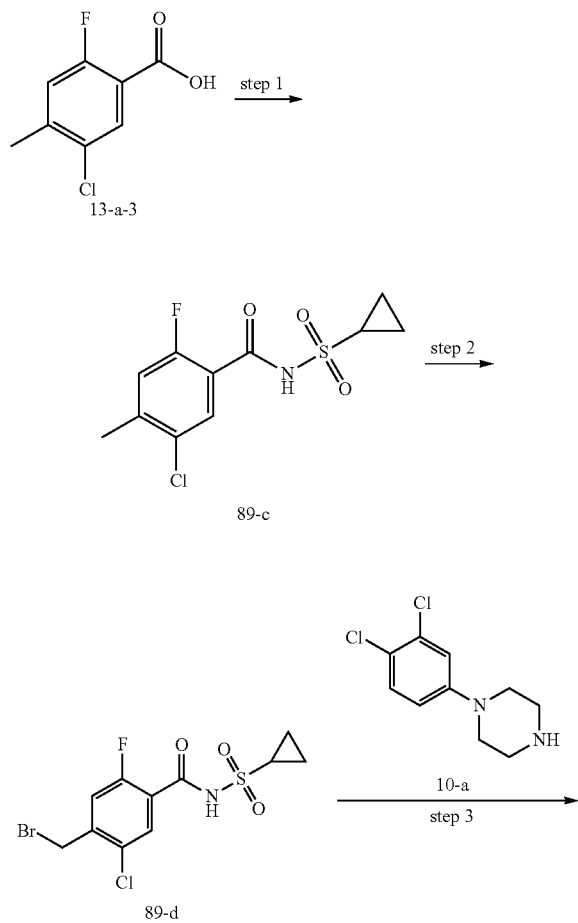

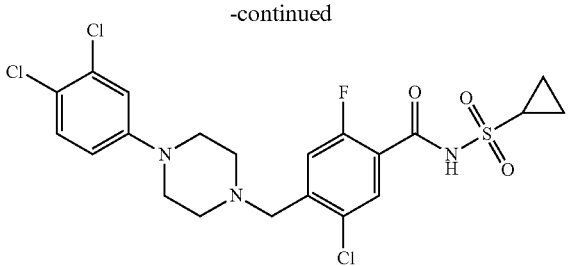

Step 1: Compound 89-c (456 mg) was obtained according to the preparation method of step 5 in Example 125 using compound 13-a-3 (300 mg) as a starting material, MS m/z(ESI): 290[M–H]⁻.

Step 2: Compound 89-d (419 mg) was obtained according to the preparation method of step d in intermediate 13-a using compound 89-c (452 mg) as a starting material, MS m/z(ESI): 372[M+H]⁺.

Step 3: A mixed solution of compound 89-d (109 mg), compound 10-a, potassium carbonate in acetonitrile was stirred at 80° C. for 3 h. The reaction solution was cooled to room temperature, added with water, extracted with ethyl acetate, the organic phase was dried and concentrated, and the crude product was purified by Pre-HPLC to give compound Z-89 (23.34 mg), purity 100%, yield 15%, MS m/z(ESI): 520.1 [M+H]⁺. ¹H NMR (400 MHz, DMSO-d6): δ 7.71 (d, J=6.4 Hz, 1H), 7.40 (d, J=11.2 Hz, 1H), 7.36 (d, J=9.2 Hz, 1H), 7.10 (d, J=2.8 Hz, 1H), 6.90 (dd, J=3.2 Hz, 9.2 Hz, 1H), 3.63 (s, 2H), 3.20-3.18 (m, 4H), 3.12-2.94 (m, 1H), 2.56-2.55 (m, 4H), 1.03-0.96 (m, 4H).

Example 92, 159, 164

Compounds Z-92, Z-159, Z-164 were prepared according to the similar method of step 3 in Example 89 using 89-d as a starting material and the corresponding phenyl substituted or pyridyl substituted piperazines.

| Example | Structure | MS | ¹H NMR |
|---|---|---|---|
| 92 | ![structure] | 570.1 [M + H]⁺ | ¹H NMR (400 MHz, DMSO-d6): δ 12.24 (br. s., 1H), 8.09 (d, J = 10.0 Hz, 1H), 7.86 (d, J = 6.4 Hz, 1H), 7.37 (d, J = 8.8 Hz, 1H), 7.21 (d, J = 3.2 Hz, 1H), 6.99 (dd, J = 2.8 Hz, 9.2 Hz, 1H), 4.50 (s, 2H), 3.42-3.41 (m, 8H), 3.10-3.03 (m, 1H), 3.14-1.11 (m, 4H). |

| Example | Structure | MS | ¹H NMR |
|---|---|---|---|
| 159 | 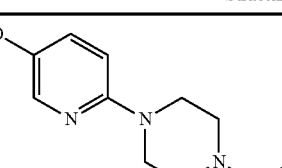
Z-159 | 537.2 [M + H]⁺ | ¹H NMR (400 MHz, DMSO-d6): δ 12.13 (br. s., 1H), 8.12 (d, J = 2.4 Hz, 1H), 7.72 (d, J = 6.4 Hz, 1H), 7.58 (dd, J = 1.6 Hz, 8.4 Hz, 1H), 7.47 (d, J = 10.8 Hz, 1H), 6.89 (d, J = 9.6 Hz, 1H), 3.67 (s, 2H), 3.55-3.52 (m, 4H), 3.06-2.99 (m, 1H), 2.55-2.54 (m, 4H), 1.09-1.02 (m, 4H). |
| 164 | 
Z-164 | 500.1 [M + H]⁺ | ¹H NMR (400 MHz, DMSO-d6): δ 7.67 (d, J = 6.8 Hz, 1H), 7.27 (d, J = 11.2 Hz, 1H), 7.15 (d, J = 8.8 Hz, 1H), 6.90 (d, J = 2.8 Hz, 1H), 6.74 (dd, J = 2.8 Hz, 8.8 Hz, 1H), 3.59 (s, 2H), 3.14-3.11 (m, 4H), 2.89-2.82 (m, 1H), 2.57-2.54 (m, 4H), 2.23 (s, 3H), 0.87-0.82 (m, 2H), 0.77-0.72 (m, 2H). |

Example 117: Preparation of 5-chloro-N-(cyclopropylsulfonyl)-4-((1-(3,4-dichlorophenyl)piperidin-4-yl)oxy)-2-fluorobenzamide (Z-117)

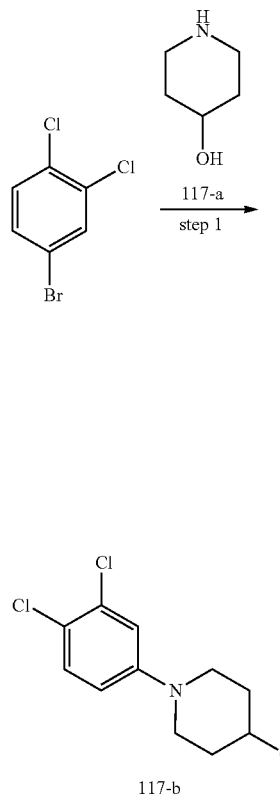

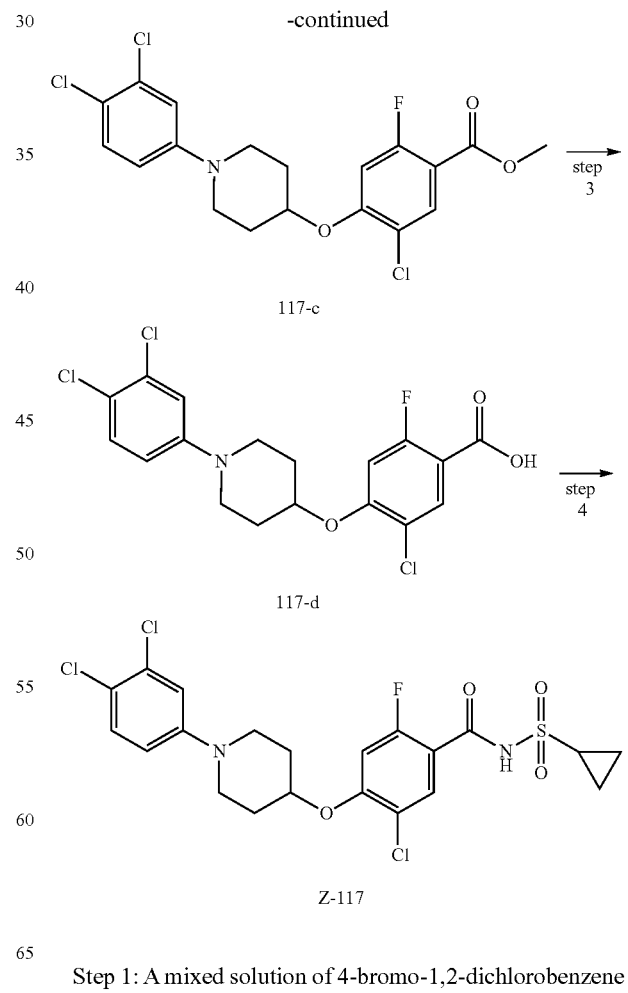

Step 1: A mixed solution of 4-bromo-1,2-dichlorobenzene (200 g, 0.885 mol), compound 117-a (224 g, 2.218 mol), (L)-proline (10.2 g, 0.089 mol), copper iodide (34.2 g, 0.180 mol) and potassium carbonate (366 g, 2.652 mol) in dimethyl sulfoxide (1.0 L) was stirred under argon at 100° C. for 16 h. The reaction mixture was cooled to room temperature, 2.0 L of ethyl acetate was added, and the insoluble material was removed by filtration. The filter cake was washed with ethyl acetate. The filtrate was washed with saturated brine, dried and concentrated to give crude compound 117-b (175 g), purity 88%, MS m/z(ESI): 247 [M+H]$^+$.

Step 2: To a solution of compound 117-b (4.7 g, 16.26 mmol), compound 17-a (3.34 g, 16.26 mmol), triphenylphosphine (8.52 g, 32.52 mmol) in tetrahydrofuran was added DIAD (6.5 g, 32.52 mmol) dropwise at 0° C., and the reaction mixture was stirred under nitrogen at room temperature for 12 h. The reaction mixture was poured into water and extracted with ethyl acetate. The organic phase was washed with saturated brine, dried and concentrated to give the crude compound 117-c (6.7 g), purity 89%, MS m/z(ESI): 432[M+H]$^+$.

Step 3: 4M sodium hydroxide solution (15 ml) was added to a solution of compound 117-c (6.7 g, 15.5 mmol) in tetrahydrofuran, and the reaction mixture was stirred at room temperature overnight. Tetrahydrofuran was removed by concentration under reduced pressure, and the pH value was adjusted to 5-6 with 1M hydrochloric acid. The reaction mixture was extracted with ethyl acetate. The organic phase was washed with saturated brine, dried and concentrated to give the crude compound 117-d (6.4 g), purity 90%, MS m/z(ESI): 419[M+H]$^+$.

Step 4: A solution of compound 117-d (100 mg, 0.239 mmol), cyclopropylsulfonamide (58 mg, 0.478 mmol), HATU (100 mg, 0.263 mmol), triethylamine (48 mg, 0.478 mmol), DMAP(3 mg, 0.024 mmol) in dichloromethane was stirred at room temperature for 12 h. The reaction solution was diluted with 20 ml of dichloromethane, washed with 2N hydrochloric acid solution, and the organic phase was dried and concentrated. The crude product was purified by Pre-HPLC to give compound Z-117 (15 mg), purity 100%, yield 12%, MS m/z(ESI): 523.1 [M+H]$^+$. $^1$H NMR (DMSO-d6, 400 MHz): δ 11.99 (br. s., 1H), 7.74 (d, J=7.6 Hz, 1H), 7.29-7.45 (m, 2H), 7.14 (d, J=2.8 Hz, 1H), 6.94 (dd, J=9.2, 2.8 Hz, 1H), 4.78-4.93 (m, 1H), 3.39-3.54 (m, 2H), 3.13-3.26 (m, 2H), 2.96-3.10 (m, 1H), 1.90-2.07 (m, 2H), 1.61-1.78 (m, 2H), 0.94-1.22 ppm (m, 4H).

Example 172: Preparation of (R)-5-Chloro-N-(cyclopropylsulfonyl)-4-((4-(3,4-dichlorophenyl)-2-methylpiperazin-1-yl)methyl)-2-fluorobenzamide (Z-172)

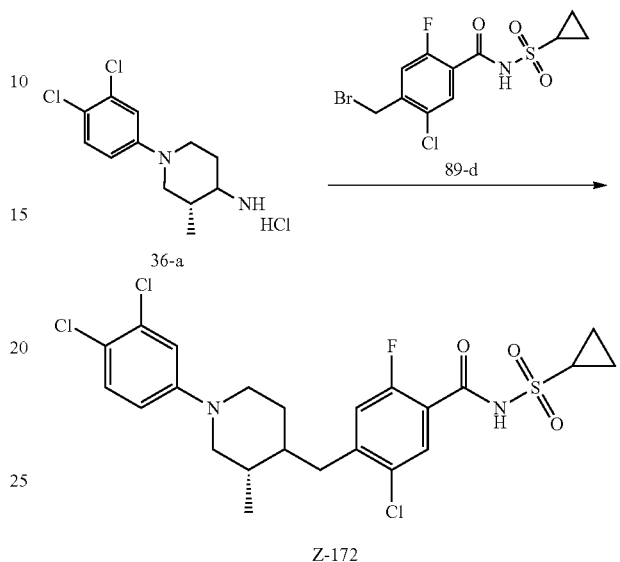

A mixed solution of compound 36-a (100 mg, 0.408 mmol), compound 89-d 151 mg, 0.408 mmol) and potassium carbonate in DMF was stirred at 80° C. for 3 h. The reaction solution was cooled to room temperature, poured into water, and extracted with ethyl acetate. The organic phase was washed with saturated brine, dried and concentrated. The crude product was purified by Pre-HPLC to give compound Z-172 (70 mg) as a white solid, purity 100%, yield 32%, MS m/z(ESI): 533.8[M+H]$^+$. $^1$H NMR (dmso, 400 MHz): δ 12.18 (brs., 1H), 7.71 (d, J6.0 Hz, H), 7.49 (d, J11.2 Hz, H), 7.35 (d, J9.2 Hz, 1H), 7.11 (d, J=2.8 Hz, 1H), 6.91 (dd, J=8.8, 2.8 Hz, 1H), 3.97 (d, J=14.8 Hz, 1H), 3.54 (d, J=8.4 Hz, 1H), 3.35-3.50 (m, 2H), 2.96-3.09 (m, 1H), 2.86 (t, J=10.4 Hz, 1H), 2.57-2.77 (m, 3H), 2.36 (br. s., 1H), 0.97-1.17 ppm (m, 7H)

Examples 173-188

Compounds Z-173 to Z-188 were prepared according to the method of Example 172 using 89-d as a starting material, except that 36-a was replaced by the corresponding substituted bromobenzene.

| Example | Structure | MS | $^1$H NMR |
|---|---|---|---|
| 173 | ![Z-173 structure] | 525.8 [M + H]$^+$ | $^1$H NMR (dmso, 400 MHz): δ = 12.05 (br. s., 1 H), 7.73 (d, J = 6.4 Hz, 1 H), 7.46 (d, J = 10.8 Hz, 1 H), 6.91 (d, J = 2.4 Hz, 1 H), 6.73-6.87 (m, 2 H), 3.69 (s, 2 H), 3.14 (br. s., 4 H), 2.93-3.07 (m, 1 H), 2.61 (br. s., 4 H), 1.84-2.02 (m, 1 H), 0.97-1.17 (m, 4 H), 0.79-0.94 (m, 2 H), 0.46-0.63 ppm (m, 2 H) |

-continued

| Example | Structure | MS | ¹H NMR |
|---|---|---|---|
| 174 | 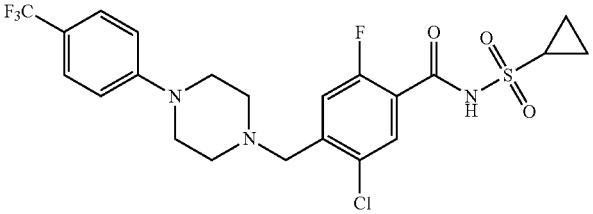<br>Z-174 | 519.8 [M + H]⁺ | ¹H NMR (dmso, 400 MHz): δ = 12.70 (br. s., 1 H), 12.11 (br. s., 1 H), 8.10 (s, 1H), 7.74 (d, J = 6.4 Hz, 1 H), 7.38-7.54 (m, 3 H), 7.04 (d, J = 8.8 Hz, 2 H), 3.69 (s, 2 H), 3.30 (br. s., 4H), 2.94-3.13 (m, 1 H), 2.62 (br. s., 4 H), 0.97-1.17 ppm (m, 4 H) |
| 175 | 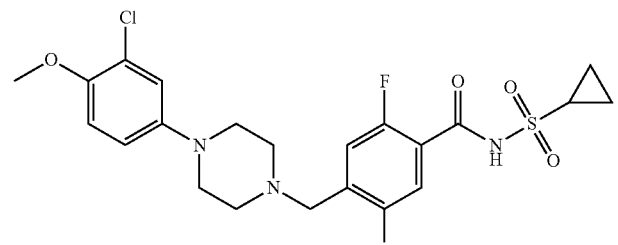<br>Z-175 | 515.8 [M + H]⁺ | ¹H NMR (dmso, 400 MHz): δ = 12.08 (br. s., 1 H), 7.72 (d, J = 6.4 Hz, 1 H), 7.44 (d, J = 10.8 Hz, 1 H), 6.95-7.04 (m, 2 H), 6.86 (dd, J = 8.8, 2.9 Hz, 1 H), 3.73 (s, 3 H), 3.67 (s, 2 H), 3.07 (br. s., 4 H), 2.94-3.04 (m, 1 H), 2.61 (br. s., 4 H), 0.93-1.12 ppm (m, 4 H) |
| 176 | 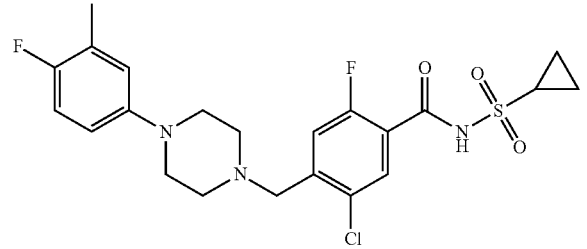<br>Z-176 | 483.9 [M + H]⁺ | ¹H NMR (dmso, 400 MHz): δ = 12.02 (br. s., 1 H), 7.74 (d, J = 6.4 Hz, 1 H), 7.48 (d, J = 10.8 Hz, 1 H), 6.94 (t, J = 9.2 Hz, 1 H), 6.82 (dd, J = 6.4, 2.8 Hz, 1 H), 6.66-6.77 (m, 1 H), 3.72 (s, 2 H), 3.05-3.12 (m, 4 H), 2.94-3.05 (m, 1 H), 2.57-2.74 (m, 4 H), 2.15 (s, 3 H), 0.96-1.19 ppm (m, 4 H) |
| 177 | 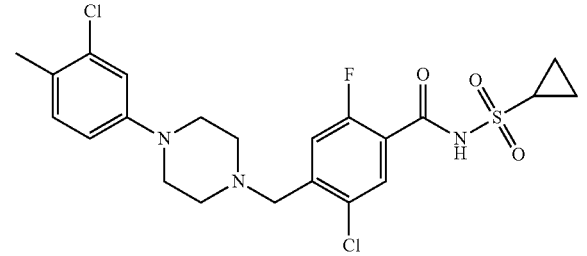<br>Z-177 | 499.8 [M + H]⁺ | ¹H NMR (dmso, 400 MHz): δ = 12.03 (br. s., 1 H), 7.74 (d, J = 6.4 Hz, 1 H), 7.49 (d, J = 10.8 Hz, 1 H), 7.13 (d, J = 8.4 Hz, 1 H), 6.92 (d, J = 2.4 Hz, 1 H), 6.81 (dd, J = 8.4, 2.4 Hz, 1 H), 3.74 (br. s., 2 H), 3.15 (br. s., 4 H), 2.94-3.05 (m, 1 H), 2.66 (br. s., 4 H), 2.18 (s, 3 H), 0.99-1.14 ppm (m, 4 H) |
| 178 | 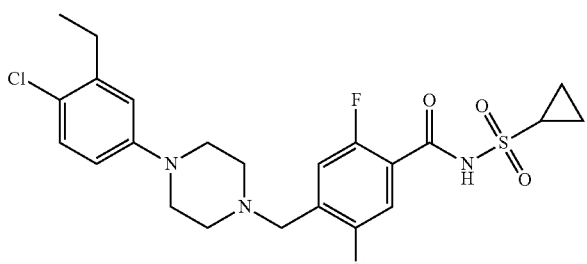<br>Z-178 | 513.8 [M + H]⁺ | ¹H NMR (dmso, 400 MHz): δ = 12.02 (br. s., 1 H), 7.75 (d, J = 6.4 Hz, 1 H), 7.50 (d, J = 10.8 Hz, 1 H), 7.17 (d, J = 8.8 Hz, 1 H), 6.88 (d, J = 2.8 Hz, 1 H), 6.76 (dd, J = 8.8, 2.8 Hz, 1 H), 3.75 (br. s., 2 H), 3.18 (br. s., 4 H), 2.95-3.09 (m, 1 H), 2.53-2.79 (m, 6 H), 1.05-1.20 ppm (m, 7 H) |

| Example | Structure | MS | ¹H NMR |
|---|---|---|---|
| 179 | 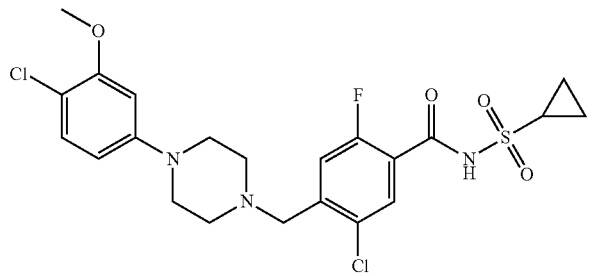<br>Z-179 | 515.8 [M + H]⁺ | ¹H NMR (dmso, 400 MHz): δ = 7.87 (d, J = 6.0 Hz, 1 H), 7.69 (d, J = 10.4 Hz, 1 H), 7.21 (d, J = 8.8 Hz, 1 H), 6.69 (d, J = 2.0 Hz, 1 H), 6.50 (dd, J = 8.8, 2.4 Hz, 1 H), 4.36 (br. s., 2 H), 3.80 (s, 3 H), 3.20 (br. s., 8 H), 2.97-3.13 (m, 1 H), 1.01-1.21 ppm (m, 4 H) |
| 180 | 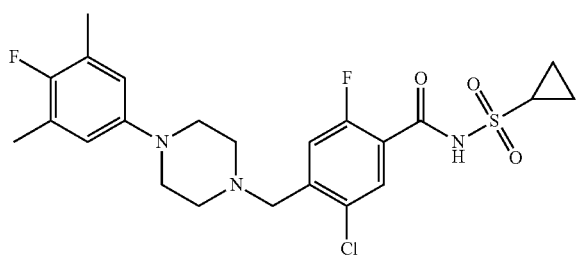<br>Z-180 | 496.1 [M − H]⁻ | ¹H NMR (400 MHz, DMSO-d6): δ 7.81 (d, J = 6.4 Hz, 1H), 7.56 (d, J = 10.8 Hz, 1H), 6.67 (d, J = 6.4 Hz, 2H), 3.92 (br. s., 2H), 3.16-3.15 (m, 4H), 3.10-3.06 (m, 1H), 2.83-2.81 (m, 4H), 2.16 (d, J = 1.6 Hz, 6H), 1.15-1.11 (m, 4H). |
| 181 | 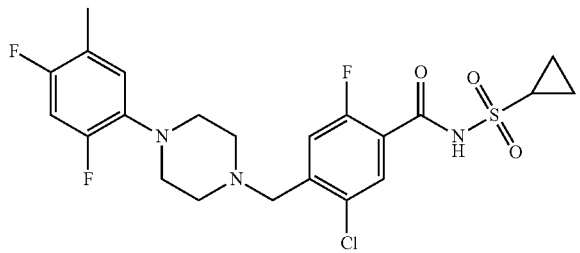<br>Z-181 | 500.1 [M − H]⁻ | ¹H NMR (400 MHz, DMSO-d6): δ 7.88 (d, J = 6.0 Hz, 1H), 7.70 (d, J = 9.6 Hz, 1H), 7.16 (dd, J = 10.0, 12.0 Hz, 1H), 7.01 (t, J = 8.8 Hz, 1H), 4.34-4.30 (m, 6H), 3.18-3.07 (m, 5H), 2.19 (s, 3H), 1.17-1.14 (m, 4H). |
| 182 | 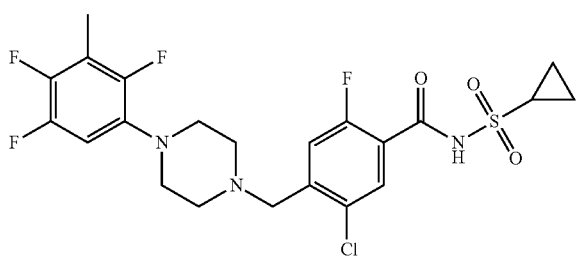<br>Z-182 | N/A | ¹H NMR (400 MHz, DMSO-d6): δ 7.79 (d, J = 6.0 Hz, 1H), 7.54 (d, J = 10.8 Hz, 1H), 7.07-6.99 (m, 1H), 3.84 (s, 2H), 3.10-3.04 (m, 5H), 2.77-2.76 (m, 4H), 2.18 (s, 3H), 1.16-1.11 (m, 4H). |
| 183 | 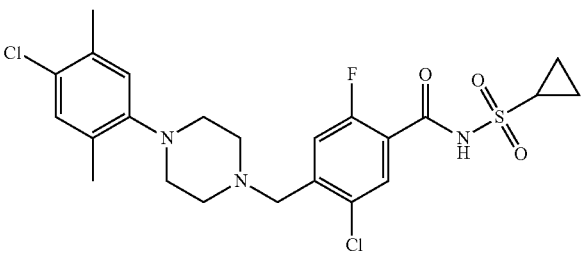<br>Z-183 | 514.2 [M + H]⁺ | ¹H NMR (dmso, 400 MHz): δ = 7.87 (d, J = 6.0 Hz, 1 H), 7.70 (d, J = 10.4 Hz, 1 H), 7.20 (s, 1 H), 6.97 (s, 1 H), 4.36 (br. s., 2 H), 3.23 (br. s., 4 H), 2.93-3.12 (m, 5 H), 2.24 (s, 3 H), 2.19 (s, 3 H), 1.06-1.19 ppm (m, 4 H). |

| Example | Structure | MS | ¹H NMR |
|---|---|---|---|
| 184 | Z-184 | 518.1 [M + H]⁺ | ¹H NMR (400 MHz, DMSO-d₆): δ 11.88 (br. s., 1H), 7.80 (d, J = 6.4 Hz, 1H), 7.58 (d, J = 10.4 Hz, 1H), 7.19-7.08 (m, 2H), 3.94 (s, 2H), 3.11-3.05 (m, 1H), 3.02-3.01 (m, 4H), 2.87-2.86 (m, 4H), 2.26 (d, J = 2.4 Hz, 3H), 1.16-1.11 (m, 4H). |
| 185 | Z-185 | 512.1 [M − H]⁻ | ¹H NMR (400 MHz, DMSO-d₆): δ 11.90 (br. s., 1H), 7.76 (d, J = 6.4 Hz, 1H), 7.51 (d, J = 10.8 Hz, 1H), 6.76 (s, 2H), 3.81 (s, 2H), 3.18-3.17 (m, 4H), 3.07-3.02 (m, 1H), 2.73-2.72 (m, 4H), 2.24 (s, 6H), 1.12-1.08 (m, 4H). |
| 186 | Z-186 | 518.1 [M + H]⁺ | ¹H NMR (dmso, 400 MHz): δ = 7.83 (d, J = 6.0 Hz, 1 H), 7.64 (d, J = 10.0 Hz, 1 H), 7.30 (d, J = 12.0 Hz, 1 H), 7.03 (d, J = 9.6 Hz, 1 H), 4.17 (br. s., 2 H), 3.67 (br. s., 4 H), 3.16 (br. s., 4 H), 2.94-3.12 (m, 1 H), 2.22 (s, 3 H), 1.04-1.17 ppm (m, 4 H). |
| 187 | Z-187 | 534.0 [M + H]⁺ | ¹H NMR (dmso, 400 MHz): δ = 11.88 (br. s., 1 H), 7.76 (d, J = 6.0 Hz, 1 H), 7.53 (d, J = 10.8 Hz, 1 H), 7.37 (d, J = 8.8 Hz, 1 H), 7.06 (d, J = 8.8 Hz, 1 H), 3.85 (br. s., 2 H), 2.90-3.11 (m, 5 H), 2.78 (br. s., 4 H), 2.39 (s, 3 H), 1.00-1.21 ppm (m, 4 H). |
| 188 | Z-188 | 518.0 [M + H]⁺ | ¹H NMR (400 MHz, DMSO-d₆): δ 7.80 (d, J = 6.4 Hz, 1H), 7.56 (d, J = 10.4 Hz, 1H), 7.20 (dd, J = 1.2, 8.8 Hz, 1H), 6.93 (t, J = 8.8 Hz, 1H), 3.88 (s, 2H), 3.10-3.07 (m, 5H), 2.82-2.80 (m, 4H), 2.23 (d, J = 2.4 Hz, 3H), 1.16-1.11 (m, 4H). |

Example 189: Preparation of N-(cyclopropylsulfonyl)-5-ethyl-2-fluoro-4-((4-(4-(trifluoromethoxy)phenyl)piperazin-1-yl)methyl)benzamide (Z-189)

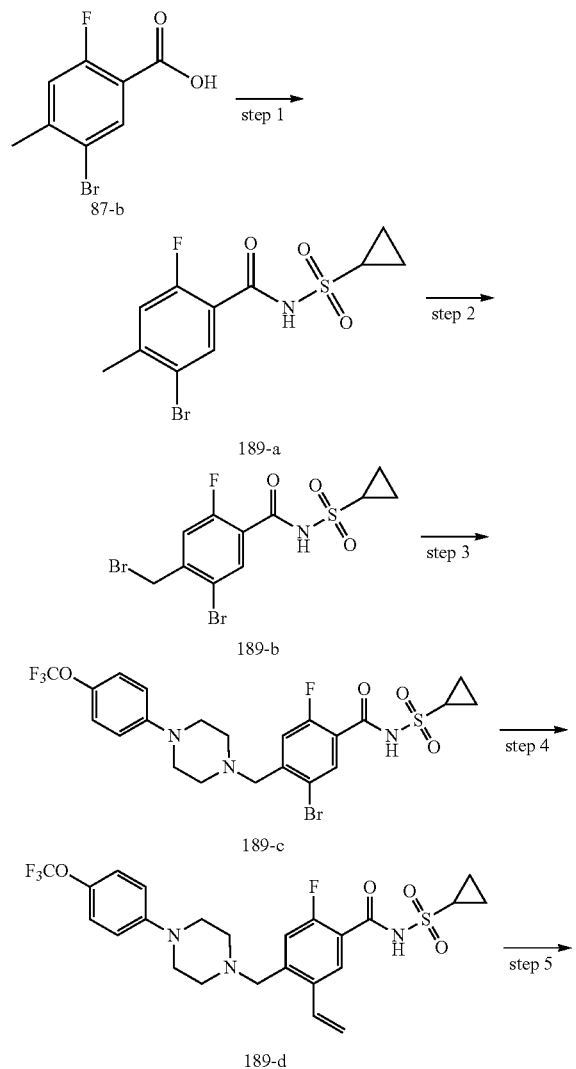

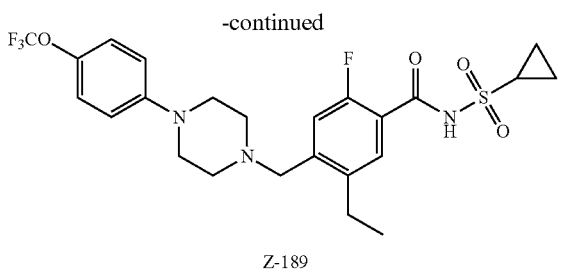

Step 1: Compound 189-a was obtained according to the preparation method of step 1 in Example 89 using compound 87-b as a starting material.

Step 2: Compound 189-b was obtained according to the preparation method of step 2 in Example 89 using compound 189-a as a starting material.

Step 3: Compound 189-c was obtained according to the preparation method of step 3 in Example 89 using compound 189-b as a starting material.

Step 4: A mixed solution of compound 189-c, potassium vinyltrifluoroborate, Pd(dppf)Cl$_2$, triethylamine in ethanol was stirred under argon at 90° C. for 6 h. The reaction solution was cooled to room temperature, filtered through celite, and the filtrate was concentrated to give the crude 189-d which was used directly in the next reaction.

Step 5: Palladium on carbon was added to a solution of compound 189-d in methanol, and the reaction solution was stirred under hydrogen atmosphere at room temperature overnight. The reaction solution was filtered through celite, and the filtrate was concentrated under reduced pressure and purified by Pre-HPLC to give a white solid compound Z-189 (39.12 mg), purity 100%, yield 10%, MS m/z(ESI): 529.9 [M+H]$^+$. $^1$H NMR (400 MHz, DMSO-d6): δ 12.1 (br.s., 1H), 7.48 (d, J=7.2 Hz, 1H), 7.28 (d, J=11.6 Hz, 1H), 7.19 (d, J=8.8 Hz, 2H), 7.00 (d, J=9.2 Hz, 2H), 3.59 (s, 2H), 3.20-3.16 (m, 4H), 3.11-3.05 (m, 1H), 2.70 (q, J=7.6 Hz, 2H), 2.60-2.56 (m, 4H), 1.18 (t, J=7.6 Hz, 3H), 1.13-1.08 (i, 4H).

Examples 190-193

Compounds Z-190 to Z-193 were prepared according to the method of steps 3-5 in Example 189 using compound 189-b as a starting material, except that the palladium on carbon in step 5 was changed to platinum dioxide in the preparation of Z-191 to Z-193.

| Example | Structure | MS | $^1$H NMR |
|---|---|---|---|
| 190 | Z-190 | 513.9 [M + H]$^+$ | $^1$H NMR (400 MHz, DMSO-d$_6$): δ 7.51-7.47 (m, 3H), 7.19 (d, J = 11.6 Hz, 1H), 7.06 (d, J = 9.2 Hz, 2H), 3.55 (s, 2H), 3.30-3.27 (m, 4H), 3.02-2.98 (m, 1H), 2.68 (q, J = 7.6 Hz, 2H), 2.56-2.53 (m, 4H), 1.17 (t, J = 7.2 Hz, 3H), 1.02-0.94 (m, 4H). |

-continued

| Example | Structure | MS | ¹H NMR |
|---|---|---|---|
| 191 | Z-191 | 513.9 [M + H]⁺ | ¹H NMR (400 MHz, DMSO-d₆): δ 12.04 (br. s., 1H), 7.48 (d, J = 7.2 Hz, 1H), 7.39 (d, J = 9.2 Hz, 1H), 7.25 (d, J = 11.6 Hz, 1H), 7.12 (d, J = 2.4 Hz, 1H), 6.93 (dd, J = 2.8, 8.8 Hz, 1H), 3.57 (s, 2H), 3.21-3.18 (m, 4H), 3.09-3.02 (m, 1H), 2.69 (q, J = 7.2 Hz, 2H), 2.55-2.51 (m, 4H), 1.18 (t, J = 7.6 Hz, 3H), 1.09-1.04 (m, 4H). |
| 192 | Z-192 | 513.8 [M + H]⁺ | ¹H NMR (400 MHz, DMSO-d₆): δ 12.00 (br. s., 1H), 7.48 (d, J = 7.2 Hz, 1H), 7.29 (d, J = 11.2 Hz, 1H), 6.94 (d, J = 1.6 Hz, 2H), 6.85 (s, 1H), 3.59 (s, 2H), 3.26-3.23 (m, 4H), 3.12-3.05 (m, 1H), 2.69 (q, J = 7.2 Hz, 2H), 2.55-2.51 (m, 4H), 1.18 (t, J = 7.2 Hz, 3H), 1.15-1.09 (m, 4H). |
| 193 | Z-193 | 497.9 [M + H]⁺ | ¹H NMR (400 MHz, DMSO-d₆): δ 7.58 (d, J = 5.6 Hz, 1H), 7.48 (br. s., 1H), 7.39 (t, J = 8.8 Hz, 1H), 7.04 (d, J = 13.2 Hz, 1H), 6.82 (d, J = 7.2 Hz, 1H), 3.70-3.54 (m, 10H), 3.13-3.08 (m, 1H), 2.75 (q, J = 7.2 Hz, 2H), 1.19-1.13 (m, 7H). |

Example 194: Preparation of N-(cyclopropylsulfonyl)-5-ethyl-2-fluoro-4-((4-(5-(trifluoromethoxy)pyridin-2-yl)piperazin-1-yl)methyl)benzamide (Z-194)

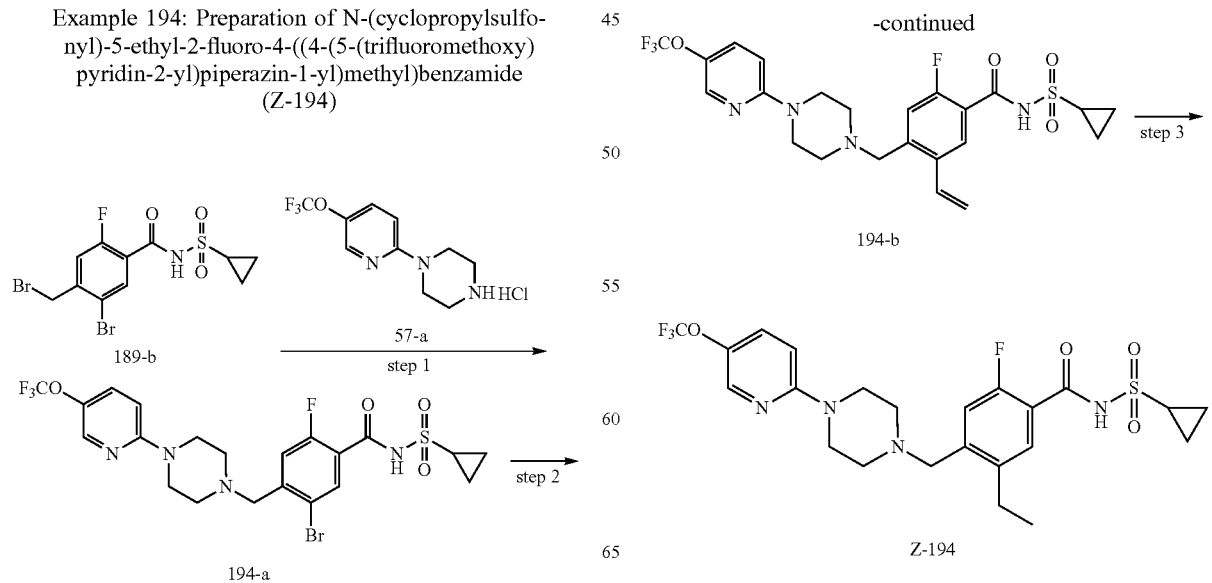

Step 1: Compound 194-a was obtained according to the preparation method of step 3 in Example 189 using compound 57-a as a starting material.

Step 2: Compound 194-b was obtained according to the preparation method of step 4 in Example 189 using compound 194-a as a starting material.

Step 3: Compound Z-194 was obtained according to the preparation method of step 5 in Example 189 using compound 194-b as a starting material. MS m/z(ESI): 513.2 [M+H]$^+$. $^1$H NMR (400 MHz, DMSO-d6): δ 12.02 (s, 1H), 8.15 (d, J=2.4 Hz, 1H), 7.60 (dd, J1=9.2 Hz, J2=2.0 Hz, 1H), 7.48 (d, J=7.2 Hz, 1H), 7.29 (d, J=11.6 Hz, 1H), 6.91 (d, J=9.2 Hz, 1H), 3.58 (s, 2H), 3.53 (m, 4H), 3.04-3.11 (m, 1H), 2.67-2.73 (q, J=7.2 Hz, 2H), 2.49-2.50 (m, 4H), 1.18 (t, J=7.6 Hz, 3H), 1.09-1.12 (m, 4H).

Example 195: Preparation of (R)—N-(cyclopropyl)-2-fluoro-5-methyl-4-((1-(5-(trifluoromethyl)pyridin-2-yl)pyrrolidin-2-yl)methoxy)benzamide (Z-195)

Step 1: Compound 195-b (440 mg was obtained as a white solid according to the preparation method of step 3 in Example 125 using compound 142-a(520 mg, 1.09 mmol) as a starting material, except that the cyclopropyl boronic acid was replaced by methyl boric acid, purity 100%, yield 98%, MS m/z(ESI): 413.2 [M+H]$^+$.

Step 2: Compound 195-c (420 mg) was obtained as a white solid according to the preparation method of step 4 in Example 125 using compound 195-b(440 mg, 1.07 mmol) as a starting material, purity 92%, yield 98%, MS m/z(ESI): 399.2[M+H]$^+$.

Step 3: Compound Z-195 (25.75 mg) was obtained as a white solid according to the preparation method of step 5 in Example 125 using compound 195-c(100 mg, 0.25 mmol) as a starting material, purity 100%, yield 21%, MS m/z(ESI): N/A. $^1$H NMR DMSO-d$_6$, 400 MHz): δ 11.78 (br. s., 1H), 8.38 (s, 1H), 7.77 (dd, J=9.2, 2.4 Hz, 1H), 7.46 (d, J=8.4 Hz, 1H), 7.07 (d, J=12.8 Hz, 1H), 6.68 (d, J=9.2 Hz, 1H), 4.51 (br. s., 1H), 4.14-4.28 (m, 1H), 4.01-4.06 (m, 1H), 3.48-3.61 (m, 1H), 3.30-3.39 (m, 1H), 2.96-3.06 (m, 1H), 1.91-2.21 (m, 7H), 0.94-1.15 ppm (m, 4H).

Example 196: Preparation of (cyclopropylsulfonyl)-4-((4-(3,4-dichlorophenyl) piperazin-1-yl)methyl)-2-fluorobenzamide (Z-196)

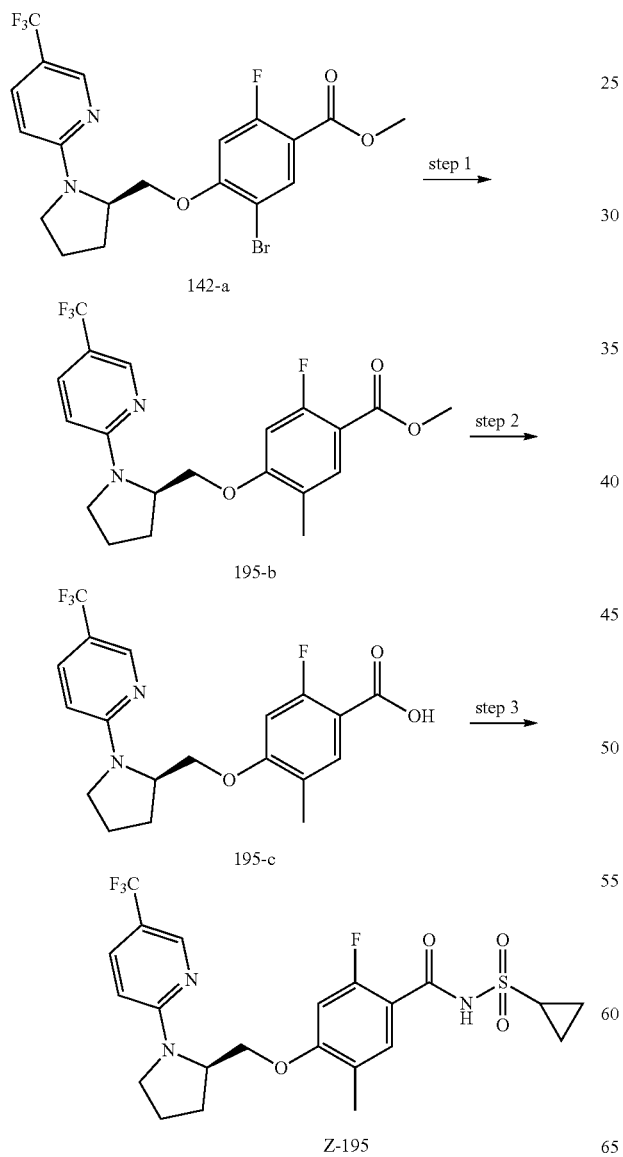

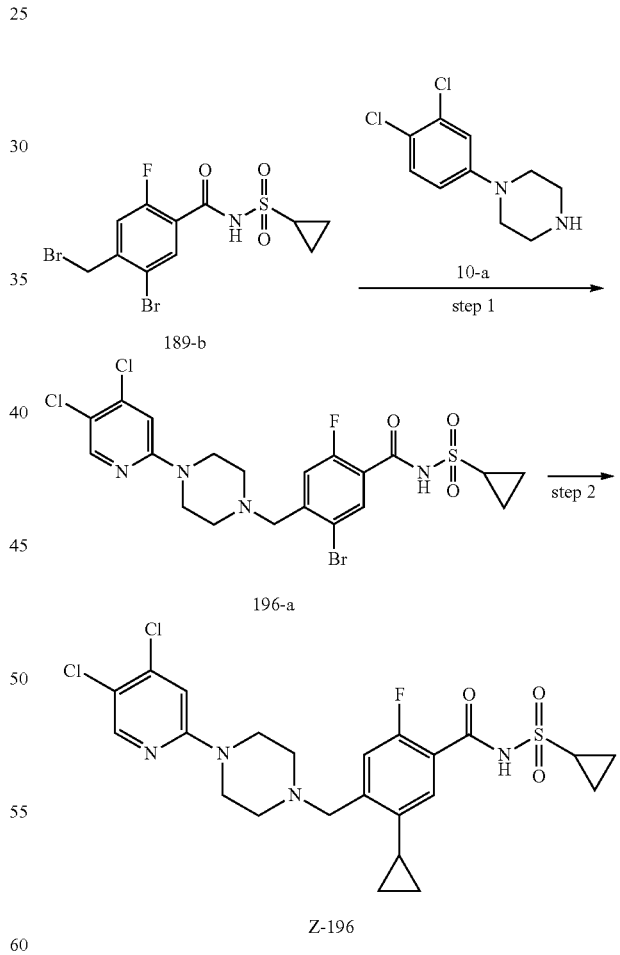

Step 1: Compound 196-a was obtained according to the preparation method of step 3 in Example 89 using compound 189-b as a starting material.

Step 2: Compound Z-196 was obtained according to the preparation method of step 3 in Example 125 using compound 196-a as a starting material.

MS m/z(ESI): NA. ¹H NMR (400 MHz, DMSO-d6): δ 11.96 (br. s., 1H), 7.36 (d, J=8.8 Hz, 1H), 7.27 (d, J=11.6 Hz, 1H), 7.20 (d, J=6.8 Hz, 1H), 7.10 (d, J=2.8 Hz, 1H), 6.90 (dd, J=2.8, 8.8 Hz, 1H), 3.73 (s, 2H), 3.22-3.18 (m, 4H), 3.07-3.02 (m, 1H), 2.58-2.54 (m, 4H), 2.10-2.02 (m, 1H), 1.10-1.06 (m, 4H), 0.94-0.88 (m, 2H), 0.68-0.63 (m, 2H).

Example 197: Preparation of (cyclopropylsulfonyl)-4-((4-(3,5-dichlorophenyl) piperazin-1-yl)methyl)-2-fluorobenzamide (Z-197)

Comparative Example 1: Preparation of 5-(cyclopropylsulfonyl)-4-((4-(3,5-dichlorobenzyl)piperazin-1-yl)methyl)-2-fluorobenzamide (C 1)

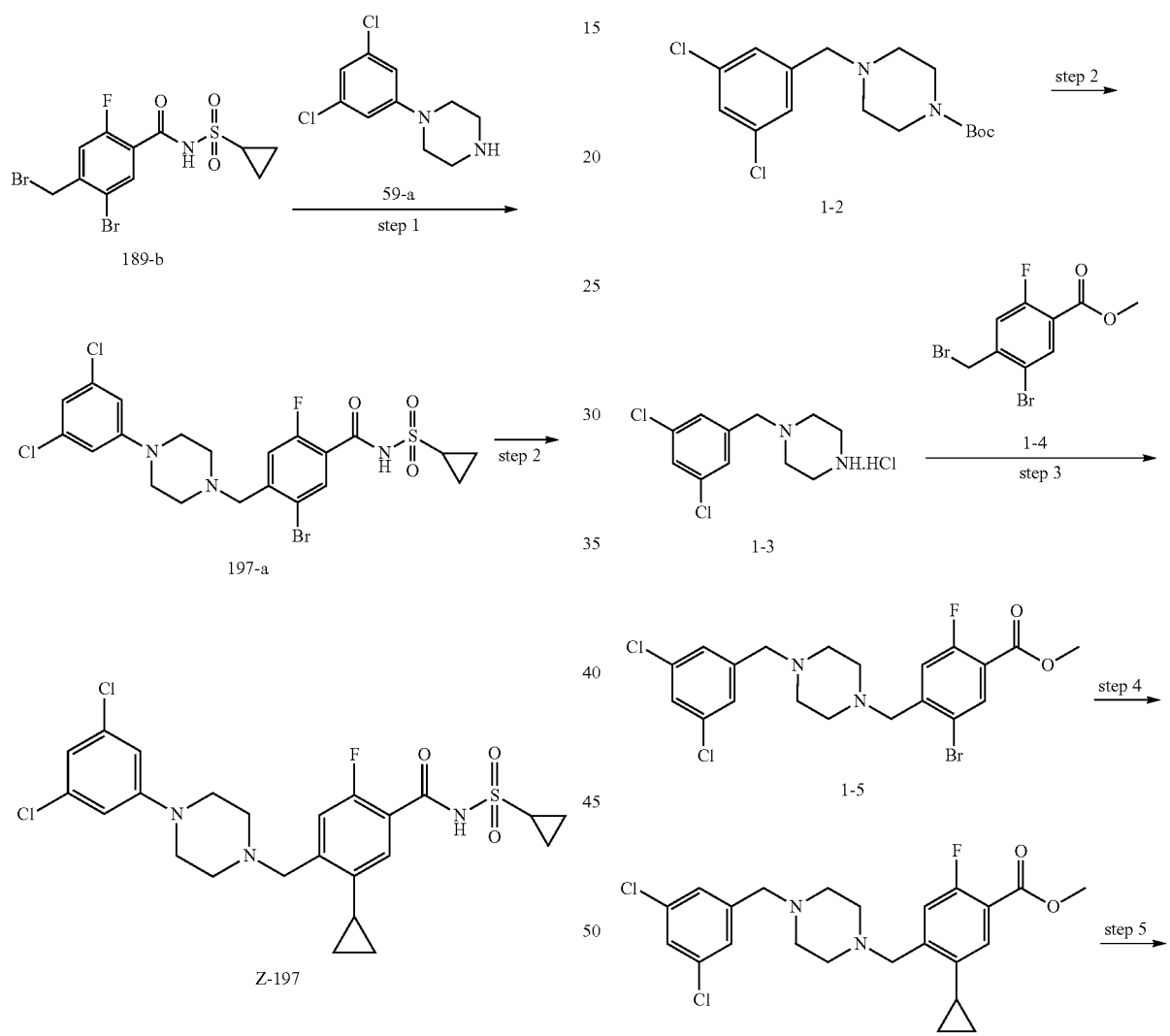

Step 1: Compound 197-a was obtained according to the preparation method of step 3 in Example 89 using 189-b as a starting material, except that compound 10-a was replaced by compound 59-a.

Step 2: Compound Z-197 was obtained according to the preparation method of step 3 in Example 125 using 197-a as a starting material, MS m/z(ESI): NA. ¹H NMR (400 MHz, DMSO-d6): δ 12.03 (br. s., 1H), 7.26-7.22 (m, 2H), 6.94 (d, J=1.6 Hz, 2H), 6.86 (t, J=1.6 Hz, 1H), 3.71 (s, 2H), 3.27-3.24 (m, 4H), 3.05-3.00 (m, 1H), 2.57-2.53 (m, 4H), 2.10-2.05 (m, 1H), 1.05-0.97 (m, 4H), 0.96-0.91 (m, 2H), 0.67-0.63 (m, 2H).

-continued

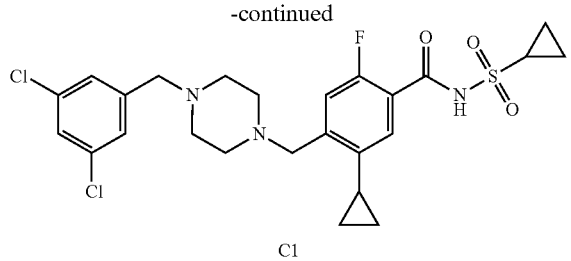

Step 1: A mixed solution of compound 1-1 (1.96 g, 10.0 mmol), N-Boc-piperazine (1.95 g, 10.5 mmol), potassium carbonate (2.76 g, 20.0 mmol) in acetonitrile (20 ml) was stirred at 80° C. for 16 h. The reaction mixture was cooled to room temperature, the solvent was removed under reduced pressure, water was added, and the mixture was extracted with ethyl acetate (2*50 ml). The organic phase was washed with saturated brine (30 ml), dried and separated, and the filtrate was concentrated under reduced pressure to give compound 1-2 (3.5 g) as a yellow oil, purity 90.26%, yield 100%. MS m/z(ESI): 345.0[M+H]$^+$.

Step 2: To a solution of compound 1-2 in methanol (50 ml) was added hydrochloric acid solution (10 ml, 40.58 mmol). The mixture was stirred at room temperature for 16 h and concentrated under reduced pressure to give compound 1-3 (2.9 g) as a yellow solid, purity 91.49%, yield 100%. MS m/z(ESI): 245.0[M+H]$^+$.

Step 3: A mixed solution of compound 1-3 (2.9 g, 10.28 mmol), compound 1-4 (3.35 g, 10.28 mmol), potassium carbonate (2.84 g, 20.56 mmol) in acetonitrile(50 ml) was stirred at 80° C. for 16 h. The reaction solution was cooled to room temperature, the solvent was removed under reduced pressure, water was added and the mixture was extracted with ethyl acetate (2*50 ml). The organic phase was washed with saturated brine (30 ml), dried and separated, and the filtrate was concentrated under reduced pressure to give the crude which was purified by column chromatography to give compound 1-5 (2.6 g) as a yellow oil, purity 100%, yield 51.7%, MS m/z(ESI): 491.0[M+H]$^+$.

Step 4: A solution of compound 1-5 (1.0 g, 2.04 mmol), cyclopropyl boronic acid (0.35 g, 4.08 mmol), Pd(dppf)Cl2 (149 mg, 0.204 mmol), cesium carbonate (1.33 g, 4.08 mmol) in dioxane (10 ml) was stirred under argon at 80° C. for 16 h. The reaction solution was cooled to room temperature and the solid was removed by filtration. The filter cake was washed with ethyl acetate, and the filtrate was concentrated under reduced pressure to give a colorless oil compound 1-6 (130 mg), purity 97.42%, yield 14.1%, MS m/z(ESI): 451.0[M+H]$^+$.

Step 5: To a solution of compound 1-6 (130 mg, 0.265 mmol) in methanol (10 ml) was added sodium hydroxide solution (5 M, 2 ml) and the mixture was stirred at 60° C. for 2 h. Most of the solvent was removed under reduced pressure, and the residue was dissolved in water. The pH value was adjusted to about 7 with 1N hydrochloric acid solution and the reaction mixture was extracted with ethyl acetate (2*10 ml). The organic phase was washed with saturated brine (10 ml), dried and concentrated to give a colorless oil compound 1-7 (110 mg), purity 97.7%, yield 94.8%, MS m/z(ESI): 437.0[M+H]$^+$.

Step 6: A mixed solution of compound 1-7 (110 mg, 0.252 mmol), cyclopropylsulfonamide (46 mg, 0.378 mmol), EDCI (97 mg, 0.504 mmol), DMAP (31 mg, 0.252 mmol), DIPEA(98 mg, 0.756 mmol) in dichloromethane (5 ml) was stirred at room temperature for 20 h. The reaction solution was diluted with dichloromethane, washed with water and saturated brine, and the organic phase was dried and concentrated to give a white solid compound C1 (35 mg), purity 100%, yield 25.7%, MS m/z(ESI): 540.1[M+H]$^+$. $^1$H NMR (dmso, 400 MHz): δ 12.10 (br. s., 1H), 7.66 (br. s., 1H), 7.52 (br. s., 2H), 7.34 (d, J=10.8 Hz, 1H), 7.21 (d, J=7.2 Hz, 1H), 4.13 (br. s., 4H), 2.84-3.32 (m, 9H), 2.01-2.12 (m, 1H), 1.04-1.15 (m, 4H), 0.87-0.97 (m, 2H), 0.65-0.72 ppm (m, 2H)

Comparative Example 2, 11

Compound C2 was prepared according to the preparation method of comparative example 1 using 3,4-dichlorobenzylbromide as a starting material, except that the cyclopropylsulfonamide in step 6 was replaced by methanesulfonamide.

Compound C11 was prepared according to the preparation method of comparative example 1, except that the cyclopropylsulfonamide in Step 6 was replaced by methanesulfonamide.

| Comparative Example | Structure | MS m/z (ESI) | $^1$H NMR |
|---|---|---|---|
| C2 | (structure: 3,4-dichlorobenzyl piperazine linked compound) | 514.2 [M + H]$^+$ | $^1$H NMR (DMSO-d6, 400 MHz): δ 11.29 (br. s., 1 H), 7.49-7.64 (m, 2 H), 7.30 (d, J = 8.0 Hz, 1 H), 7.05-7.25 (m, 2 H), 3.72 (s, 2 H), 3.62 (s, 2 H), 3.16 (s, 3 H), 2.55 (br. s., 8 H), 1.92-2.09 (m, 1 H), 0.85-0.93 (m, 2 H), 0.57-0.65 ppm (m, 2 H). |
| C11 | (structure: 3,5-dichlorobenzyl piperazine linked compound) | 514.2 [M + H]$^+$ | $^1$H NMR (400 MHz, DMSO-d6): δ 11.45 (br. s., 1H), 7.53 (t, J = 1.6 Hz, 1H), 7.39 (d, J = 2.0 Hz, 2H), 7.22 (dd, J = 7.2, 11.6 Hz, 2H), 3.76 (s, 2H), 3.62 (s, 2H), 3.34-3.31 (m, 4H), 3.20 (s, 3H), 2.58-2.54 (m, 4H), 2.09-2.00 (m, 1H), 0.96-0.90 (m, 2H), 0.67-0.63 (m, 2H). |

Comparative example 4: Preparation of 5-chloro-4-((4-(4-chloro-3-methylbenzyl) piperazin-1-yl) methyl)-N-(cyclopropylsulfonyl)-2-fluorobenzamide (C4)

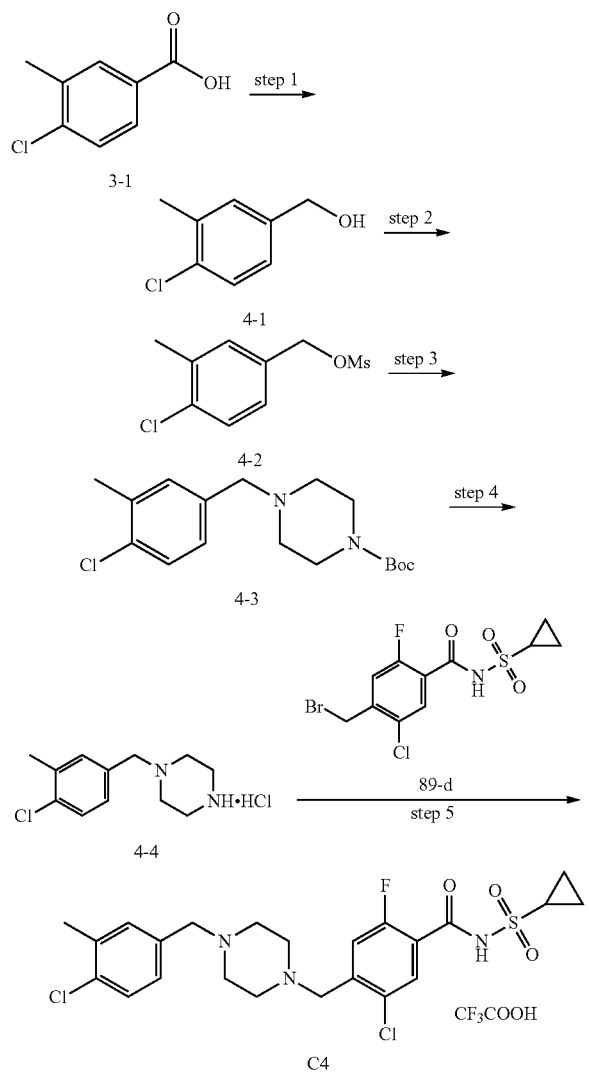

Step 1: A solution of borane in tetrahydrofuran (1M, 5.9 ml) was added dropwise to a solution of compound 3-1 (1 g, 5.85 mmol) in tetrahydrofuran, and the reaction solution was stirred at room temperature for 16 h. To the reaction solution was added methanol to quench the reaction, and concentrated under reduced pressure. The crude product was purified by column chromatography (PE:EA=7:3) to give compound 4-1 (910 mg) as a pale yellow solid, purity 100%, yield 99%, MS m/z(ESI): N/A.

Step 2: To a mixed solution of compound 4-1 (650 mg, 4.14 mmol) and DIPEA (1.07 g, 8.28 mmol) in dichloromethane was added a solution of methylsulfonyl chloride (524 mg, 4.55 mmol) in dichloromethane dropwise, and the reaction solution was stirred at room temperature for 16 h. The reaction solution was washed with 2N hydrochloric acid and saturated brine, dried and concentrated to give compound 4-2 (780 mg) as a brown oil, purity 97%, yield 80%, MS m/z(ESI): N/A.

Step 3: Compound 4-3 (950 mg) was obtained as a yellow oil according to the preparation method of step 1 in comparative example 1 using compound 4-2 as a starting material, purity 100%, yield 88%, MS m/z(ESI): 325.0[M+H]$^+$.

Step 4: Compound 4-4 (750 mg) was obtained as a white solid according to the preparation method of step 2 in comparative example 1 using compound 4-3 as a starting material, purity 100%, yield 95%, MS m/z(ESI): 225.0[M+H]$^+$.

Step 5: Compound C4 (140 mg) was obtained as a white solid according to the preparation method of step 3 in comparative example 1 using compound 4-4 as a starting material, purity 100%, yield 70%, MS m/z(ESI): 513.8[M+H]$^+$. $^1$H NMR (dmso, 400 MHz): δ 12.32 (br. s., 1H), 9.79 (br. s., 1H), 7.74 (d, J=6.4 Hz, 1H), 7.40-7.55 (m, 3H), 7.32 (d, J=8.0 Hz, 1H), 4.26 (br. s., 2H), 3.94 (br. s., 4H), 3.69 (br. s., 2H), 3.26 (br. s., 2H), 2.97-3.18 (m, 1H), 2.92 (br. s., 2H), 2.33 (s, 3H), 1.03-1.18 ppm (m, 4H).

Comparative Examples 3, 5, 6, 12, 13

Compounds C3 and C5 were prepared according to the preparation method of step 5 in comparative example 4 using 62-a and 63-a as starting materials respectively.

Compound C6 was prepared according to the preparation method of comparative example 4 using 4-chlorobenzoic acid as a starting material.

Compound C12, C13 were prepared according to the preparation method of step 5 in comparative example 4 using corresponding phenyl substituted piperazine as starting materials, except that compound 89-d was replaced by 13-a.

| Comparative Example | Structure | MS m/z (ESI) | $^1$H NMR |
|---|---|---|---|
| C3 | 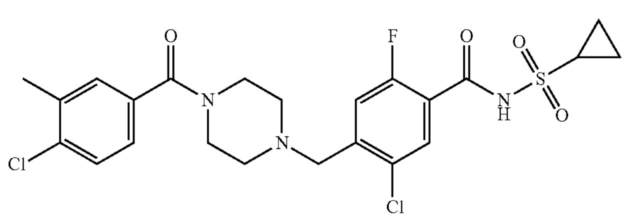 [SMILES: Cc1cc(C(=O)N2CCN(Cc3cc(F)c(C(=O)NS(=O)(=O)C4CC4)cc3Cl)CC2)ccc1Cl] | 527.8 [M + H]$^+$ | $^1$H NMR (dmso, 400 MHz): δ 7.82 (br. s., 1 H), 7.62 (br. s., 1 H), 7.48 (d, J = 8.4 Hz, 1 H), 7.40 (s, 1 H), 7.26 (d, J = 8.4 Hz, 1 H), 4.14 (br. s., 2 H), 3.50 (br. s., 4 H), 3.05-3.11 (m, 1 H), 2.96 (br. s., 4 H), 2.34 (s, 3 H), 1.04-1.20 (m, 4 H). |

| Comparative Example | Structure | MS m/z (ESI) | ¹H NMR |
|---|---|---|---|
| C5 | 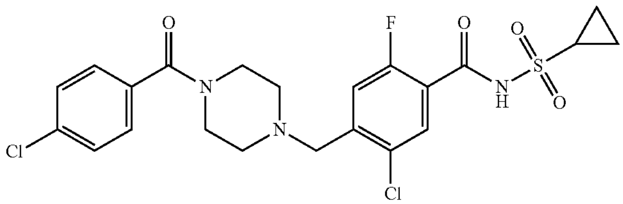 [SMILES: O=C(NS(=O)(=O)C1CC1)c1cc(Cl)c(CN2CCN(C(=O)c3ccc(Cl)cc3)CC2)cc1F] | 513.8 [M + H]+ | ¹H NMR (dmso, 400 MHz): δ 12.21 (br. s, 1 H), 7.71 (d, J = 6.4 Hz, 1 H), 7.34-7.52 (m, 5 H), 3.63 (s, 2 H), 3.29 (br. s., 4H), 2.96-3.09 (m, 1 H), 2.47 (br. s., 4H), 0.99-1.13 ppm (m, 4 H). |
| C6 | 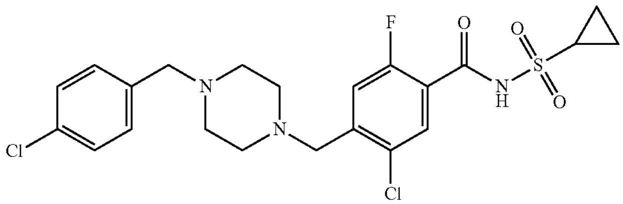 [SMILES: O=C(NS(=O)(=O)C1CC1)c1cc(Cl)c(CN2CCN(Cc3ccc(Cl)cc3)CC2)cc1F] | 499.8 [M + H]+ | ¹H NMR (dmso, 400 MHz): δ 12.39 (br. s., 1 H), 7.75-7.85 (m, 2 H), 7.65 (d, J = 8.4 Hz, 2 H), 7.50 (d, J = 8.4 Hz, 2 H), 4.34 (br. s., 2 H), 4.13 (br. s., 2 H), 3.15-3.33 (m, 8 H), 2.94-3.09 (m, 1 H), 0.96-1.18 ppm (m, 4 H). |
| C12 | 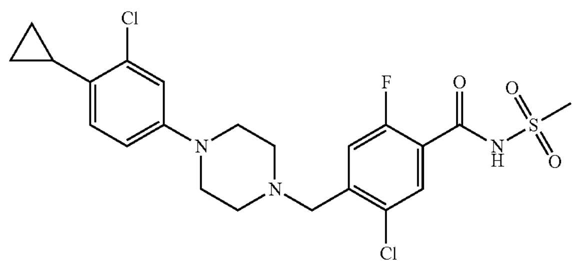 [SMILES: CS(=O)(=O)NC(=O)c1cc(Cl)c(CN2CCN(c3ccc(C4CC4)c(Cl)c3)CC2)cc1F] | 500.1 [M + H]+ | ¹H NMR (400 MHz, DMSO-$d_6$): δ 7.73 (d, J = 6.4 Hz, 1H), 7.41 (d, J = 10.8 Hz, 1H), 6.91 (d, J = 2.4 Hz, 1H), 6.84 (d, J = 8.8 Hz, 1H), 6.79 (dd, J = 2.4 Hz, 8.8 Hz, 1H), 3.67 (s, 2H), 3.20 (s, 3H), 3.16-3.10 (m, 4H), 2.66-2.55 (m, 4H), 1.99-1.92 (m, 1H), 0.89-0.83 (m, 2H), 0.57-0.52 (m, 2H). |
| C13 | 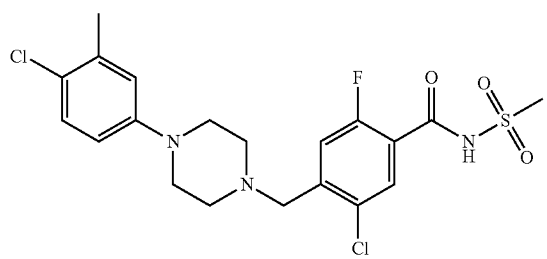 [SMILES: Cc1cc(N2CCN(Cc3cc(F)c(C(=O)NS(C)(=O)=O)cc3Cl)CC2)ccc1Cl] | 474.1 [M + H]+ | ¹H NMR (400 MHz, DMSO-$d_6$): δ 12.06-12.00 (m, 1H), 7.75 (d, J = 6.4 Hz, 1H), 7.46 (d, J = 10.8 Hz, 1H), 7.16 (d, J = 8.8 Hz, 1H), 6.90 (d, J = 2.8 Hz, 1H), 6.75 (dd, 3.2 Hz, 8.8 Hz, 1H), 3.73 (s, 2H), 3.26 (s, 3H), 3.17-3.14 (m, 4H), 2.67-2.64 (m, 4H), 2.23 (s, 3H). |

Comparative Example 7: Preparation of (R)-5-chloro-4-((1-(4-chlorobenzyl) pyrrolidin-2-yl)methoxy)-N-(cyclopropylsulfonyl) (C7)

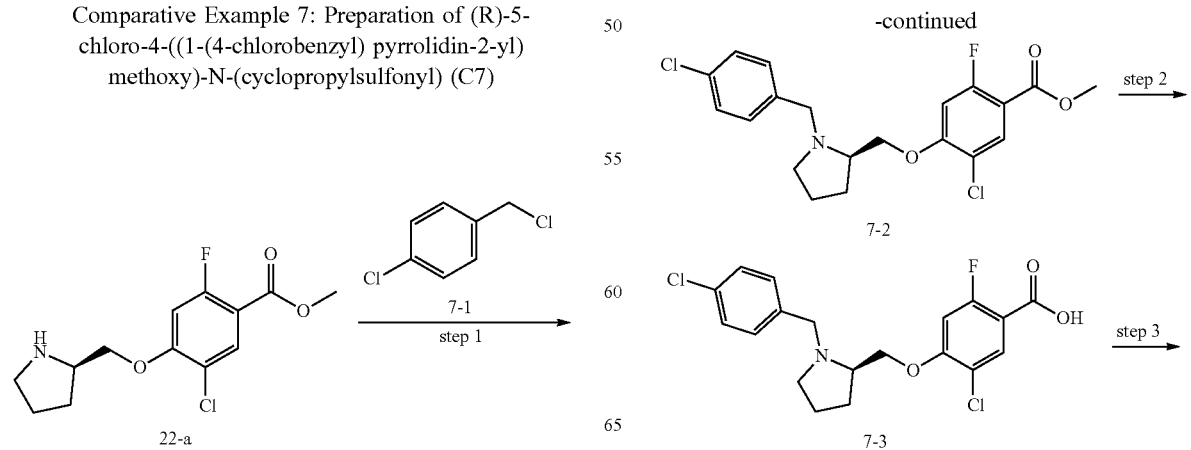

-continued

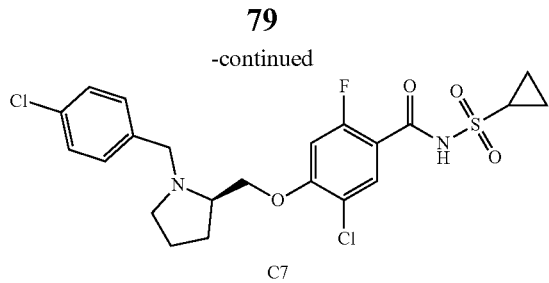

C7

Step 1: A mixed solution of compound 22-a (75 mg, 0.463 mmol), compound 7-1 (150 mg, 0.463 mmol), potassium carbonate (192 mg, 1.388 mmol) in acetonitrile was stirred at 80° C. for 3 h. The reaction solution was cooled to room temperature. The reaction mixture was poured into water and extracted with ethyl acetate. The organic phase was dried and concentrated to give compound 7-2 (165 mg) as a yellow oil, purity 84.4%, yield 87%, MS m/z(ESI): 412.2 [M+H]$^+$.

Step 2: Sodium hydroxide solution (2 M, 0.8 ml) was added to a solution of compound 7-2 in methanol, and the mixture was stirred at room temperature for 3 h. The reaction solution was concentrated under reduced pressure, the residue was dissolved in water. The pH was adjusted to 1-2 with 1M hydrochloric acid solution, the reaction mixture was filtered and the filter cake was washed with water, dried to give compound 7-3 (121 mg) as a white solid, purity 95.33%, yield 76%, MS m/z(ESI): 398.1[M+H]$^+$.

Step 3: Compound C7 (19 mg) was obtained as a white solid according to the preparation method of step 6 in comparative example 2 using compound 7-3 as a starting material, MS m/z(ESI): 500.9[M+H]$^+$. $^1$H NMR (400 MHz, DMSO-d6): δ 12.06 (br. s., 1H), 7.81 (d, J=7.2 Hz, 1H), 7.57-7.51 (m, 4H), 7.29 (d, J=12.0 Hz, 1H), 4.72-4.68 (m, 1H), 4.49-4.45 (m, 1H), 4.40-4.35 (m, 2H), 4.08 (br. s., 1H), 3.26-3.23 (m, 2H), 3.08-3.03 (m, 1H), 2.31-2.26 (m, 1H), 2.04 (br. s., 1H), 1.94-1.79 (m, 2H), 1.13-1.08 (m, 4H).

Comparative Example 8: Preparation of (R)-5-chloro-N-(cyclopropylsulfonyl)-2-fluoro-4-((1-(4-(trifluoromethyl)benzyl)pyrrolidin-2-yl)methoxy) (C8)

-continued

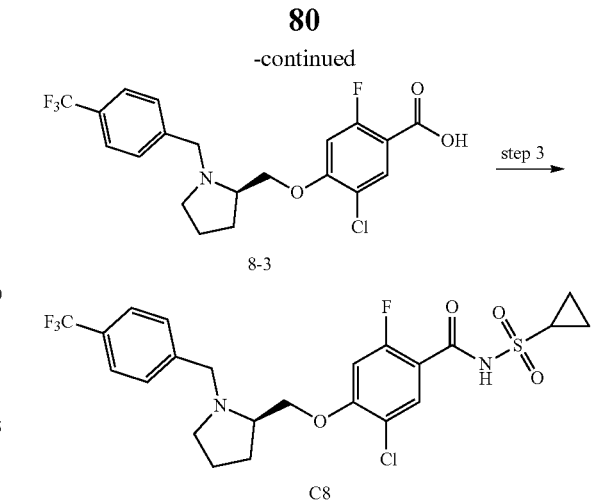

Compound C8 (48 mg) was obtained as a white solid according to the preparation method of comparative example 7 using compound 8-1 as a starting material, MS m/z(ESI): 534.9 [M+H]$^+$. $^1$H NMR (400 MHz, DMSO-d6): δ 12.09 (br. s., 1H), 7.84-7.74 (m, 5H), 7.30 (d, J=12.0 Hz, 1H), 4.80-4.77 (in, 1H), 4.50-4.38 (m, 3H), 4.10-4.08 (n, 1H), 3.26-3.24 (in, 2H), 3.09-3.02 (m, 1H), 2.32-2.29 (i, 1H), 2.05-2.03 (m, 1H), 1.92-1.80 (m, 2H), 1.13-1.08 (m, 4H).

Comparative Example 9: Preparation of (R)-5-chloro-4-((1-(4-chlorobenzoyl) pyrrolidin-2-yl)methoxy)-N-(cyclopropylsulfonyl)(C9)

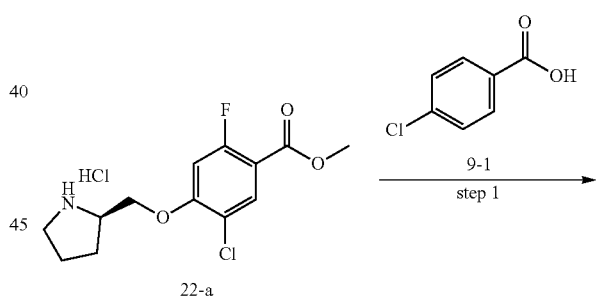

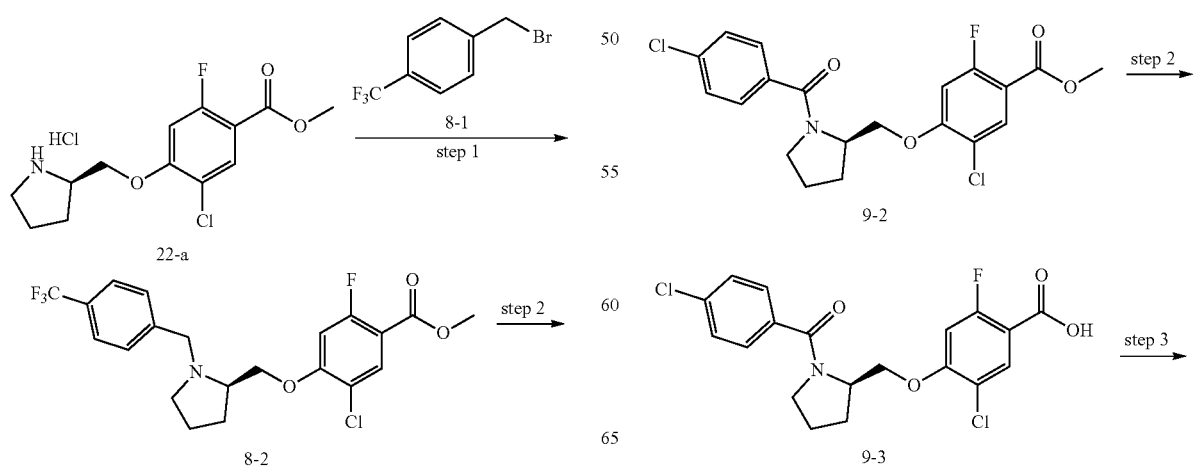

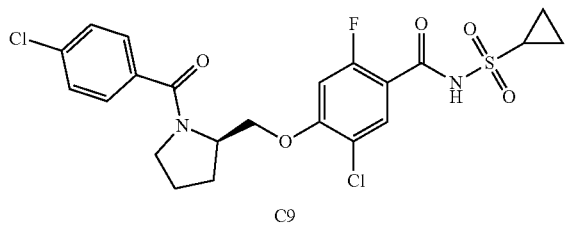

C9

Step 1: A solution of compound 9-1 (100 mg, 0.639 mmol) in thionyl chloride (2 ml) was stirred at 80° C. for 3 h. The reaction solution was cooled to room temperature and concentrated under reduced pressure to remove the solvent. The residue was dissolved in dichloromethane(10 ml). Compound 22-a (207 mg, 0.639 mmol) and triethylamine (291 mg, 1.916 mmol) were added. The reaction mixture was stirred at room temperature for 4 h, the reaction mixture was washed with 1 M hydrochloric acid and saturated brine, and the organic phase was dried and concentrated to give compound 9-2 (228 mg) as a yellow oil, purity 92.16%, yield 84%, MS m/z(ESI): 426.1[M+H]$^+$.

Step 2: Compound 9-3 (178 mg) was obtained as a white solid according to the preparation method of step 2 in comparative example 7 using compound 9-2 (228 mg, 0.535 mmol) as a starting material, MS m/z(ESI): 412.0[M+H]$^+$.

Step 3: Compound C9 (23 mg) was obtained as a white solid according to the preparation method of step 6 in comparative example 2 using compound 9-3 (100 mg, 0.242 mmol) as a starting material, MS m/z(ESI): 515.0[M+H]$^+$. $^1$H NMR (400 MHz, DMSO-d6): δ 12.05 (br. s., 1H), 7.78 (d, J=7.2 Hz, 1H), 7.52-7.46 (m, 4H), 7.37 (d, J=12.4 Hz, 1H), 4.48-4.46 (m, 1H), 4.38-4.37 (m, 2H), 3.42-3.35 (m, 2H), 3.09-3.04 (m, 1H), 2.17-2.09 (m, 1H), 2.03-1.95 (m, 2H), 1.80-1.74 (m, 1H), 1.14-1.10 (m, 4H).

Comparative Example 10: Preparation of (R)-5-chloro-N-(cyclopropylsulfonyl)-2-fluoro-4-((1-(4-(trifluoromethyl)benzoyl)pyrrolidin-2-yl)methoxy) (C10)

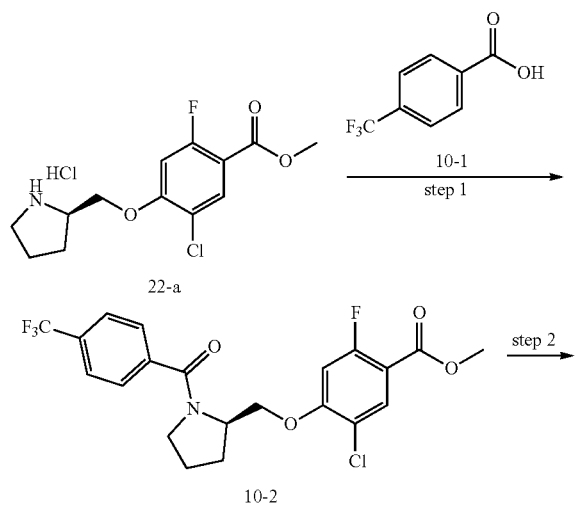

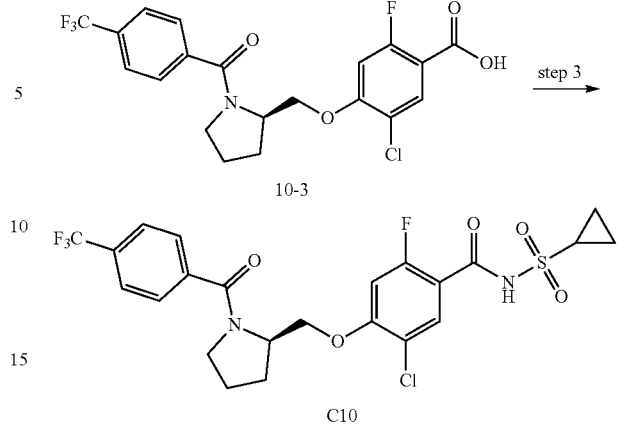

C10

Compound C10 (13 mg) was obtained as a white solid according to the preparation method of comparative example 9 using compound 10-1 (110 mg, 0.247 mmol) as a starting material, MS m/z(ESI): 549.0[M+H]$^+$. $^1$H NMR (400 MHz, DMSO-d6): δ 12.04 (br. s., 1H), 7.81-7.75 (m, 3H), 7.65-7.62 (m, 2H), 7.36 (d, J=12.8 Hz, 1H), 4.48-4.46 (m, 1H), 4.39-4.37 (m, 2H), 3.48-3.44 (m, 2H), 3.06-3.03 (m, 1H), 2.14-2.11 (m, 1H), 2.01-1.96 (m, 2H), 1.80-1.75 (m, 1H), 1.12-1.08 (m, 4H).

Assay 1: Manual Patch Clamp Experiment of Sodium Ion (hNav1.7, hNav1.5 and hNaV1.8) and Calcium Ion (hCav3.2) Channels hNav1.7, hNav1.5 Manual Patch Clamp Experiment:

Patch voltage clamp electrophysiology allows for the direct measurement and quantification of current block of voltage-gated sodium channels (NaV's), and allows the determination of the time and voltage-dependence of block which has been interpreted as differential binding to the resting, open and inactivated states of the sodium channel to reflect the compound's inhibitory or activating effects (Hille, B., Journal of General Physiology (1977), 69: 497-515).

Representative compounds of the present invention were subject to a manual patch clamp experiment and the purpose of this study was to test the effect of compounds on this ion channel current on a stable cell line transfected with a specific ion channel using a manual patch clamp method. The used stable cell lines CHO-hNav1.7 and HEK-hNav1.5 were from Genionics and WuXi Apptec (Shanghai) respectively.

Manual patch clamp experimental program is as follows:

(1) Preparation of solutions and compounds: The whole cell patch clamp technique was used to record hNav1.7 and hNav1.5 currents. In the experiment, the composition of extracellular fluid (mM): HEPES: 5, NaCl: 40, KCl: CaCl$_2$: 1, MgCl$_2$: 1, CdCl$_2$: 0.1, TEA-Cl: 20. The pH was adjusted to 7.3 with NaOH and the osmotic pressure was adjusted to 310-320 mOsm with sucrose, filtered and stored at 4° C. The composition of the intracellular fluid (mM): HEPES: 10, NaCl: 10, CsOH: 5, CsF: 140, EGTA: 1. The pH was adjusted to 7.3 with CsOH and the osmotic pressure was adjusted to 280-290 mOsm with sucrose, filtered and stored at −20° C.

The positive control and the test compound were firstly dissolved in 100% DMSO (Sigma-Aldrich, D2650), configured as stock solution at a concentration (100 nM, 1000 nM).) The above stock solution was serially diluted with DMSO prior to the experiment, the solution was further diluted with extracellular solution to obtain the test solution of the desired concentration. The final concentration of DMSO in extracellular fluid did not exceed 0.30%.

(2) Manual Patch Clamp Experiment: The cell suspension was added to a 35 mm petri dish and placed on an inverted microscope stage. The cells were perfused with an extracellular fluid and the flow rate was 1-2 mL/min after cell adherence. The glass microelectrode was prepared in two steps by a microelectrode puller with an inlet water resistance of 2-5 MΩ. A/D-D/A digital-analog conversion was performed by Digidata 1440 (Molecular Devices) and pCLAMP software (version 10.2, Molecular Devices) for stimulation and signal acquisition; the signal was amplified by patch clamp amplifier (Multiclamp 700B, Molecular Devices), and filtering is 4 KHz.

Two different voltage stimulation procedures were used in the hNav1.7 and hNav1.5 manual patch clamp experiments.

One is the inactivation stimulation program, the clamp potential is set at $V_{1/2}$ of the corresponding channel, i.e., about 50% of the channels are inactivated, then the voltage is applied to −120 mV for 50 ms, then depolarized to −10 mV for 20 ms leading to sodium current, and finally returned to the clamp potential. This stimulation program can also be called channel state-dependent voltage stimulation program.

The other is the non-inactivation stimulation program, the clamp potential is maintained at −120 mV, voltage stimulation is given to −10 mV for 20 ms leading to sodium current, and finally returned to the clamp potential. That is, all channels have not experienced inactivation status, but activate directly from the resting state under the conditions of the stimulation program.

The time intervals of these two voltage stimulation programs were 10 s. The inhibitory effect of the compound was calculated by the change of the current before and after dosing, the $IC_{50}$ value was fitted by the Hill equation. If the compound shows a multiple difference in channel effects at the above two different voltage stimulation, the compound is state-dependent on the channel. The results are shown in Table 1.

hNav1.8 Manual Patch Clamp Experiment

The recombinant HEK293 cell line stably expressed human voltage-gated sodium channel subtype 1.8 (hNaV1.8). The cDNA strictly follows the GenBank accession number: NM_014191.2. The HEK293 or CHO cell line stably expressing the sodium channel was cultured in F12/DMEM medium containing 10% fetal bovine serum and 0.8 mg/mL G418 at 37° C. with 5% carbon dioxide concentration. Extracellular fluid: 140 mM NaCl, 4 mM KCl, 1 mM $MgCl_2$, 2 mM $CaCl_2$, 5 mM D-Glucose monohydrate, 10 mM HEPES, pH=7.4 with NaOH. Electrode solution: 145 CsCl, 0.1 $CaCl_2$, 2 $MgCl_2$, 10 NaCl, 0.5 Na2-GTP (guanosine triphosphate disodium salt), 2 Mg-ATP (adenine nucleotide triphosphate), 1.1 EGTA (ethylene glycol bis (2-aminoethyl ether) tetraacetic acid), 10 HEPES (4-hydroxyethyl piperazine ethanesulfonic acid), pH 7.2 with CsOH.

A capillary glass tube (BF150-86-10, Sutter Instruments) was prepared into a recording electrode using a microelectrode puller (P97, Sutter Instruments). Microelectrode manipulator (MP285, Sutter Instruments) was manipulated under an inverted microscope (IX71, Olympus) to contact the recording electrode to the cells and suction was applied under negative pressure to form a G seal. After G seal, a rapid capacitance compensation was performed, then continue to apply negative pressure, suction cell membrane to create a whole-cell recording mode. Then slow capacitor compensation was performed and the film capacitance and series resistance were recorded without leakage compensation. Sodium current was recorded and data was collected by EPC-10 amplifier (HEKA) and stored in PatchMaster (HEKA) software.

Sequential drug administration began when the sodium currents recorded throughout the whole cell are stable, each drug was tested at 5-6 concentrations, and each drug concentration was tested for 5 minutes or the next concentration is tested after reaching stable state. Each cell itself was a control. At least 3 independent replicates were tested for each concentration. All electrophysiological experiments were performed at room temperature.

Sodium current voltage stimulation protocol is as follows: cell membrane voltage was clamped to −90 mV after forming a whole cell seal, the polarization voltage step was depolarized from −90 mV to −10 mV for 40 ms, the data were repeatedly collected every 10 seconds to observe the effect of drugs on sodium current.

Firstly, the current under each concentration and the current before administration were normalized and the corresponding inhibition rate (1−(peak current of test compound)/(current peak of control group)) of each drug concentration was calculated. The mean and standard error were calculated for each concentration and the half-inhibitory concentration of each compound was calculated using the following equation: Inhibition rate=$1/(1+(IC_{50}/C)^h)$.

The dose-dependent effect was non-linearly fit using the above equation, wherein C represents the drug concentration, $IC_{50}$ is the half-inhibitory concentration, h represents the Hill coefficient.

Manual Patch Clamp Experiment of hCav3.2 Channel:

The stable cell line HEK-hCav3.2 used for manual patch clamp experiments was from WuXi Apptec (Shanghai) Company.

Preparation of solutions and compounds: hCav3.2 current was recorded using whole-cell patch clamp technique. Composition of extracellular fluid (millimoles) in the experiment: HEPES 10, CsCl 6, $CaCl_2$) 2, TEA-Cl 140. The pH was adjusted to 7.4 with CsOH, while the osmotic pressure was adjusted to 310-320 mOsm with sucrose, filtered and stored at 4° C. Composition of the intracellular fluid (millimoles): HEPES 10, CsCl 55, CsSO4 75, $MgCl_2$ 10, EGTA 0.1. The pH was adjusted to 7.2 with CsOH, while the osmotic pressure was adjusted to 280-290 mOsm with sucrose, filtered and stored at −20° C. The positive control and the test compound were first dissolved in 100% DMSO (Sigma-Aldrich, D2650), configured as stock solution at a concentration. The above stock solution was serially diluted with DMSO prior to the experiment, and further diluted with extracellular fluid to give the desired concentration of test solution with a final DMSO concentration of not more than 0.30% in the extracellular solution.

Manual Patch Clamp Experiment: The cell suspension was added to a 35 mm petri dish and placed on an inverted microscope stage. The cells were perfused with an extracellular fluid and the flow rate was 1-2 mL/min after cell adherence. The glass microelectrode was pulled in two steps by a microelectrode puller with an inlet water resistance of 2-5 M. A/D-D/A digital-analog conversion was performed by Digidata 1440 (Molecular Devices) and pCLAMP software (version 10.2, Molecular Devices) for stimulation and signal acquisition; the signal was amplified by patch clamp amplifier (Multiclamp 700B, Molecular Devices), and filtering is 4 KHz. The following voltage stimulation program was applied to the hCav 3.2 manual patch clamp experiment, the clamp potential was set at −110 mV, a pulse voltage of −85 mV was applied for 500 ms, and then depolarized to −40 mV for 50 ms to induce hCav3.2 calcium channel current, and finally returned to the clamp potential. The stimulation program was repeated every 15 s and recorded continuously. The inhibitory effect of the compound was calculated by the change of the current before and after dosing, and the $IC_{50}$ value was fitted by the Hill equation.

TABLE 1

Inhibition of Nav1.7 by the representative compounds of the invention at two concentrations

| compound | 100 nM(%) | 1000 nM(%) |
|---|---|---|
| Z-80 | 90.47 | 96.83 |
| Z-89 | 94.85 | 99.69 |
| Z-92 | 94.54 | 97.28 |
| Z-117 | 89.31 | 96.13 |
| Z-142 | 92.17 | 97.75 |
| Z-150 | 93.33 | 96.70 |
| Z-159 | 90.58 | 97.32 |
| Z-164 | 89.66 | 101.53 |
| Z-172 | 89.11 | 97.24 |
| Z-173 | 93.85 | 100.05 |
| Z-174 | 78.01 | 95.12 |
| Z-177 | 89.18 | 98.05 |
| Z-178 | 89.08 | 98.70 |
| Z-180 | 70.42 | 97.77 |
| Z-182 | 77.25 | 97.62 |
| Z-183 | 90.80 | 99.47 |
| Z-184 | 70.30 | 98.48 |
| Z-185 | 85.31 | 94.93 |
| Z-186 | 83.26 | 100.00 |
| Z-187 | 89.70 | 100.26 |
| Z-188 | 81.83 | 98.10 |
| Z-189 | 83.85 | 99.16 |
| Z-191 | 73.26 | 94.95 |
| Z-192 | 77.66 | 98.36 |
| Z-193 | 72.58 | 95.66 |
| Z-195 | 76.72 | 92.69 |
| Z-196 | 85.03 | 93.02 |
| Z-197 | 83.63 | 100.39 |
| C1 | 52.03 | 64.05 |
| C2 | 49.22 | 64.84 |
| C3 | 17.56 | 52.26 |
| C4 | 18.58 | 58.91 |
| C5 | 17.19 | 36.76 |
| C6 | 11.15 | 57.25 |
| C7 | 31.14 | 67.54 |
| C8 | 46.99 | 66.80 |
| C9 | 5.49 | 29.06 |
| C10 | 7.83 | 24.67 |
| C11 | 23.06 | 51.85 |

TABLE 2

Selectivity of compound Z-164 for other ion channels

| Compound | Z-164 |
|---|---|
| Nav1.7($IC_{50}$/nM) | 24.57 |
| Nav1.5($IC_{50}$/nM) | 6160 |
| Nav1.8($IC_{50}$/nM) | 18900 |
| Cav3.2($IC_{50}$/nM) | >30000 |

As can be seen from Table 1, the representative compounds of the present invention have a higher inhibitory activity against Nav1 7. In addition, it was found that compared to the comparative compounds (such as C1-C11), the direct attachment of the nitrogen atoms on the five-membered (pyrrole ring) and six-membered (piperazine) nitrogen-containing heterocycles to the carbon atoms on benzene or pyridine ring has a significant effect on the inhibitory activity against Nav1.7. Studies have shown that when the nitrogen atom is not directly linked to benzene or pyridine ring, that is, the benzene or pyridine ring is connected to the nitrogen atom via a methylene or carbonyl group and the like, the inhibitory activity against Nav1.7 significantly reduced (for example, C1 and Z-197, C4 and Z-164).

In addition, if the benzene or pyridine ring is connected to the nitrogen atom via a methylene or carbonyl group and the like and $R_6$ is a methyl, the inhibitory activity against Nav1.7 significantly reduced (for example, C2 and Z-196, C11 and Z-197).

As can be seen from Table 2, compound Z-164 also shows selective inhibitory activity against other ion channels, particularly the Nav1.5, Nav1.8 sodium ion channels and calcium ion channels.

Assay 2: Effect on hERG Potassium Ion Channel 2.1 Cell Culture 2.1.1 Cells used in this experiment were CHO cell lines (supplied by Sophion Bioscience, Denmark) which were hERG cDNA transfectant and stably express hERG channels, and cell progeny was P15. Cells were cultured in medium containing the following ingredients Invitrogen): Ham's F12 medium, 10% (v/v) inactivated fetal bovine serum, 100 μl/ml hygromycin B, 100 μl/ml Geneticin.

2.1.2 CHO hERG cells were grown in Petri dishes containing the above medium and cultured in an incubator containing 5% $CO_2$ at 37° C. CHO hERG cells were transferred onto round glass plates in Petri dishes, and grown on the same culture medium under culture conditions as above for 24 h to 48 h prior to the electrophysiological experiments, and the density of CHO hERG cells on each round glass plate needs to meet the requirements that the vast majority of cells are independent and individual.

2.2 Experimental Solution

The following solutions (supplied by Sophion) were used for electrophysiological recording as shown in Table 3. The reagents used in this test were provided by Sigma.

TABLE 3

Intracellular and extracellular fluid composition

| Reagents | Extracellular fluid (mM) | Intracellular fluid (mM) |
|---|---|---|
| $CaCl_2$ | 2 | 5.37 |
| $MgCl_2$ | 1 | 1.75 |
| KCl | 4 | 120 |
| NaCl | 145 | — |
| Glucose | 10 | — |
| HEPES | 10 | 10 |
| EGTA | — | 5 |
| Na-ATP | — | 4 |
| PH | 7.4(adjusted with NaOH) | 7.25(adjusted with KOH) |
| Osmotic pressure | Osmotic pressure ~305 mOsm | Osmotic pressure ~295 mOsm |

2.3 Electrophysiological Recording System

In this experiment, whole-cell current recording was performed using a manual patch clamp system (HEKA EPC-10 signal amplification and digital conversion system, purchased from HEKA Electronic, Germany). The round glass slide, surface of which CHO hERG cells were grown on was placed in an electrophysiological recording slot under an inverted microscope. Extracellular fluid was used for steady perfsion in recording slot (approximately 1 ml per minute). A conventional whole-cell patch clamp current recording technique was used in the experiment. Unless otherwise specified, experiments were performed at normal room temperature (25° C.). Cell clamping was at −80 mV. Cell clamping voltage depolarized to +20 mV to activate hERG potassium channel, clamping to −50 mV after 5 sec to eliminate inactivation and generate tail currents. The tail current peak was used as a value for hERG current. The hERG potassium current recorded in the above steps could be superfused for test drug after the steady perfusion state of the extracellular fluid in the recording slot is stabilized until the inhibition of the hERG current by the drug reached a steady state.

The coincidence of the last three consecutive current recording lines was generally used as a criterion to determine whether the state is stable. After reaching a steady state, perfused with extracellular fluid until hERG current returned to the value before the drug adding. One or more drugs could be tested on a single cell, or multiple concentrations of the same drug, but needed to be rinsed with extracellular fluid between different drugs. Cisapride (purchased from Sigma) was used as a positive control in experiments to ensure that the quality of the used cells were normal.

2.4 Compound Treatment and Dilution

The compound was firstly dissolved in DMSO to a concentration of 10 mM and then the compound was diluted 1000-fold to the final 10 M test concentration using an extracellular solution. The final concentration of DMSO in the compound test solution was equal to 0.1%. The test concentration of positive control cisapride was 0.1 µM. All stock solutions and test solutions were subjected to regular 5-10 minute sonication and shaken to ensure complete dissolution of the compound.

2.5 Data Analysis

The test data were analyzed by the data analysis software provided by HEKA Patchmaster (V2x73.2), Microsoft Excel and Graphpad Prism 5.0. The experimental results were shown in Table 4.

TABLE 4

Inhibition of hERG potassium ion channels by representative compounds of the invention

| Compound | hERG inhibitory concentration IC50(µM) |
| --- | --- |
| Z-164 | >10 µM |
| Z-172 | >10 µM |
| Z-173 | >10 µM |
| Z-177 | >10 µM |
| Z-178 | >10 µM |
| Z-183 | >10 µM |
| Z-186 | >10 µM |
| Z-187 | >10 µM |
| Z-189 | >10 µM |

It can be seen from Table 4 that the representative compounds of the present invention have little inhibitory activity on the hERG potassium ion channel and thus have a selective inhibition on the potassium ion channel.

Assay 3: Cold Allodynia in SNL

The experimental animals were male Sprague-Dawley rats, weighing 140-150 g at the beginning of the experiment. The animals were purchased from Slack company, and food and water were supplied ad lib after purchase. Rats were group-housed, four rats/cage, and individually identified by marking on the tail.

Test Compound and Grouping:

Vehicle: 5% dimethylacetamide(Sinopharm Technology), 5% solutol (Sigma) and 90% saline Positive control: Pregabalin;

Test compound: compound Z-164;

The positive control and solvent composition of the test compound are 5% dimethylacetamide, 5% solutol and 90% saline.

The positive control and the test compound respectively inhibited SNL-induced cold allodynia in rats 2 hours after oral administration at the dose of 30 mg/kg, as shown in Table 5

TABLE 5

Grouping of compound pharmacodynamics testing on cold allodynia in SNL rats

| Group | Model | Substance to be tested | Dose (mg/kg) | Dose Volume (mL/kg) | Route of Admin | Number of Animal |
| --- | --- | --- | --- | --- | --- | --- |
| 1 | Naive | — | — | — | — | 10 |
| 2 | SNL | Vehicle | — | — | p.o | 10 |
| 3 | SNL | Pregabalin | 30 | 5 | p.o | 10 |
| 4 | SNL | compound Z-164 | 30 | 5 | p.o | 10 |

30 mg/kg Compound Z-164:1.23 mL of dimethylacetamide was added to 148.11 mg of compound Z-164, stirred well until fully dissolved, and then 1.23 mL solutol was added and mixed well. Final volume was made up with 90% saline to 21.44 mL and mixed well before oral administration.

30 mg/kg Pregabalin: 1.08 mL of dimethylacetamide was added to 129.48 mg of Pregabalin, stirred well until fully dissolved, and then 1.08 mL solutol was added and mixed well. Final volume was made up with 90% saline to 21.58 mL and mixed well before oral administration.

Procedures:

1.1. Spinal Nerve Ligation (SNL) model

Surgical procedures are performed aseptically.

The surgical instruments (scissors, tweezers, scalpels, surgical cotton, sutures, retractor) are sterilized prior to surgery.

Animals were anesthetized with pentobarbital (50 mg/kg, i.p.). A toe pinch was used to ensure that the animals were fully anesthetized prior to surgery. Put ophthalmic ointment in the animal's eyes to prevent the corneas from drying out.

The fur on the surgical area of animal's lower body was shaved, and the skin of the surgical area was swabbed with 3 rounds of Betadine and 70% ethanol. The skin was allowed to dry before surgery.

A longitudinal incision will be made by scalpel at the lower lumbar and sacral levels, exposing the paraspinal muscles on the left side. The retractor was used to separate the muscles and tissues to expose the vertebra.

The left L5 and L6 spinal nerves will be isolated and tightly ligated with 6-0 silk thread.

The wound was closed with sutures.

The surgical instruments were cleaned, and sterilized by using a glass bead sterilizer.

Animals were placed on the electric blanket after surgery. Inject 5 ml sterile saline to prevent dehydration. The animals were returned to their home cage after fully awake (walking around).

1.2. Baseline Test of Cold Allodynic and Grouping

The baseline of cold allodynic was measured in rats two days before dosing. Use a pipette to apply 100 µl of acetone to the animal's lateral hind paw skin and the time of slapping, flinching, lifting, licking of the affected paw were recorded for one minute. Acetone was applied twice in total and the two applications were 10 minutes apart. The sum of the two times was recorded as cold allodynic time in rats. The rats were grouped randomized according to the results of baseline test of cold allodynic the day before dosing.

1.3. Cold Allodynic Testing

A pipette was used to apply 100 μl of acetone to the animal's lateral hind paw skin two hours after dosing and the time of slapping, flinching, lifting, licking of the affected paw were recorded for one minute. Acetone was applied twice and the two applications were 10 minutes apart. The sum of the two times was recorded as cold allodynic time in rats.

1.4. Dosing

Oral administration was performed two hours before cold allodynic testing.

1.5. Data Collection and Analysis

Data were collected with Excel and analyzed with Prism. Conclusions:

TABLE 6

Results of cold allodynic test in rats (compound Z-164)

| Group | Response duration (mean, s) | | Anti-allodynia Effect (mean, %) |
| --- | --- | --- | --- |
| | the first day (Baseline) | the next day (Baseline) | |
| Naive | 4.8 | 4.92 | — |
| Vehicle | 36.832 | 37.097 | — |
| Compound Z-164 | 36.831 | 24.327 | 39.7 |
| Positive control | 36.847 | 13.005 | 74.9 |

Anti-allodynia Effect (%) = (The mean of vehicle − The mean of dosing group)/(The mean of vehicle − The mean of naive) × 100%

Figure 2:
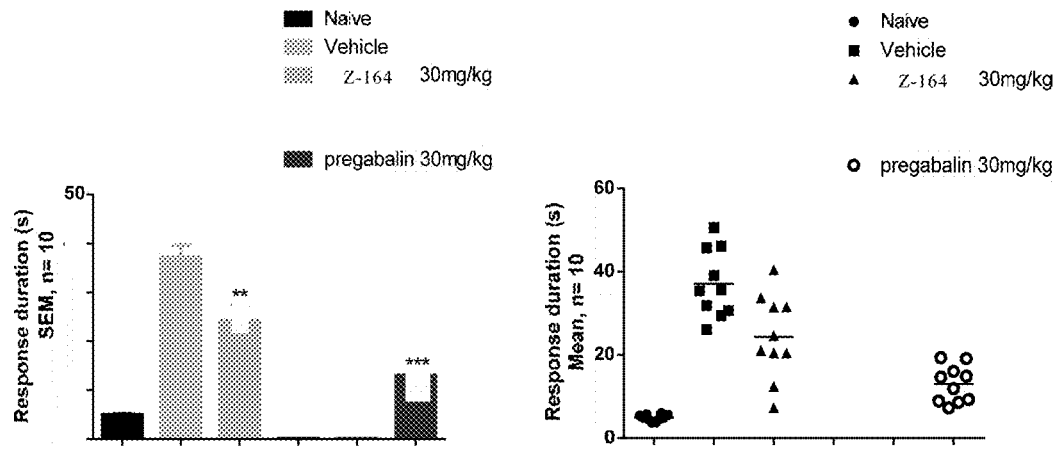
FIG. 2 shows the anti-allodynic effects of compound Z-164 in SNL rats model.

The experimental results are shown in FIG. 1 and FIG. 2, indicating that compound Z-164 of the present invention exhibits inhibition of SNL-induced cold allodynia in SNL rats model two hours post oral administration, and has a statistically significant inhibitory effect in the neuralgia model of rats.

FIG. 2 shows the anti-allodynic effects of compound Z-164 in SNL rats. $p<0.01$, *$p<0.001$ vs. vehicle group by one way ANOVA followed by Dunnett's multiple comparison test. Compound Z-164 and positive control at the dose of 30 mg/kg have inhibition of SNL-induced cold allodynia respectively 2 hr post oral administration.

Assay 4: Metabolism Stability Assay

1. Preparation of Buffer

Buffer A: 1 L solution of 100 mM potassium dihydrogen phosphate containing 1 mM EDTA (Sigma, V900157-100G) was prepared.

Buffer B: 1 L solution of 100 mM dipotassium hydrogen phosphate containing 1 mM EDTA was prepared.

Buffer C: 700 mL of buffer B was taken out and titrated with buffer A to pH 7.4.

2. Preparation of the Compound to be Tested and the Positive Control Drug (Ketanserin (Sigma S006-10MG))

2.1 10 μl of 10 mM compound to be tested and 10 μl of 10 mM ketanserin were taken and 190 μl of pure acetonitrile was added to each of them to prepare 500 μM compound to be tested and ketanserin, respectively.

2.2 20 μl (20 mg/mL) of liver microsomes (Corning Lot. NO. 4133007) stock solution was added to 513.4 μl of buffer C on wet ice. 0.75 mg/mL liver microsomal solution was obtained.

2.3 1.5 μl of each of the above-mentioned compound to be tested and ketanserin solution was added to 498.5 μl of liver microsomal solution (0.7 5 mg/mL) respectively on wet ice. 1.5 μM mixed solution of compound to be tested and 1.5 μM mixed solution of ketanserin were obtained.

2.4 At the time points 0, 5, 15, 30, 45, and 60 min, 30 μl of the mixed solution of compound to be tested and 30 μl of the mixed solution of ketanserin were dispensed into the reaction plate on wet ice, respectively.

2.5 5 mg reduced coenzyme II (Roche, 10621706001) was weighed and dissolved in 1 mL of buffer C. 6 mM reduced coenzyme II solution was obtained. The reduced coenzyme II solution was dispensed into the reaction plate.

2.6 Imipramine was dissolved to give a 10 mM solution. 10 μl of imipramine solution was added to 100 mL of blank acetonitrile to generate the internal reference.

2.7 At 0 min, 135 μL of iced acetonitrile (Merck (Lot. 1778229518)) containing the internal reference was added to each well and then 15 μL of buffer C was added.

2.8 The reaction plate was placed into a 37° C. water bath incubator for 5 min. In the reaction plate, 15 μL of reduced coenzyme II solution was added to each well to initiate the reaction, and the timing was started. At the time points of 5, 15, 30, 45, and 60 min, 135 μL of iced acetonitrile containing the internal reference was added to each well to terminate the reaction.

2.9 The reaction plate was sealed with an aluminum film, placed on a vibration mixer and shaken at 500 rpm for 5 min. The plate was then centrifuged in a centrifuge at 3750 rp for 15 min.

2.10 The sample was diluted with pure water in accordance with the ratio of 1:1 and detected by LC/MS. The clearance ratio was calculated according to the following formula based on the obtained values, and shown in Table 7.

Half-life: 0.693/K (the slope by plotting based on the incubation time and logarithm of the concentration value)

Clearance ratio: (0.693/half-life)*(1/protein concentration (0.5 mg/mL))*(proportional factor)

Wherein, the K value and the proportional factor were calculated by those skilled in the art according to the methods described in the prior art and contained in the instructions of the liver microsome product.

TABLE 7

Experimental results of Metabolic stability of human liver microsomes

| | human | |
| --- | --- | --- |
| Compound No. | $T_{1/2}$(min) | Clearance ratio (mL/min/kg) |
| Z-80 | 47.79 | 36.37 |
| Z-89 | 267.69 | 6.49 |
| Z-92 | 25191.01 | 0.07 |
| Z-117 | 321.59 | 5.41 |
| Z-119 | 77.03 | 22.57 |
| Z-159 | 470.62 | 3.69 |
| Z-164 | 86.39 | 20.12 |
| Z-172 | 788.38 | 2.20 |
| Z-173 | 280.47 | 6.20 |
| Z-177 | ∞ | 0.00 |
| Z-178 | 72.80 | 23.88 |
| Z-189 | ∞ | 2.74 |
| Z-195 | 83.31 | 20.86 |
| C12 | 22.21 | 78.28 |
| C13 | 12.51 | 138.91 |

It can be seen from Table 7 that the compounds of the present invention have good metabolic stability. It has also been found that the change of the substituent $R_6$ has obvious influence on the metabolic stability. In particular, when cyclopropyl is changed to methyl, the metabolic stability is significantly reduced (eg C12 and Z-173, C13 and Z-164).

All publications mentioned herein are incorporated by reference as if each individual document was cited as a reference, as in the present application. It should also be understood that, after reading the above teachings of the present invention, those skilled in the art can make various changes or modifications, equivalents of which falls in the scope of claims as defined in the appended claims.

The invention claimed is:

1. A compound selected from the group consisting of:

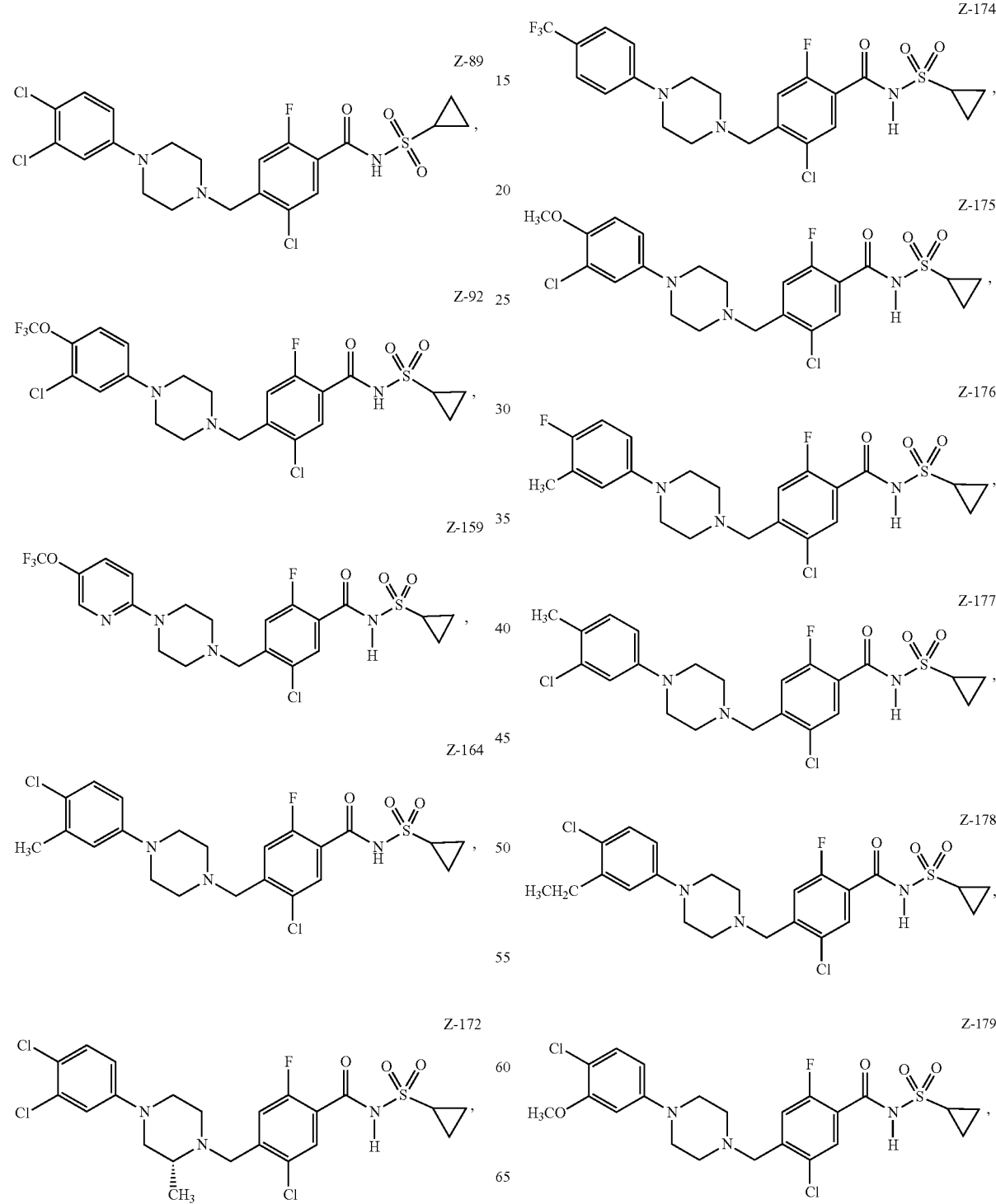

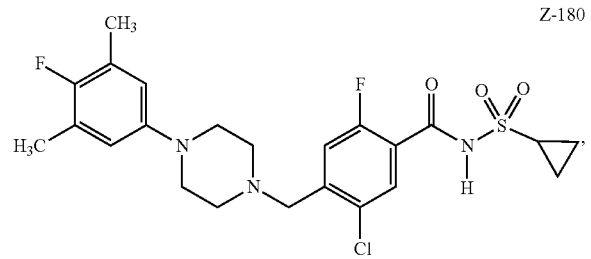 Z-180
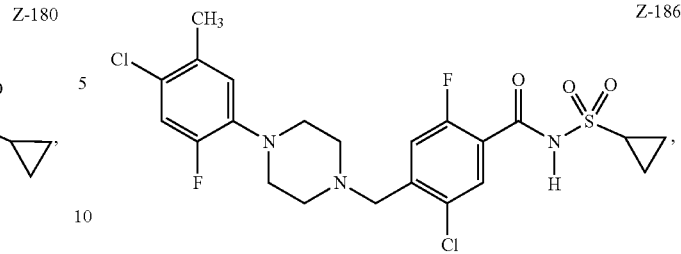 Z-186
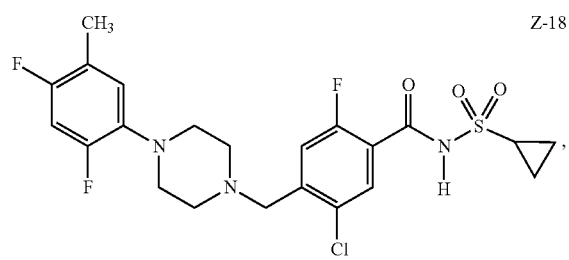 Z-181
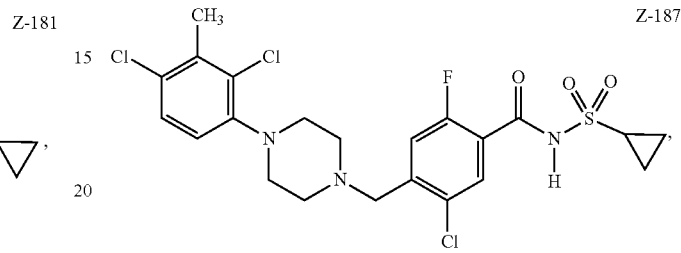 Z-187
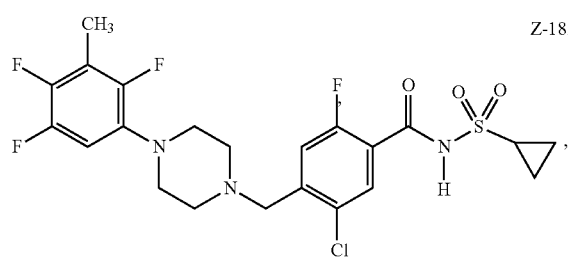 Z-182
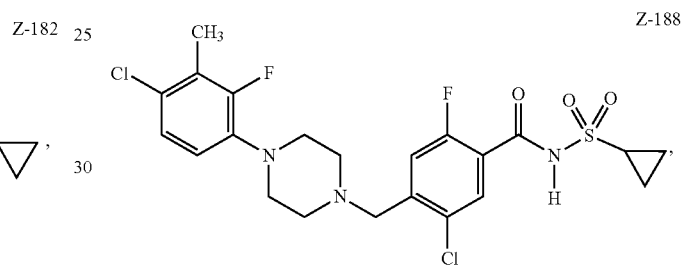 Z-188
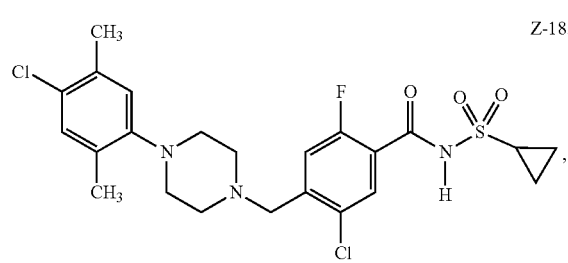 Z-183
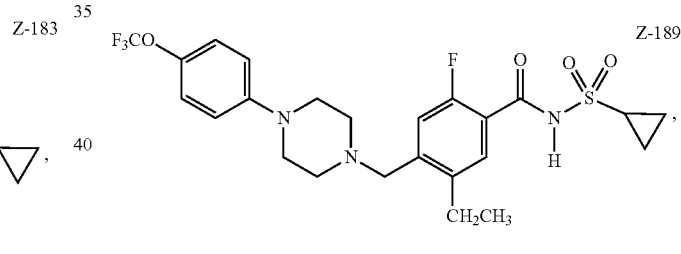 Z-189
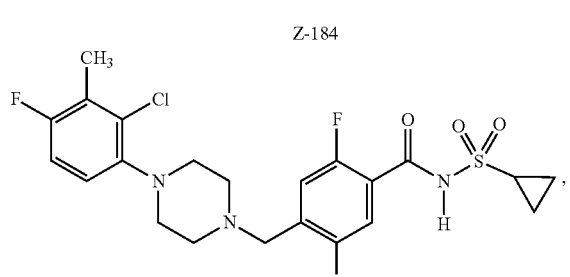 Z-184
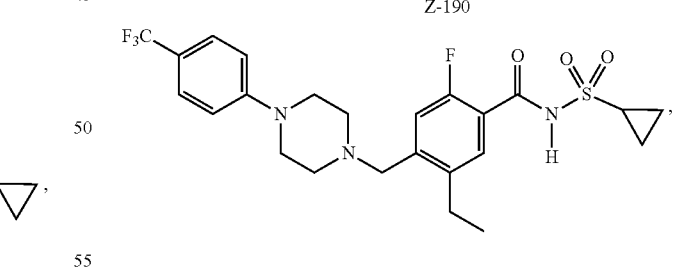 Z-190
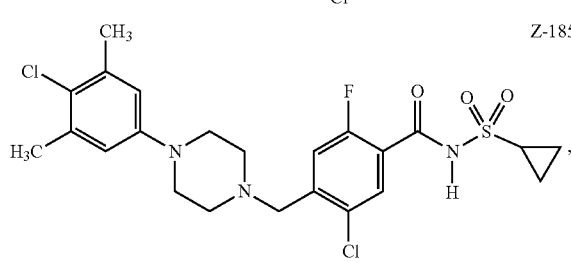 Z-185
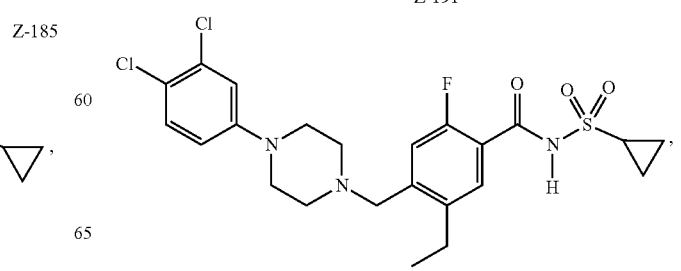 Z-191

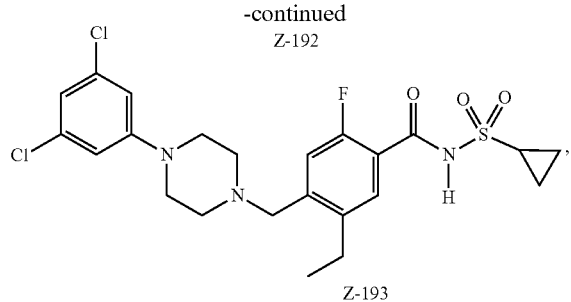
Z-192
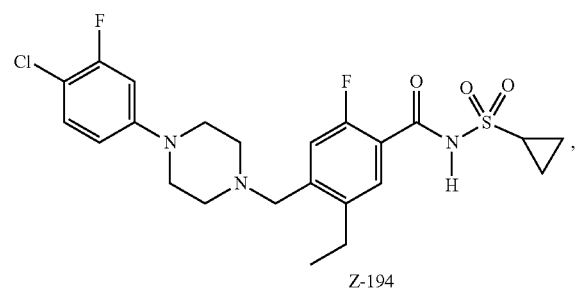
Z-193
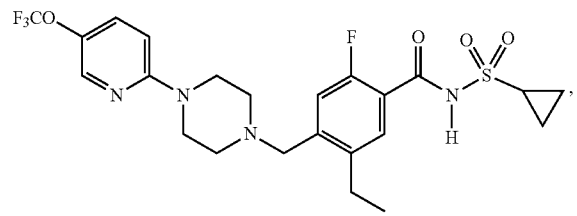
Z-194
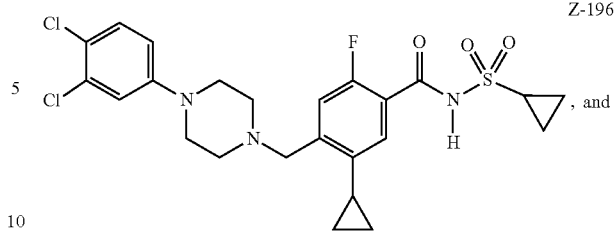
Z-196
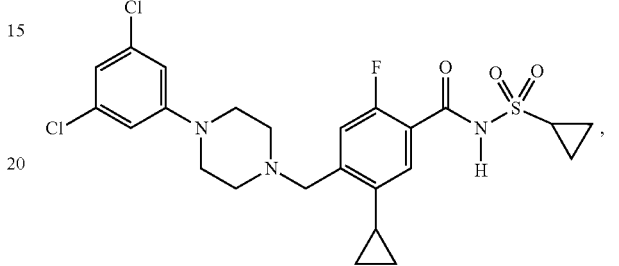
Z-197
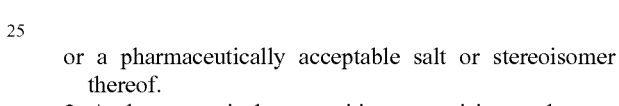
or a pharmaceutically acceptable salt or stereoisomer thereof.
2. A pharmaceutical composition comprising a pharmaceutically acceptable carrier and a compound of claim 1, or a pharmaceutically acceptable salt or stereoisomer thereof.
* * * * *